United States Patent
Puschl et al.

(10) Patent No.: US 7,732,463 B2
(45) Date of Patent: *Jun. 8, 2010

(54) 4-(2-PHENYLSULFANYL-PHENYL)-PIPERIDINE DERIVATIVES AS SEROTONIN REUPTAKE INHIBITORS

(75) Inventors: Ask Puschl, Frederiksberg (DK); Benny Bang-Andersen, Kobenhaven (DK); Morten Jorgensen, Bagsvaerd (DK); Thomas Ruhland, Roskilde (DK); Tine B. Stensbol, Vaerlose (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 1001 days.

This patent is subject to a terminal disclaimer.

(21) Appl. No.: 10/551,883

(22) PCT Filed: Apr. 2, 2004

(86) PCT No.: PCT/DK2004/000244

§ 371 (c)(1),
(2), (4) Date: Nov. 29, 2005

(87) PCT Pub. No.: WO2004/087156

PCT Pub. Date: Oct. 14, 2004

(65) Prior Publication Data

US 2006/0100242 A1    May 11, 2006

Related U.S. Application Data

(60) Provisional application No. 60/460,528, filed on Apr. 4, 2003.

(30) Foreign Application Priority Data

Apr. 4, 2003    (DK) ................. 2003 00520

(51) Int. Cl.
*A61K 31/445*    (2006.01)
*C07D 211/20*    (2006.01)

(52) U.S. Cl. .................. 514/317; 546/236

(58) Field of Classification Search ............. 514/317; 546/236
See application file for complete search history.

(56) References Cited

U.S. PATENT DOCUMENTS

| | | | |
|---|---|---|---|
| 3,803,143 A | | 4/1974 | Tanaka et al. |
| 4,018,830 A | | 4/1977 | Christy |
| 4,055,665 A | | 10/1977 | Christy |
| 4,056,632 A | | 11/1977 | Mehta et al. |
| 4,066,654 A | | 1/1978 | Adelstein et al. |
| 4,198,417 A | | 4/1980 | Ong et al. |
| 4,198,419 A | * | 4/1980 | Ong et al. ........... 514/317 |
| 4,241,071 A | | 12/1980 | Martin et al. |
| 5,095,039 A | | 3/1992 | Mehta et al. |
| 6,410,736 B1 | | 6/2002 | Howard, Jr. et al. |
| 6,436,938 B1 | | 8/2002 | Howard, Jr. |
| 6,596,741 B2 | | 7/2003 | Howard et al. |
| 6,677,378 B2 | | 1/2004 | Howard, Jr. et al. |
| 6,699,864 B2 | * | 3/2004 | Ruhland et al. .......... 514/235.8 |
| 7,138,407 B2 | | 11/2006 | Ruhland et al. |
| 7,144,884 B2 | | 12/2006 | Ruhland et al. |
| 7,148,238 B2 | | 12/2006 | Ruhland et al. |

FOREIGN PATENT DOCUMENTS

| | | |
|---|---|---|
| EP | 0 273 199 A2 | 7/1988 |
| EP | 0 396 827 A1 | 11/1990 |
| EP | 0 402 097 A1 | 12/1990 |
| EP | 0 814 084 A1 | 12/1997 |
| EP | 0 921 124 A1 | 6/1999 |
| EP | 0 755 923 | 4/2005 |
| WO | WO 93/12080 A1 | 6/1993 |
| WO | WO 97/17325 A1 | 5/1997 |
| WO | WO 97/17352 A1 | 5/1997 |
| WO | WO 98/08817 A1 | 3/1998 |
| WO | WO 99/17777 | 4/1999 |
| WO | WO 00/50380 A1 | 8/2000 |

(Continued)

OTHER PUBLICATIONS

Ong. et al. "Phenylthiphenylpiperidines" CA 93:71569 (1980).*

(Continued)

*Primary Examiner*—Celia Chang
(74) *Attorney, Agent, or Firm*—Stephen G. Kalinchak; Margaret M. Buck

(57) ABSTRACT

The invention provides compounds represented by the general formula (I) wherein the substituents are defined in the application. The compounds are useful in the treatment of an affective disorder, including depression, anxiety disorders including general anxiety disorder and panic disorder and obsessive compulsive disorder.

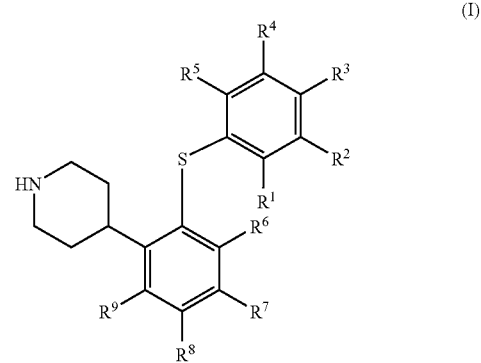

16 Claims, No Drawings

FOREIGN PATENT DOCUMENTS

| | | |
|---|---|---|
| WO | WO-00/59878 A2 | 10/2000 |
| WO | WO-00/59878 A3 | 10/2000 |
| WO | WO 00/66537 A1 | 11/2000 |
| WO | WO-01/10842 A2 | 2/2001 |
| WO | WO-01/10842 A3 | 2/2001 |
| WO | WO 01/27068 A1 | 4/2001 |
| WO | WO 01/49678 | 7/2001 |
| WO | WO 01/49681 | 7/2001 |
| WO | WO-02/062766 A2 | 8/2002 |
| WO | WO-02/062766 A3 | 8/2002 |
| WO | WO 02/098857 A1 | 12/2002 |
| WO | WO 03/029232 A1 | 4/2003 |
| WO | WO 03/055873 A1 | 7/2003 |
| WO | WO-2004/085385 A2 | 10/2004 |
| WO | WO-2004/085385 A3 | 10/2004 |
| WO | WO 2004/087155 A1 | 10/2004 |
| WO | WO 2004/087662 A1 | 10/2004 |
| WO | WO-2005/000309 A2 | 1/2005 |
| WO | WO-2005/000309 A3 | 1/2005 |

OTHER PUBLICATIONS

Pueschl et al. "Preparation of [(phenylsulfanyl)phenyl . . . " CA 141:332062 (2004).*

Ruhland et al. "Preparation of phenylpiperazines . . . " CA 138:304306 (2003).*

Axford, L. et al., "Bicyclo[2.2.1]heptanes as Novel Triple Re-uptake Inhibitors for the Treatment of Depression", Bioorg. Med. Chem. Lett., 2003, 13:3277-3280.

Buckle, D.R. and Rockell, C.J.M., "A Versatile Two-Stage Synthesis of 2-Substituted Benzo [b]furans from (2-Methoxyphenyl)ethynes". J. Chem. Soc. Perkin Trans. I, 1985: 2443-2446.

Clayden, J., "Regioselective Synthesis of Organolithiums by X-Li Exchange." In Organolithiums: Selectivity for Synthesis. Tetrahedron Organic Chemistry Series. 2002, New York, Pergamon. 23: 111-147.

Dabrowski, M., et al. "Halogen-lithium exchange between substituted dihalobenzenes and butyllithium: application to the regioselective synthesis of functionalized bromobenzaldehydes." Tetrahedron. 2005. 61:6590-6595.

Emond, P., et al., "Substituted Diphenyl Sulfides as Selective Serotonin Transporter Ligands: Synthesis and In Vitro Evaluation", J. Med. Chem., 2002, 45(6):1253-1258.

Hawkins, D.G., et al., "Competitive Cyclisation of Singlet and Triplet Nitrenes. Part 7. Reaction Pathways of 2-Azidophenyl Benzothienyl Azides", J. Chem. Soc., Perkin Trans. I, 1979, 3207-3210.

Hurd, C.D. and Hoffman, W.A. "Directed Ring Closure in the Synthesis of Chromans and Coumarans from ortho-Allylphenols". J. Am. Chem. Soc. 1940. 5:212-222.

Jackson, A., et al., "Electrophilic Substitution in Indoles Part 16. The Formation of Indolobenzothiazines and Indolobenzothiazepines by Intramolecular Cyclisation of (o-Nitrophenylthio)indoles", J. Chem. Res. Miniprint 9, 1988, 2017-2063.

Jilek, J., et al., "Potential Antidepressants: 2-(Methoxy- and Hydroxy-Phenylthio)Benzylamines as Selective Inhibitors of 5-Hydroxytryptamine Re-uptake in the Brain", Collect. Czech. Chem. Commun., 1989, 54:3294-3338.

Klint, T. and Weikop, P. "Monoamine transporters as continuing targets for drug discovery in depression". Drug Discovery Today: Therapeutic Strategies. 2004. 1(1):111-116.

Kunz, K., et al. "Renaissance of Ullmann and Goldberg Reactions—Progress in Copper Catalyzed C-N-, C-O- and C-S-Coupling". Synlett. 2003, 15: 2428-2439.

Mar., J. Advanced Organic Chemistry: Reaction Mechanisms, and Structure. 3rd ed. 1985. New York, John Wiley & Sons. pp. 342-343; 589-590; 684-685.

Millan, M.J. "The neurobiology and control of anxious states". Progress in Neurobiology. 2003. 70:83-244.

Oya, S., et al., "A New Single-Photon Emission Computed Tomography Imaging Agent for Serotonin Transporters: [123I]IDAM, 5-Iodo-2-((2-((dimethylamino)methyl)-phenyl)thio)benzyl Alcohol", J. Med. Chem. 1999, 42(3):333-335.

Oya, S., et al., "New PET Imaging Agent for the Serotonin Transporter: [1 8 F]ACF (2-[(2-Amino-4-chloro-5-fluorophenyl)thio]-N,N-dimethyl-benzenmethanamine)", J. Med. Chem. 2002, 45 (21):4716-4723.

Parham, W.E. and Jones, L.D. "Elaboration of Bromoarylnitriles". J. Org. Chem. 1976. 41(7):1187-1191.

Ragno, R., et al., "Docking and 3-D QSAR Studies on Indolyl Aryl Sulfones. Binding Mode Exploration at the HIV-1 Reverse Transcriptase Non-Nucleoside Binding Site and Design of Highly Active N-(2-Hydroxyethyl) carboxamide and N-(2-hydroxyethyl)carbohydrazide Derivatives", J. Med. Chem., 2005, 48(1):213-223.

Sakamuri, S., et al. "Pharmacophore-Based Discovery, Synthesis, and Biological Evaluation of 4-Phenyl-1-arylalkyl Piperidines as Dopamine Transporter Inhibitors". Bioorg. Med. Chem. Lett. 2001. 11:495-500.

Sato, T., et al. "Selective inhibition of monoamine neurotransmitter transporters by synthetic local anesthetics". Naunyn-Schmiedeberg's Arch Pharmacol. 2000. 361:214-220.

Siemsen, P., et al. "Acetylenic Coupling: A Powerful Tool in Molecular Construction". Angew. Chem. Int. Ed. 2000. 39:2632-2657.

Silverman, R.B. The Organic Chemistry of Drug Design and Drug Action. 1992. San Diego. Academic Press. p. 19.

Silvestri, R., et al., "Novel Indolyl Aryl Sulfones Active Against HIV-1 Carrying NNRTI Resistance Mutations: Synthesis and SAR Studies", J. Med. Chem. 2003, 46(12):2482-2493.

Sindelar, K., et al., "Potential Antidepressants and Inhibitors of 5-Hydroxy-Tryptamine and Noradrenaline Re-uptake in the Brain: N,N-Dimethyl-(Arylthio)Thenylamines and N,N-Dimethyl-2-(Thienylthio)Benzylamines", Collect. Czech. Chem. Commun. 1991, 56:449-458.

Tamiz, A.P., et al. "Further SAR Studies of Piperidine-Based Analogues of Cocaine. 2. Potent Dopamine and Serotonin Reuptake Inhibitors". J. Med. Chem. 2000. 43(6):1215-1222.

Wang, S., et al. "Discovery of a Novel Dopamine Transporter Inhibitor, 4-Hydroxy-1-methyl 4 (4-methylphenyl)-3-piperidyl 4-Methylphenyl Ketone, as a Potential Cocaine Antagonist through 3D-Database Pharmacophore Searching. Molecular Modeling, Structure—Activity Relationships, and Behavioral Pharmacological Studies". J. Med. Chem. 2000. 43(3): 351-360.

Martin et al., "Synthesis of Spiro[isobenzofuran-1(3H),4'-piperidines] as Potential Central Nervous System Agents. 5. Conformationally Mobile Analogues Derived by Furan Ring Opening," *Journal of Medicinal Chemistry*, vol. 22, No. 11, pp. 1347-1354, 1979.

* cited by examiner

4-(2-PHENYLSULFANYL-PHENYL)-PIPERIDINE DERIVATIVES AS SEROTONIN REUPTAKE INHIBITORS

CROSS-REFERENCE TO PRIOR APPLICATION

This is the U.S. national stage under 35 U.S.C. §371 of International Patent Application No. PCT/DK04/00244, filed Apr. 2, 2004, and claims benefit of Denmark Patent Application No. PA200300520, filed Apr. 4, 2003, and U.S. Provisional Application 60/460,528, filed Apr. 4, 2003. The International Application was published in English on Oct. 14, 2004 as WO 2004/087156 A1 under PCT Article 21(2).

The present invention relates to novel compounds which are serotonin reuptake inhibitors and as such effective in the treatment of for example depression and anxiety.

BACKGROUND OF THE INVENTION

Selective serotonin reuptake inhibitors (hereinafter referred to as SSRIs) have become first choice therapeutics in the treatment of depression, certain forms of anxiety and social phobias, because they are effective, well tolerated and have a favourable safety profile compared to the classic tricyclic antidepressants.

However, clinical studies on depression indicate that non-response to SSRIs is substantial, up to 30%. Another, often neglected, factor in antidepressant treatment is compliance, which has a rather profound effect on the patient's motivation to continue pharmacotherapy.

First of all, there is the delay in therapeutic effect of SSRIs. Sometimes symptoms even worsen during the first weeks of treatment. Secondly, sexual dysfunction is a side effect common to all SSRIs. Without addressing these problems, real progress in the pharmacotherapy of depression and anxiety disorders is not likely to happen.

In order to cope with non-response, psychiatrists sometimes make use of augmentation strategies. Augmentation of antidepressant therapy may be accomplished through the co-administration of mood stabilizers such as lithium carbonate or triiodothyronin or by the use of electroshock.

The effect of combined administration of a compound that inhibits serotonin reuptake and a $5\text{-HT}_{1A}$ receptor antagonist has been evaluated in several studies (Inis et al. *Eur. J. Pharmacol.* 1987, 143, 1095-204 and Gartside *Br. J. Pharmacol.* 1995, 115, 1064-1070, Blier et al. *Trends in Pharmacol. Science* 1994, 15, 220). In these studies, it was found that $5\text{-HT}_{1A}$ receptor antagonists would abolish the initial brake on 5-HT neurotransmission induced by the serotonin reuptake inhibitors and thus produce an immediate boost of 5-HT transmission and a rapid onset of therapeutic action.

Several patent applications have been filed, which cover the use of a combination of a $5\text{-HT}_{1A}$ antagonist and a serotonin reuptake inhibitor for the treatment of depression (see e.g. EP-A2-687472 and EP-A2-714663).

Another approach to increase terminal 5-HT would be through blockade of the $5\text{-HT}_{1B}$ autoreceptor. Microdialysis experiments in rats have indeed shown that increase of hippocampal 5-HT by citalopram is potentiated by GMC 2-29, an experimental $5\text{-HT}_{1B}$ receptor antagonist.

Several patent applications covering the combination of an SSRI and a $5\text{-HT}_{1B}$ antagonist or partial agonist have also been filed (WO 97/28141, WO 96/03400, EP-A-701819 and WO 99/13877).

It has previously been found that the combination of a serotonin reuptake inhibitor with a compound having $5\text{-HT}_{2C}$ antagonistic or inverse agonistic effect (compounds having a negative efficacy at the $5\text{-HT}_{2C}$ receptor) provides a considerable increase in the level of 5-HT in terminal areas, as measured in microdialysis experiments (WO 01/41701). This would imply a shorter onset of antidepressant effect in the clinic and an augmentation or potentiation of the therapeutic effect of the serotonin reuptake inhibitor (SRI).

The present invention provides compounds which are serotonin reuptake inhibitors for the treatment of affective disorders, such as depression, anxiety disorders including general anxiety disorder, social anxiety disorder, post traumatic stress disorder, obsessive compulsive disorder, panic disorder, panic attacks, specific phobias, social phobia and agoraphobia. Some of the compounds also have a combined effect of serotonin reuptake inhibition and $5\text{-HT}_{2C}$ receptor modulation, which according to WO01/41701 would imply a faster onset of antidepressant activity.

SUMMARY OF THE INVENTION

The present invention provides compounds of the general formula I

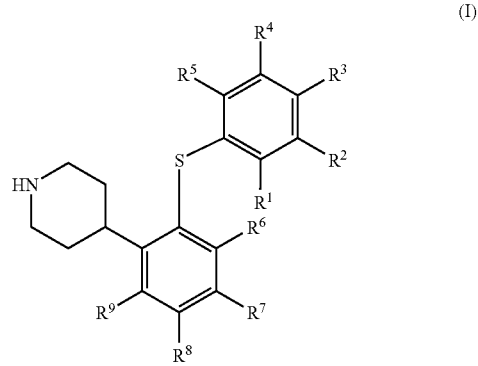

(I)

wherein $R^1$, $R^2$, $R^3$, $R^4$, $R^5$, $R^6$, $R^7$, $R^8$, and $R^9$ are as defined below.

The invention provides a compound according to the above for use as a medicament.

The invention provides a pharmaceutical composition comprising a compound according to the above or a pharmaceutically acceptable acid addition salt thereof and at least one pharmaceutically acceptable carrier or diluent.

The invention provides the use of a compound according to the above or a pharmaceutically acceptable acid addition salt thereof for the preparation of a medicament for the treatment of affective disorders, such as depression, anxiety disorders including general anxiety disorder, social anxiety disorder, post traumatic stress disorder, obsessive compulsive disorder, panic disorder, panic attacks, specific phobias, social phobia and agoraphobia.

The invention provides a method for the treatment of an affective disorders, such as depression, anxiety disorders including general anxiety disorder, social anxiety disorder, post traumatic stress disorder, obsessive compulsive disorder, panic disorder, panic attacks, specific phobias, social phobia and agoraphobia in a living animal body, including a human, comprising administering a therapeutically effective amount of a compound according to the above or a pharmaceutically acceptable acid addition salt thereof.

DEFINITION OF SUBSTITUENTS

Halogen means fluoro, chloro, bromo or iodo.

The expression $C_{1\text{-}6}$-alk(en/yn)yl means a $C_{1\text{-}6}$-alkyl, $C_{2\text{-}6}$-alkenyl or a $C_{2\text{-}6}$-alkynyl group.

The term $C_{1-6}$ alkyl refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, including one double bond and one triple bond respectively, including but not limited to ethenyl, propenyl, butenyl, ethynyl, propynyl and butynyl.

The terms $C_{1-6}$-alk(en/yn)yloxy, $C_{1-6}$ alk(en/yn)ylsulfanyl, hydroxy-$C_{1-6}$-alk(en/yl)yl, halo-$C_{1-6}$-alk(en/yn)yl, cyano-$C_{1-6}$-alk(en/yn)yl, $NR^zR^w$-$C_{1-6}$-alk(en/yn)yl, $C_{1-6}$-alk(en/yn)yloxy-$C_{1-6}$-alk(en/yn)yl and halo-$C_{1-6}$-alk(en/yn)yloxy designate such groups in which the $C_{1-6}$-alk(en/yn)yl are as defined above. Halo means halogen.

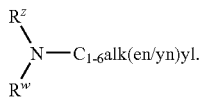

The term $C_{3-8}$ cycloalkyl designates a monocyclic or bicyclic carbocycle having three to eight C-atoms, including but not limited to cyclopropyl, cyclopentyl, cyclohexyl, etc.

The term $C_{3-8}$ cycloalkenyl designates a monocyclic or bicyclic carbocycle having three to eight C-atoms and including one double bond.

In the term $C_{3-8}$-cycloalk(en)yl-$C_{1-6}$-alk(en/yn)yl, $C_{3-8}$-cycloalk(en)yl and $C_{1-6}$-alk(en/yn)yl are as defined above.

The term 3-7-membered ring optionally containing one further heteroatom, such as N, O, or S, as used herein refers to ring systems such as 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, all of which may be further substituted with a group selected from a $C_{1-6}$-alk(en/yn)yl, hydroxy, hydroxy-$C_{1-6}$-alk(en/yn)yl, $C_{1-6}$-alk(en/yn)yloxy-$C_{1-6}$-alk(en/yn)yl.

DESCRIPTION OF THE INVENTION

The present invention relates to 4-(2-phenylsulfanyl-phenyl)-piperidine derivatives which are serotonin reuptake inhibitors and as such effective in the treatment of for example depression and anxiety.

Accordingly the present invention relates to a compound represented by the general formula I

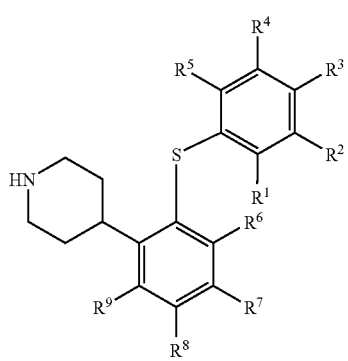

wherein
$R^1$, $R^2$, $R^3$, $R^4$, $R^5$ are independently selected from hydrogen, halogen, cyano, $C_{1-6}$alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, or $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, or $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, $C_{3-8}$-cycloalk(en)yl-$C_{1-6}$-alk(en/yn)yl; or $R^x$ and $R^y$ together with the nitrogen to which they are attached form a 3-7-membered ring which optionally contains one further heteroatom;

$R^6$, $R^7$, $R^8$, $R^9$ are independently selected from hydrogen, halogen, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, or $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, or $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, $C_{3-8}$-cycloalk(en)yl-$C_{1-6}$-alk(en/yn)yl; or $R^x$ and $R^y$ together with the nitrogen to which they are attached form a 3-7-membered ring which optionally contains one further heteroatom;

provided that at least one of $R^1$, $R^2$, $R^3$, $R^4$, $R^5$, $R^6$, $R^7$, $R^8$, and $R^9$ is different from hydrogen; also provided that when $R^3$ is methyl, then at least one of $R^1$, $R^2$, $R^4$, $R^5$, $R^6$, $R^7$, $R^8$, $R^9$ is different from hydrogen; or a salt thereof.

In one embodiment of the compound of formula I, $R^1$ is selected from hydrogen, halogen, cyano, $C_{1-6}$-alk(en/yn)yl, $C_{1-6}$-alk(en/yn)yloxy, $C_{1-6}$-alk(en/yn)ylsulfanyl, halo-$C_{1-6}$-alk(en/yn)yl, or $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, or $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, or $C_{3-8}$-cycloalk(en)yl-$C_{1-6}$-alk(en/yn)yl, provided that if one of $R^x$ and $R^y$ is $NR^zR^w$-$C_{1-6}$-alk(en/yn)yl then the other is selected from hydrogen, $C_{1-6}$-alk(en/yn)yl, cyano-$C_{1-6}$-alk(en/yn)yl, $C_{3-8}$-cycloalk(en)yl, or $C_{3-8}$-cycloalk(en)yl-$C_{1-6}$alk(en/yn)yl; or $R^x$ and $R^y$ together with the nitrogen to which they are attached form a 3-7-membered ring which optionally contains one further heteroatom. In a further embodiment of the compound of formula I $R^1$ is selected from hydrogen, halogen, cyano, $C_{1-6}$-alk(en/yn)yl, $C_{1-6}$-alk(en/yn)yloxy, $C_{1-6}$-alk(en/yn)ylsulfanyl, halo-$C_{1-6}$-alk(en/yn)yl. In a further embodiment $R^1$ is $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, such as hydrogen, cyanomethyl, $C_{1-6}$-alk(en/yn)yl. In a further embodiment $R^1$ is $NR^xR^y$ wherein $R^x$ is $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, or $C_{3-8}$-cycloalk(en)yl-$C_{1-6}$-alk(en/yn)yl, and $R^y$ is selected from hydrogen, $C_{1-6}$alk(en/yn)yl, cyano-$C_{1-6}$-alk(en/yn)yl, $C_{3-8}$-cycloalk(en)yl, or $C_{3-8}$-cycloalk(en)yl-$C_{1-6}$-alk(en/yn)yl. In a further embodiment $R^1$ is $NR^xR^y$ wherein $R^x$ and $R^y$ together with the nitrogen to which they are attached form a 3-7-membered ring which optionally contains one further heteroatom, such as 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, optionally substituted with one or more selected from a $C_{1-6}$-alk(en/yn)yl, hydroxy, hydroxy-$C_{1-6}$-alk(en/yn)yl, $C_{1-6}$-alk(en/yn)yloxy-$C_{1-6}$-alk(en/yn)yl, e.g. one or two selected from hydroxy, hydroxy-$C_{1-6}$-alkyl, $C_{1-6}$-alkyloxy-$C_{1-6}$-alkyl, $C_{1-6}$-alkyl, in particular one or two selected from hydroxy, methoxy-methyl, methyl. Typically, $R^1$ is selected from hydrogen; halogen; cyano; $C_{1-6}$-alkyl; $C_{1-6}$-alkyloxy; $C_{1-6}$-alkylsulfanyl; halo-$C_{1-6}$-alkyl; $NR^xR^y$ wherein $R^x$ and $R^y$ are independently selected from hydrogen, $C_{1-6}$-alkyl, cyanomethyl; $NR^xR^y$ wherein $R^y$ is selected from hydrogen, or $C_{1-6}$-alkyl, and $R^x$ is $NR^zR^w$-$C_{1-6}$-alk(en/yn)yl wherein $R^z$ and $R^w$ are independently selected from hydrogen, or $C_{1-6}$-alkyl; 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, optionally substituted with one or two selected from hydroxy, hydroxy-$C_{1-6}$-alkyl, $C_{1-6}$-alkyloxy-$C_{1-6}$-alkyl, $C_{1-6}$-alkyl, in particular one or two selected from hydroxy, methoxy-methyl, methyl. To further illustrate without limiting the invention an embodiment of $R^1$ is hydrogen; another embodiment of $R^1$ is $C_{1-6}$-alkyl, such as methyl; a further embodiment of $R^1$ is halogen, such as fluoro, or chloro.

In a further embodiment of the compound of formula I, $R^2$ is selected from hydrogen, halogen, cyano, $C_{1-6}$-alk(en/yn)yl, $C_{1-4}$-alk(en/yn)yloxy, $C_{1-6}$-alk(en/yn)ylsulfanyl, halo-$C_{1-6}$ alk(en/yn)yl. Typically, $R^2$ is selected from hydrogen, halogen, cyano, $C_{1-6}$-alkyl, $C_{1-6}$-alkyloxy, $C_{1-6}$-alkylsulfanyl, halo-$C_{1-6}$-alkyl. To further illustrate without limiting the invention an embodiment of $R^2$ is hydrogen; another embodiment of $R^2$ is $C_{1-6}$-alkoxy, such as methoxy; a further embodiment of $R^2$ is halogen, such as fluoro, or chloro; a further embodiment of $R^2$ is $C_{1-6}$-alkyl, such as methyl.

In a further embodiment of the compound of formula I, $R^3$ is selected from hydrogen, halogen, cyano, $C_{1-6}$-alk(en/yn)yl, $C_{1-6}$-alk(en/yn)yloxy, $C_{1-6}$-alk(en/yn)ylsulfanyl, halo-$C_{1-6}$-alk(en/yn)yl. Typically, $R^3$ is selected from hydrogen, halogen, cyano, $C_{1-6}$-alkyl, $C_{1-6}$-alkyloxy, $C_{1-6}$-alkylsulfanyl, halo-$C_{1-6}$-alkyl. To further illustrate without limiting the invention an embodiment of $R^3$ is hydrogen; another embodiment of $R^3$ is $C_{1-6}$-alkyl, such as methyl; a further embodiment of $R^3$ is $C_{1-6}$-alkoxy, such as methoxy; a further embodiment of $R^3$ is halogen, such as bromo, chloro, or fluoro; a further embodiment of $R^3$ is halo-$C_{1-6}$-alkyl, such as $CF_3$; a further embodiment of $R^3$ is hydroxy-$C_{1-6}$-alkyl, such as hydroxy-methyl; a further embodiment of $R^3$ is $NR^xR^y$ wherein $R^x$ is hydrogen and $R^y$ is $C_{1-6}$-alkyl, such as methylamino; a further embodiment of $R^3$ is $C_{2-6}$-alkenyl, such as ethenyl.

In a further embodiment of the compound of formula I, $R^4$ is selected from hydrogen, halogen, cyano, $C_{1-6}$-alk(en/yn)yl, $C_{1-6}$-alk(en/yn)yloxy, $C_{1-6}$-alk(en/yn)ylsulfanyl, halo-$C_{1-6}$-alk(en/yn)yl. Typically, $R^4$ is selected from hydrogen, halogen, cyano, $C_{1-6}$-alkyl, $C_{1-6}$-akyloxy, $C_{1-6}$-alkylsulfanyl, halo-$C_{1-6}$-alkyl. To further illustrate without limiting the invention an embodiment of $R^4$ is hydrogen; another embodiment of $R^4$ is $C_{1-6}$-alkoxy, such as methoxy; a further embodiment of $R^4$ is halogen, such as fluoro, or chloro; a further embodiment of $R^4$ is $C_{1-6}$-alkyl, such as methyl.

In a further embodiment of the compound of formula I, $R^5$ is selected from hydrogen, halogen, cyano, $C_{1-6}$-alk(en/yn)yl, $C_{1-6}$-alk(en/yn)yloxy, $C_{1-6}$-alk(en/yn)ylsulfanyl, halo-$C_{1-6}$-alk(en/yn)yl, or $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, or $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, or $C_{3-8}$-cycloalk(en)yl-$C_{1-6}$-alk(en/yn)yl, provided that if one of $R^x$ and $R^y$ is $NR^zR^w$-$C_{1-6}$-alk(en/yn)yl then the other is selected from hydrogen, $C_{1-6}$-alk(en/yn)yl, cyano-$C_{1-6}$-alk(en/yn)yl, $C_{3-8}$-cycloalk(en)yl, or $C_{3-8}$-cycloalk(en)yl-$C_{1-6}$-alk(en/yn)yl; or $R^x$ and $R^y$ together with the nitrogen to which they are attached form a 3-7-membered ring which optionally contains one further heteroatom. In a further embodiment of the compound of formula I $R^5$ is selected from hydrogen, halogen, cyano, $C_{1-6}$-alk(en/yn)yl, $C_{1-6}$-alk(en/yn)yloxy, $C_{1-6}$-alk(en/yn)ylsulfanyl, halo-$C_{1-6}$ alk(en/yn)yl. In a further embodiment $R^5$ is $NR^xR^y$ wherein $R^x$ and $R^y$ are independently selected from hydrogen, $C_{1-6}$-alk(en/yn)yl, cyano-$C_{1-6}$alk(en/yn)yl, $C_{3-8}$-cycloalk(en)yl, $C_{3-8}$-cycloalk(en)yl-$C_{1-6}$-alk(en/yn)yl, such as hydrogen, cyanomethyl, $C_{1-6}$-alk(en/yn)yl. In a further embodiment $R^5$ is $NR^xR^y$ wherein $R^x$ is $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, or $C_{3-8}$-cycloalk(en)yl-$C_{1-6}$-alk(en/yn)yl, and $R^y$ is selected from hydrogen, $C_{1-6}$-alk(en/yn)yl, cyano-$C_{1-6}$-alk(en/yn)yl, $C_{3-8}$-cycloalk(en)yl, or $C_{3-8}$-cycloalk(en)yl-$C_{1-6}$-alk(en/yn)yl. In a further embodiment $R^5$ is $NR^xR^y$ wherein $R^x$ and $R^y$ together with the nitrogen to which they are attached form a 3-7-membered ring which optionally contains one further heteroatom, such as 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, optionally substituted with one or more selected from a $C_{1-6}$-alk(en/yn)yl, hydroxy, hydroxy-$C_{1-6}$-alk(en/yn)yl, $C_{1-6}$-alk(en/yn)yloxy-$C_{1-6}$-alk(en/yn)yl, e.g. one or two selected from hydroxy, hydroxy-$C_{1-6}$-alkyl, $C_{1-6}$-alkyloxy-$C_{1-6}$-alkyl, $C_{1-6}$-alkyl, in particular one or two selected from hydroxy, methoxy-methyl, methyl. Typically, $R^5$ is selected from hydrogen; halogen; cyano; $C_{1-6}$-alkyl; $C_{1-6}$-alkyloxy; $C_{1-6}$-alkylsulfanyl; halo-$C_{1-6}$-alkyl; $NR^xR^y$ wherein $R^x$ and $R^y$ are independently selected from hydrogen, $C_{1-6}$-alkyl, cyanomethyl; $NR^xR^y$ wherein $R^y$ is selected from hydrogen, or $C_{1-6}$-alkyl, and $R^x$ is $NR^zR^w$-$C_{1-6}$-alk(en/yn)yl wherein $R^z$ and $R^w$ are independently selected from hydrogen, or $C_{1-6}$-alkyl; 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, optionally substituted with one or two selected from hydroxy, hydroxy-$C_{1-6}$-alkyl, $C_{1-6}$-alkyloxy-$C_{1-6}$-alkyl, $C_{1-6}$-alkyl, in particular one or two selected from hydroxy, methoxy-methyl, methyl. To further illustrate without limiting the invention an embodiment of $R^5$ is hydrogen; another embodiment of $R^5$ is $C_{1-6}$-alkyl, such as methyl; a further embodiment of $R^5$ is halogen, such as chloro, or fluoro.

In a further embodiment of the compound of formula I, $R^6$ is selected from hydrogen, halogen, $C_{1-6}$-alk(en/yn)yl, halo-$C_{1-6}$-alk(en/yn)yl. Typically, $R^6$ is selected from hydrogen, halogen, $C_{1-6}$-alkyl, halo-$C_{1-6}$-alkyl. To further illustrate without limiting the invention an embodiment of $R^6$ is hydrogen; another embodiment of $R^6$ is halogen, such as fluoro.

In a further embodiment of the compound of formula I, $R^7$ is selected from hydrogen, halogen, $C_{1-6}$-alk(en/yn)yl, halo-$C_{1-6}$-alk(en/yn)yl. Typically, $R^7$ is selected from hydrogen, halogen, $C_{1-6}$-alkyl, halo-$C_{1-6}$-alkyl. To further illustrate without limiting the invention an embodiment of $R^7$ is hydrogen; another embodiment of $R^7$ is halogen, such as fluoro.

In a further embodiment of the compound of formula I, $R^8$ is selected from hydrogen, halogen, $C_{1-6}$-alk(en/yn)yl, halo-$C_{1-6}$-alk(en/yn)yl, or $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, or $NR^zR^w$-$C_{1-6}$alk(en/yn)yl, wherein $R^z$ and $R^w$ are independently selected from hydrogen, $C_{1-6}$alk(en/yn)yl, $C_{3-8}$-cycloalk(en)yl, or $C_{3-8}$-cycloalk(en)yl-$C_{1-6}$-alk(en/yn)yl, provided that if one of $R^x$ and $R^y$ is $NR^zR^w$-$C_{1-6}$-alk(en/yn)yl then the other is selected from hydrogen, $C_{1-6}$-alk(en/yn)yl, cyano-$C_{1-6}$-alk(en/yn)yl, $C_{3-8}$-cycloalk(en)yl, or $C_{3-8}$-cycloalk(en)yl-$C_{1-6}$-alk(en/yn)yl; or $R^x$ and $R^y$ together with the nitrogen to which they are attached form a 3-7-membered ring which optionally contains one further heteroatom. In a further embodiment of the compound of formula I, $R^8$ is selected from hydrogen, halogen, $C_{1-6}$-alk(en/yn)yl, halo-$C_{1-6}$-alk(en/yn)yl. In a further embodiment, $R^8$ is $NR^xR^y$ wherein $R^x$ and $R^y$ are independently selected from hydrogen, $C_{1-6}$-alk(en/yn)yl, cyano-$C_{1-6}$-alk(en/yn)yl, $C_{3-8}$-cycloalk(en)yl, $C_{3-8}$-cycloalk(en)yl-$C_{1-6}$-alk(en/yn)yl, such as hydrogen, cyanomethyl, $C_{1-6}$-alk(en/yn)yl. In a further embodiment, $R^8$ is $NR^xR^y$ wherein $R^x$ is $NR^zR^w$-$C_{1-6}$-alk(en/yn)yl, wherein $R^z$ and $R^w$ are independently selected from hydrogen, $C_{1-6}$-alk(en/yn)yl, $C_{3-8}$-cycloalk(en)yl, or $C_{3-8}$-cycloalk(en)yl-$C_{1-6}$-alk(en/yn)yl, and $R^y$ is selected from hydrogen, $C_{1-6}$-alk(en/yn)yl, cyano-$C_{1-6}$-alk(en/yn)yl, $C_{3-8}$-cycloalk(en)yl, or $C_{3-8}$-cycloalk(en)yl-$C_{1-6}$alk(en/yn)yl. In a further embodiment, $R^8$ is $NR^xR^y$ wherein $R^x$ and $R^y$ together with the nitrogen to which they are attached form a 3-7-membered ring which optionally contains one further heteroatom, such as 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, optionally substituted with one or more selected from a $C_{1-6}$-alk(en/yn)yl, hydroxy, hydroxy-$C_{1-6}$-alk(en/yn)yl, $C_{1-6}$-alk(en/yn)yloxy-$C_{1-6}$-alk(en/yn)yl, e.g. one or two selected from hydroxy, hydroxy-$C_{1-6}$-alkyl, $C_{1-6}$-alkyloxy-$C_{1-6}$-alkyl, $C_{1-6}$-alkyl, in particular one or two selected from hydroxy, methoxy-methyl, methyl. Typically, $R^8$ is selected from hydrogen; halogen; cyano; $C_{1-6}$-alkyl; $C_{1-6}$-alkyloxy; $C_{1-6}$-alkylsulfanyl; halo-$C_{1-6}$-alkyl; $NR^xR^y$ wherein $R^x$ and $R^y$ are independently selected from hydrogen, $C_{1-6}$-alkyl, cyanomethyl; $NR^xR^y$ wherein $R^y$ is selected from hydrogen, or $C_{1-6}$-alkyl, and $R^x$ is $NR^zR^w$-$C_{1-6}$-alk(en/yn)yl wherein $R^z$ and $R^w$ are independently selected from hydrogen, or $C_{1-6}$-alkyl; 1-morpholinyl, 1-piperidinyl, 1-azepinyl, 1-piperazinyl, 1-homopiperazinyl, 1-imidazolyl, 1-pyrrolidinyl, 1-azetidinyl, 1-pyrrolyl or pyrazolyl, optionally substituted with one or two selected from hydroxy, hydroxy-$C_{1-6}$-alkyl, $C_{1-6}$-alkyloxy-$C_{1-6}$-alkyl, $C_{1-6}$-alkyl, in particular one or two selected from hydroxy, methoxy-methyl, methyl. To further illustrate without limiting the invention an embodiment of $R^8$ is hydrogen; another embodiment of $R^8$ is halogen, such as fluoro, or bromo; a further embodiment of $R^8$ is $C_{1-6}$-alkyl, such as methyl; another embodiment of $R^8$ is $C_{1-6}$-alkyloxy, such as methoxy; a further embodiment of $R^8$ is halo-$C_{1-6}$-alkyl, such as $CF_3$.

In a further embodiment of the compound of formula I, $R^9$ is selected from hydrogen, halogen, $C_{1-6}$-alk(en/yn)yl, halo-$C_{1-6}$-alk(en/yn)yl. Typically, $R^9$ is selected from hydrogen, halogen, $C_{1-6}$-alkyl, halo-$C_{1-6}$-alkyl. To further illustrate without limiting the invention an embodiment of $R^9$ is hydrogen; another embodiment of $R^9$ is halogen, such as fluoro.

Typically, the compound of formula I has at least one substituent in the phenyl ring(s), selected from any one of $R^1$-$R^9$, which is different from hydrogen, such as 1, 2, 3, or 4 substituents in the phenyl ring(s), selected from any one of $R^1$-$R^9$, which is/are different from hydrogen, and the remaining substituents are hydrogen. Thus, in a further embodiment 1 substituent selected from any one of $R^1$-$R^9$, which is different from hydrogen, is present in either of the two phenyl rings, such as 1 substituent selected from $R^1$-$R^5$, or the substituent is selected from $R^6$-$R^9$. In a further embodiment, 2 substituents selected from $R^1$-$R^9$, which are different from hydrogen, are present in either of the two phenyl rings, such as 1 substituent selected from $R^1$-$R^5$, and the other selected from $R^6$-$R^9$, or both substituents are selected from $R^1$-$R^5$. In a further embodiment, 3 substituents selected from $R^1$-$R^9$, which are different from hydrogen, are present in either of the two phenyl rings, such as 2 substituents selected from $R^1$-$R^5$, and the last substituent is selected from $R^6$-$R^9$. In each embodiment, as mentioned the remaining substituents are hydrogen. To illustrate this further without limiting the invention, some typical embodiments are outlined hereafter.

Thus, in a further embodiment of the compound of formula I one substituent is present which is $R^2$ as defined above, except hydrogen. In a further embodiment of the compound of formula I, one substituent is present which is $R^3$ as defined above, except hydrogen. In a further embodiment of the compound of formula I, two substituents are present being $R^3$ and $R^8$, wherein $R^3$ and $R^8$ are as defined above, except hydrogen. In a further embodiment of the compound of formula I, two substituents are present being $R^3$ and $R^6$, wherein $R^3$ and $R^6$ are as defined above, except hydrogen. In a further embodiment of the compound of formula I, two substituents are present being $R^3$ and $R^7$, wherein $R^3$ and $R^7$ are as defined above, except hydrogen. In a further embodiment of the compound of formula I, two substituents are present being $R^1$ and $R^3$, wherein $R^1$ and $R^3$ are as defined above, except hydrogen. In a further embodiment of the compound of formula I, two substituents are present being $R^2$ and $R^3$, wherein $R^2$ and $R^3$ are as defined above, except hydrogen. In a further embodiment of the compound of formula I, three substituents are present being $R^1$, $R^3$ and $R^8$, wherein $R^1$, $R^3$ and $R^8$ are as defined above, except hydrogen. In each embodiment, as mentioned above the remaining substituents are hydrogen.

In a further embodiment of the compound of formula I, said compound is selected from 4-[2-(4-Chloro-phenylsulfanyl)-5-trifluoromethyl-phenyl]-piperidine 4-[2-(4-Methoxy-phenylsulfanyl)-phenyl]-piperidine 4-[2-(2,4-Dimethyl-phenylsulfanyl)-5-trifluoromethyl-phenyl]-piperidine 4-[2-(4-Chloro-phenylsulfanyl)-4-fluoro-phenyl]-piperidine 4-[2-(4-Methoxy-phenylsulfanyl)-4-fluoro-phenyl]-piperidine 4-[2-(4-Methyl-phenylsulfanyl)-5-methyl-phenyl]-piperidine 4-[2-(2,4-Dimethyl-phenylsulfanyl)-5-methyl-phenyl]-piperidine 4-[2-(4-Fluoro-2-methyl-phenylsulfanyl)-5-methyl-phenyl]-piperidine 4-[2-(4-Methoxy-phenylsulfanyl)-5-methyl-phenyl]-piperidine 4-[2-(4-Chloro-2-methyl-phenylsulfanyl)-phenyl]-piperidine 4-[2-(4-Chloro-2-fluoro-phenylsulfanyl)-phenyl]-piperidine 4-[2-(2,4-Dichloro-phenylsulfanyl)-phenyl]-piperidine 4-[2-(2-Chloro-4-methoxy-phenylsulfanyl)-phenyl]-piperidine 4-[2-(4-Chloro-phenylsulfanyl)-phenyl-piperidine 4-[2-(4-Methoxy-phenylsulfanyl)-5-fluoro-phenyl]-piperidine 4-[2-(4-Chloro-phenylsulfanyl)-5-fluoro-phenyl]-piperidine 4-[2-(4-Methoxy-phenylsulfanyl)-3-fluoro-phenyl]-piperidine 4-[2-(2,4-Dimethyl-phenylsulfanyl)-5-bromo-phenyl]-piperidine 4-[2-(4-Methyl-phenylsulfanyl)-4-fluoro-phenyl]-piperidine 4-[2-(4-Chloro-phenylsulfanyl)-5-methyl-phenyl]-piperidine 4-[2-(4-Methyl-phenylsulfanyl)-5-trifluoromethyl-phenyl]-piperidine 4-[2-(2,4-Dimethyl-phenylsulfanyl)-5-fluoro-phenyl]-piperidine 4-[2-(4-Fluoro-phenylsulfanyl)-5-fluoro-phenyl]-piperidine 4-[2-(2-Chloro-4-fluoro-phenylsulfanyl)-5-fluoro-phenyl]-piperidine
4-[2-(4-Methyl-4-phenylsulfanyl)-5-fluoro-phenyl]-piperidine
4-[2-(3-Methoxy-phenylsulfanyl)-5-fluoro-phenyl]-piperidine
4-[2-(2-Chloro-4-methyl-phenylsulfanyl)-5-fluoro-phenyl]-piperidine
4-[2-(2-Chloro-4-methoxy-phenylsulfanyl)-5-fluoro-phenyl]-piperidine
4-[2-(4-Chloro-2-fluoro-phenylsulfanyl)-5-fluoro-phenyl]-piperidine
4-[2-(2-Fluoro-4-methyl-phenylsulfanyl)-5-fluoro-phenyl]-piperidine
4-[2-(2-Chloro-phenylsulfanyl)-5-fluoro-phenyl]-piperidine
4-[2-(2,4-Dichloro-phenylsulfanyl)-5-fluoro-phenyl]-piperidine
4-[2-(2,4-Difluoro-phenylsulfanyl)-5-fluoro-phenyl]-piperidine
4-[2-(2,4-Dimethyl-phenylsulfanyl)-3-fluoro-phenyl]-piperidine
4-[2-(Phenylsulfanyl)-5-fluoro-phenyl]-piperidine
4-[2-(4-Bromo-2-fluoro-phenylsulfanyl)-5-fluoro-phenyl]-piperidine
4-[2-(3-Chloro-phenylsulfanyl)-5-fluoro-phenyl]-piperidine
4-[2-(3-Fluoro-phenylsulfanyl)-5-fluoro-phenyl]-piperidine
4-[2-(2-Fluoro-4-methoxy-phenylsulfanyl)-5-fluoro-phenyl]-piperidine
4-[2-(2-Methyl-4-methoxy-phenylsulfanyl)-5-fluoro-phenyl]-piperidine
4-[2-(2-Methyl-phenylsulfanyl)-5-fluoro-phenyl]-piperidine
4-[2-(2-Fluoro-phenylsulfanyl)-5-fluoro-phenyl]-piperidine
4-[2-(4-Trifluoromethyl-phenylsulfanyl)-phenyl]-
4-[2-(2-Chloro-4-fluoro-phenylsulfanyl)-phenyl]-piperidine
4-[2-(4-Methoxy-2-methyl-phenylsulfanyl)-phenyl]-piperidine
4-[2-(2,4-Difluoro-phenylsulfanyl)-phenyl]-piperidine
4-[2-(2,3-Dimethyl-phenylsulfanyl)-phenyl]-piperidine
4-[2-(3,4-Dimethyl-phenylsulfanyl)-phenyl]-piperidine
4-[2-(2-Chloro-4-methoxy-phenylsulfanyl)-5-methyl-phenyl]-piperidine
4-[2-(2-Chloro-4-methyl-phenylsulfanyl)-5-methyl-phenyl]-piperidine
4-[2-(2-Fluoro-4-methyl-phenylsulfanyl)-5-methyl-phenyl]-piperidine
4-[2-(4-Fluoro-3-methoxy-phenylsulfanyl)-5-methyl-phenyl]-piperidine
4-[2-(3-Fluoro-2-methyl-phenylsulfanyl)-5-methyl-phenyl]-piperidine
4-[2-(3-Fluoro-4-methyl-phenylsulfanyl)-5-methyl-phenyl]-piperidine
4-[2-(5-Chloro-2-fluoro-phenylsulfanyl)-5-methyl-phenyl]-piperidine
4-[2-(2-Chloro-4-fluoro-phenylsulfanyl)-5-methyl-phenyl]-piperidine
4-[2-(3-Methoxy-phenylsulfanyl)-5-methyl-phenyl]-piperidine
4-[2-(4-Chloro-2-fluoro-phenylsulfanyl)-5-methyl-phenyl]-piperidine
4-[2-(3-Chloro-2-fluoro-phenylsulfanyl)-5-methyl-phenyl]-piperidine
4-[2-(2,4-Difluoro-phenylsulfanyl)-5-methyl-phenyl]-piperidine
4-[2-(4-Methyl-phenylsulfanyl)-5-methoxy-phenyl]-piperidine
4-[2-(4-Fluoro-phenylsulfanyl)-5-methoxy-phenyl]-piperidine
4-[2-(2-Methyl-4-methoxy-phenylsulfanyl)-5-methoxy-phenyl]-piperidine
4-[2-(4-Fluoro-2-methyl-phenylsulfanyl)-5-methoxy-phenyl]-piperidine
4-[2-(3-Methoxy-phenylsulfanyl)-6-fluoro-phenyl]-piperidine
4-[2-(2-Methyl-phenylsulfanyl)-6-fluoro-phenyl]-piperidine
4-[2-(3-Methyl-phenylsulfanyl)-6-fluoro-phenyl]-piperidine
4-[2-(4-Methoxy-2-methyl-phenylsulfanyl)-6-fluoro-phenyl]-piperidine
4-[2-(2-Methoxy-phenylsulfanyl)-6-fluoro-phenyl]-piperidine
4-[2-(4-Fluoro-2-Methyl-phenylsulfanyl)-6-fluoro-phenyl]-piperidine
4-[2-(3-Fluoro-4-methyl-phenylsulfanyl)-6-fluoro-phenyl]-piperidine
4-[2-(2,3-Dimethyl-phenylsulfanyl)-6-fluoro-phenyl]-piperidine
4-[2-(3-Fluoro-2-methyl-phenylsulfanyl)-6-fluoro-phenyl]-piperidine
4-[2-(3-Chloro-phenylsulfanyl)-6-fluoro-phenyl]-piperidine
4-[2-(3-Fluoro-phenylsulfanyl)-6-fluoro-phenyl]-piperidine
4-[2-(2-Fluoro-phenylsulfanyl)-6-fluoro-phenyl]-piperidine
4-[2-(4-Fluoro-3-methoxy-phenylsulfanyl)-6-fluoro-phenyl]-piperidine
4-[2-(2-Chloro-4-methyl-phenylsulfanyl)-6-fluoro-phenyl]-piperidine
4-[2-(4-Chloro-2-fluoro-phenylsulfanyl)-6-fluoro-phenyl]-piperidine
4-[2-(4-Trifluoromethyl-phenylsulfanyl)-6-fluoro-phenyl]-piperidine
4-[2-(3-Chloro-2-fluoro-phenylsulfanyl)-6-fluoro-phenyl]-piperidine
4-[2-(4-Methyl-phenylsulfanyl)-6-fluoro-phenyl]-piperidine
4-[2-(4-Chloro-phenylsulfanyl)-6-fluoro-phenyl]-piperidine
4-[2-(3,4-Dimethyl-phenylsulfanyl)-6-fluoro-phenyl]-piperidine
4-[2-(2-Fluoro-4-methyl-phenylsulfanyl)-6-fluoro-phenyl]-piperidine
4-[2-(2,4-Dichloro-phenylsulfanyl)-6-fluoro-phenyl]-piperidine
4-[2-(2-Fluoro-4-methoxy-phenylsulfanyl)-6-fluoro-phenyl]-piperidine
4-[2-(2,4-Difluoro-phenylsulfanyl)-6-fluoro-phenyl]-piperidine
4-[2-(2-Chloro-4-methoxy-phenylsulfanyl)-6-fluoro-phenyl]-piperidine
4-[2-(4-Methoxy-phenylsulfanyl)-6-fluoro-phenyl]-piperidine
4-[2-(4-Fluoro-phenylsulfanyl)-6-fluoro-phenyl]-piperidine
4-[2-(2,3-Dichloro-phenylsulfanyl)-5-fluoro-phenyl]-piperidine
4-[2-(2-Methoxy-phenylsulfanyl)-5-fluoro-phenyl]-piperidine
4-[2-(4-Trifluoromethoxy-phenylsulfanyl)-5-fluoro-phenyl]-piperidine
4-[2-(4-Fluoro-2-methyl-phenylsulfanyl)-5-fluoro-phenyl]-piperidine
4-[2-(4-Trifluoromethyl-phenylsulfanyl)-5-fluoro-phenyl]-piperidine
4-[2-(3-Methyl-phenylsulfanyl)-5-fluoro-phenyl]-piperidine
4-[2-(4-Chloro-2-methyl-phenylsulfanyl)-5-fluoro-phenyl]-piperidine
4-[2-(2,3-Dimethyl-phenylsulfanyl)-5-fluoro-phenyl]-piperidine
4-[2-(2,3-Dihydro-benzo[1,4]dioxin-6-ylsulfanyl)-5-fluoro-phenyl]-piperidine 4-[2-(4-Fluoro-3-methoxy-phenylsulfanyl)-5-fluoro-phenyl]-piperidine
4-[2-(2-Methyl-phenylsulfanyl)-4-fluoro-phenyl]-piperidine
4-[2-(2-Chloro-phenylsulfanyl)-4-fluoro-phenyl]-piperidine
4-[2-(4-Fluoro-phenylsulfanyl)-4-fluoro-phenyl]-piperidine
4-[2-(3,4-Dimethyl-phenylsulfanyl)-4-fluoro-phenyl]-piperidine
4-[2-(2-Chloro-4-Methyl-phenylsulfanyl)-4-fluoro-phenyl]-piperidine
4-[2-(2-Fluoro-4-methyl-phenylsulfanyl)-4-fluoro-phenyl]-piperidine
4-[2-(5-Chloro-2-fluoro-phenylsulfanyl)-4-fluoro-phenyl]-piperidine
4-[2-(2-Chloro-4-fluoro-phenylsulfanyl)-4-fluoro-phenyl]-piperidine
4-[2-(2,3-Dimethyl-phenylsulfanyl)-4-fluoro-phenyl]-piperidine
4-[2-(3-Fluoro-2-methyl-phenylsulfanyl)-4-fluoro-phenyl]-piperidine
4-[2-(4-Methoxy-2-methyl-phenylsulfanyl)-4-fluoro-phenyl]-piperidine
4-[2-(3-Fluoro-4-methyl-phenylsulfanyl)-4-fluoro-phenyl]-piperidine
4-[2-(4-Fluoro-2-methyl-phenylsulfanyl)-4-fluoro-phenyl]-piperidine
4-[2-(4-Hydroxymethyl-phenylsulfanyl)-phenyl]-piperidine
4-[2-(2-Fluoro-4-methyl-amine-phenylsulfanyl)-5-fluorophenyl]-piperidine
4-[2-(2-Fluoro-4-vinyl-phenylsulfanyl)-5-fluorophenyl]-piperidine, or a pharmaceutically acceptable salt thereof. Each of these compounds is considered a specific embodiment and may be subject to individual claims.

As mentioned above, the present compounds of formula I are serotonin reuptake inhibitors. Some of the tested compounds have also shown good affinity to the $5HT_{2C}$ receptor, typically Ki<75 nM as measured in the test described in the examples section, and such compounds are considered to be further aspects of the invention. Accordingly, in a further aspect the present invention relates to a compound of formula I or a salt thereof, wherein $R^3$ is selected from $C_{1-6}$ alkoxy (such as methoxy), halogen (such as Cl), or halo-$C_{1-6}$ alkyl (such as $CF_3$), and $R^1$, $R^2$, and $R^4$—$R^9$ are all hydrogen. In a still further aspect, the present invention relates to a compound of formula I or a salt thereof, wherein $R^1$ is selected from halogen (such as Cl or F), and $R^3$ is selected from halogen (such as F), and $R^2$, and $R^4$—$R^9$ are all hydrogen. In a still further aspect, the present invention relates to a compound of formula I or a salt thereof, wherein $R^1$ is selected from halogen (such as Cl), and $R^7$ is selected from halogen (such as F), and $R^2$—$R^6$ and $R^8$—$R^9$ are all hydrogen. In a still further aspect, the present invention relates to a compound of formula I or a salt thereof, wherein $R^3$ is selected from halogen (such as F), and $R^7$ is selected from halogen (such as F), and $R^1$—$R^2$, $R^4$—$R^6$ and $R^8$—$R^9$ are all hydrogen. In a still further aspect, the present invention relates to a compound of formula I or a salt thereof, wherein $R^1$ is selected from halogen (such as F), and $R^9$ is selected from halogen (such as F), and $R^2$—$R^8$, are all hydrogen. In a still further aspect, the present invention relates to a compound of formula I or a salt thereof, wherein $R^2$ is selected from halogen (such as Cl or F), and $R^9$ is selected from halogen (such as F), and $R^1$ and $R^3$—$R^8$, are all hydrogen. In a still further aspect, the present invention relates to a compound of formula I or a salt thereof, wherein $R^3$ is selected from $C_{1-6}$ alkyl (such as methyl), $C_{1-6}$ alkoxy (such as methoxy), or halogen (such as Cl or F), and $R^9$ is selected from halogen (such as F), and $R^1$, $R^2$, and $R^4$—$R^8$, are all hydrogen. In a still further aspect, the present invention relates to a compound of formula I or a salt thereof, wherein $R^3$ is selected from $C_{1-6}$ alkoxy (such as methoxy), and $R^6$ is selected from halogen (such as F), and $R^1$, $R^2$, $R^4$, $R^5$, and $R^7$—$R^9$ are all hydrogen. In a still further aspect, the present invention relates to a compound of formula I or a salt thereof, wherein $R^3$ is selected from $C_{1-6}$ alkoxy (such as methoxy), or halogen (such as Cl), and $R^7$ is selected from halogen (such as F), and $R^1$, $R^2$, $R^4$—$R^6$, and $R^8$—$R^9$ are all hydrogen. In a still further aspect, the present invention relates to a compound of formula I or a salt thereof, wherein $R^3$ is selected from $C_{1-6}$ alkyl (such as methyl), $C_{1-6}$ alkoxy (such as methoxy), or halogen (such as F or Cl), and $R^8$ is selected from $C_{1-6}$ alkyl (such as methyl), $C_{1-6}$ alkoxy (such as methoxy), or halogen (such as F), and $R^1$, $R^2$, $R^4$—$R^7$, and $R^9$ are all hydrogen. In a still further aspect, the present invention relates to a compound of formula I or a salt thereof, wherein $R^1$ is selected from $C_{1-6}$ alkyl (such as methyl), $R^3$ is selected from $C_{1-6}$ alkyl (such as methyl), and $R^6$ is selected from halogen (such as F), and $R^2$, $R^4$—$R^5$, and $R^7$—$R^9$ are all hydrogen. In a still further aspect, the present invention relates to a compound of formula I or a salt thereof, wherein $R^1$ is selected from $C_{1-6}$ alkyl (such as methyl), or halogen (such as F), $R^3$ is selected from $C_{1-6}$ alkoxy (such as methoxy), or halogen (such as F, Br, or Cl), and $R^5$ is selected from $C_{1-6}$ alkyl (such as methyl), or halogen (such as F), and $R^2$, $R^4$—$R^7$, and $R^9$ are all hydrogen. In a still further aspect, the present invention relates to a compound of formula I or a salt thereof, wherein $R^1$ is selected from $C_{1-6}$ alkyl (such as methyl), or halogen (such as F or Cl), $R^3$ is selected from $C_{1-6}$ alkyl (such as methyl), $C_{1-6}$ alkoxy (such as methoxy), or halogen (such as F, or Cl), and $R^9$ is selected from halogen (such as F), and $R^2$, and $R^4$—$R^8$, are all hydrogen. In a still further aspect, the present invention relates to a compound of formula I or a salt thereof, wherein $R^1$ is selected from halogen (such as F), $R^2$ is selected from halogen (such as Cl), and $R^9$ is selected from halogen (such as F), and $R^3$, and $R^4$—$R^8$, are all hydrogen. In a still further aspect, the present invention relates to a compound of formula I or a salt thereof, wherein $R^2$ is selected from $C_{1-6}$ alkoxy (such as methoxy), or halogen (such as F), $R^3$ is selected from halogen (such as F), or $C_{1-6}$-alkyl (such as methyl), and $R^9$ is selected from halogen (such as F), and $R^1$, and $R^4$—$R^8$, are all hydrogen. Preferred compounds which are serotonin reuptake inhibitors and has shown good affinity to the $5HT_{2C}$ receptor are selected from:

4-[2-(4-Methoxy-phenylsulfanyl)-phenyl]-piperidine
4-[2-(4-Chloro-phenylsulfanyl)-4-fluoro-phenyl]-piperidine
4-[2-(4-Methoxy-phenylsulfanyl)-4-fluoro-phenyl]-piperidine
4-[2-(4-Methyl-phenylsulfanyl)-5-methyl-phenyl]-piperidine
4-[2-(4-Fluoro-2-methyl-phenylsulfanyl)-5-methyl-phenyl]-piperidine
4-[2-(4-Methoxy-phenylsulfanyl)-5-methyl-phenyl]-piperidine
4-[2-(4-Chloro-phenylsulfanyl)-phenyl-piperidine
4-[2-(4-Methoxy-phenylsulfanyl)-5-fluoro-phenyl]-piperidine
4-[2-(4-Methoxy-phenylsulfanyl)-3-fluoro-phenyl]-piperidine
4-[2-(4-Chloro-phenylsulfanyl)-5-methyl-phenyl]-piperidine
4-[2-(4-Fluoro-phenylsulfanyl)-5-fluoro-phenyl]-piperidine
4-[2-(4-Chloro-2-fluoro-phenylsulfanyl)-5-fluoro-phenyl]-piperidine 4-[2-(2-Fluoro-4-methyl-phenylsulfanyl)-5-fluoro-phenyl]-piperidine
4-[2-(2,4-Difluoro-phenylsulfanyl)-5-fluoro-phenyl]-piperidine
4-[2-(2,4-Dimethyl-phenylsulfanyl)-3-fluoro-phenyl]-piperidine
4-[2-(4-Bromo-2-fluoro-phenylsulfanyl)-5-fluoro-phenyl]-piperidine
4-[2-(2-Fluoro-4-methoxy-phenylsulfanyl)-5-fluoro-phenyl]-piperidine
4-[2-(2-Chloro-4-fluoro-phenylsulfanyl)-phenyl]-piperidine
4-[2-(2,4-Difluoro-phenylsulfanyl)-phenyl]-piperidine
4-[2-(4-Fluoro-phenylsulfanyl)-5-methoxy-phenyl]-piperidine
4-[2-(4-Methoxy-2-methyl-phenylsulfanyl)-6-fluoro-phenyl]-piperidine
4-[2-(3-Fluoro-4-methyl-phenylsulfanyl)-6-fluoro-phenyl]-piperidine
4-[2-(3-Chloro-phenylsulfanyl)-6-fluoro-phenyl]-piperidine
4-[2-(3-Fluoro-phenylsulfanyl)-6-fluoro-phenyl]-piperidine
4-[2-(2-Fluoro-phenylsulfanyl)-6-fluoro-phenyl]-piperidine
4-[2-(4-Fluoro-3-methoxy-phenylsulfanyl)-6-fluoro-phenyl]-piperidine
4-[2-(4-Chloro-2-fluoro-phenylsulfanyl)-6-fluoro-phenyl]-piperidine
4-[2-(4-Trifluoromethyl-phenylsulfanyl)-6-fluoro-phenyl]-piperidine
4-[2-(3-Chloro-2-fluoro-phenylsulfanyl)-6-fluoro-phenyl]-piperidine
4-[2-(4-Methyl-phenylsulfanyl)-6-fluoro-phenyl]-piperidine
4-[2-(4-Chloro-phenylsulfanyl)-6-fluoro-phenyl]-piperidine
4-[2-(2-Fluoro-4-methyl-phenylsulfanyl)-6-fluoro-phenyl]-piperidine
4-[2-(2-Fluoro-4-methoxy-phenylsulfanyl)-6-fluoro-phenyl]-piperidine
4-[2-(2,4-Difluoro-phenylsulfanyl)-6-fluoro-phenyl]-piperidine
4-[2-(2-Chloro-4-methoxy-phenylsulfanyl)-6-fluoro-phenyl]-piperidine
4-[2-(4-Methoxy-phenylsulfanyl)-6-fluoro-phenyl]-piperidine
4-[2-(4-Fluoro-phenylsulfanyl)-6-fluoro-phenyl]-piperidine
4-[2-(2-Chloro-phenylsulfanyl)-4-fluoro-phenyl]-piperidine
4-[2-(4-Fluoro-phenylsulfanyl)-4-fluoro-phenyl]-piperidine, or a pharmaceutically acceptable salt thereof.

The present invention also comprises salts of the present compounds, typically, pharmaceutically acceptable salts. Such salts include pharmaceutical acceptable acid addition salts, pharmaceutically acceptable metal salts, ammonium and alkylated ammonium salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any optical isomers (i.e. enantiomers or diastereomers), as separated, pure or partially purified optical isomers and any mixtures thereof including racemic mixtures are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization of d- or l-(tartrates, mandelates or camphorsulphonate) salts. The compounds of the present invention may also be resolved by the formation of diastereomeric derivatives.

Additional methods for the resolution of optical isomers, known to those skilled in the art, may be used. Such methods include those discussed by Collet and Wilen in the textbook *Enantiomers, Racemates, and Resolutions*, John Wiley and Sons, New York (1981).

Optically active compounds can also be prepared from optically active starting materials, or by stereo selective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in the textbook *Design of Prodrugs*, ed. H. Bundgaard, Elsevier, 1985.

The invention also encompasses active metabolites of the present compounds.

As mentioned above, the compounds of formula I are serotonin reuptake inhibitors, and accordingly may be applicable for the treatment, including prevention, of affective disorders, such as depression, anxiety disorders including general anxiety disorder and panic disorder and obsessive compulsive disorder.

Accordingly, in a further aspect the invention relates to a compound of formula I for use as a medicament.

The present invention also relates to a pharmaceutical composition comprising a compound of formula I and a pharmaceutically acceptable carrier or diluent. The composition may comprise any one of the embodiments of formula I described above.

In an embodiment of the pharmaceutical composition, the compound of formula I is present in an amount of from about 0.001 to about 100 mg/kg body weight per day.

The present invention also relates to use of a compound of formula I for the preparation of a medicament for the treatment of a disease or disorder, wherein a serotonin reuptake inhibitor is beneficial. The medicament may comprise any one of the embodiments of formula I described above.

In particular, the present invention also relates to use of a compound of formula I for the preparation of a medicament for the treatment of affective disorders.

In a further embodiment, the present invention also relates to use of a compound of formula I for the preparation of a medicament for the treatment of depression.

In a further embodiment, the present invention also relates to use of a compound of formula I for the preparation of a medicament for the treatment of anxiety disorders.

In a further embodiment, the present invention also relates to use of a compound of formula I for the preparation of a medicament for the treatment of general anxiety disorder.

In a further embodiment, the present invention also relates to use of a compound of formula I for the preparation of a medicament for the treatment of social anxiety disorder.

In a further embodiment, the present invention also relates to use of a compound of formula I for the preparation of a medicament for the treatment of post traumatic stress disorder.

In a further embodiment, the present invention also relates to use of a compound of formula I for the preparation of a medicament for the treatment of obsessive compulsive disorder.

In a further embodiment, the present invention also relates to use of a compound of formula I for the preparation of a medicament for the treatment of panic disorder.

In a further embodiment, the present invention also relates to use of a compound of formula I for the preparation of a medicament for the treatment of panic attacks.

In a further embodiment, the present invention also relates to use of a compound of formula I for the preparation of a medicament for the treatment of specific phobias.

In a further embodiment, the present invention also relates to use of a compound of formula I for the preparation of a medicament for the treatment of social phobia.

In a further embodiment, the present invention also relates to use of a compound of formula I for the preparation of a medicament for the treatment of agoraphobia.

A further aspect of the invention relates to a method for the treatment of a disease or disorder selected from the group consisting of an affective disorder, such as depression, anxiety disorders including general anxiety disorder, social anxiety disorder, post traumatic stress disorder, obsessive compulsive disorder, panic disorder, panic attacks, specific phobias, social phobia and agoraphobia in a living animal body, including a human, comprising administering to a subject in need thereof a therapeutically effective amount of a compound of formula I.

In a further aspect, the present invention relates to a method of preparing a compound of formula I, comprising a) Deprotection or cleavage from a polymer support of a compound with formula II

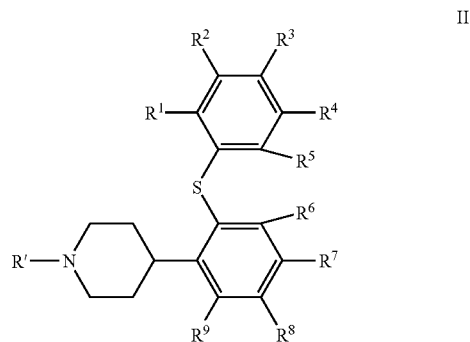

wherein $R^1$—$R^9$ are as previously described, and R is a carbamate (such as methyl-, ethyl-, tert-butyl-, alkyl-, or benzyl-carbamate) or a benzyl-derived protective group, wherein the protective groups may be linked to a solid support, for example the Wang resin-based carbamate linker; or b) Chemical transformation of a compound with formula III to the corresponding diazonium compound and subsequent reaction with a thiophenol of formula IV

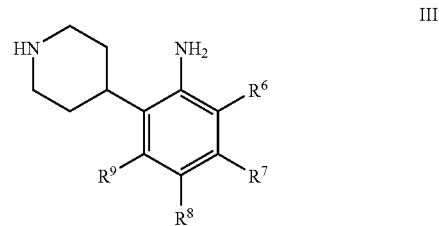

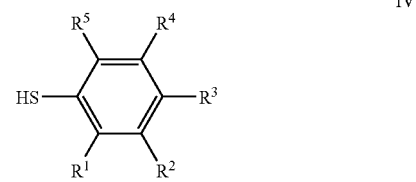

wherein $R^1$—$R^9$ are as previously described; or c) Reacting a compound of formula V with a thiophenol of formula IV in the presence of a palladium or copper catalyst

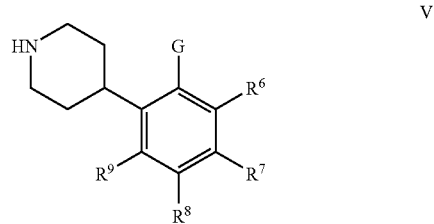

-continued

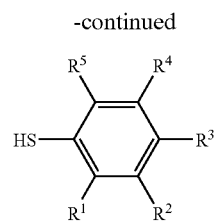

IV wherein $R^1$—$R^9$ are as previously described, and G is a chlorine, bromine, or iodine atom or a sulfonyl ester, wherein the sulfonyl ester is derived from the corresponding phenol by reaction with 4-methyl-benzenesulfonyl chloride, trifluoromethanesulfonic acid anhydride, 1,1,2,2,3,3,4,4,4-nonafluoro-butane-1-sulfonyl fluoride, or related compounds; or d) Hydrogenate the double bond in a compound of formula VI

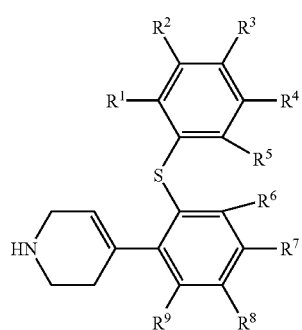

VI wherein $R^1$—$R^9$ are as described above.

Pharmaceutical Compositions

The compounds of the invention may be administered alone or in combination with pharmaceutically acceptable carriers or excipients, in either single or multiple doses.

The pharmaceutical compositions according to the invention may be formulated with pharmaceutically acceptable carriers or diluents as well as any other known adjuvants and excipients in accordance with conventional techniques such as those disclosed in the textbook *Remington: The Science and Practice of Pharmacy*, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen. Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid. Representative examples are mentioned above.

For parenteral administration, solutions of the novel compounds of the formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutical acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be a tablet, placed in a hard gelatine capsule in powder or pellet form or it can be in the form of a troche or lozenge.

The amount of solid carrier will vary widely but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

The compounds of the invention are prepared by the following general methods:

a) Deprotection or cleavage from a polymer support of a compound with formula II

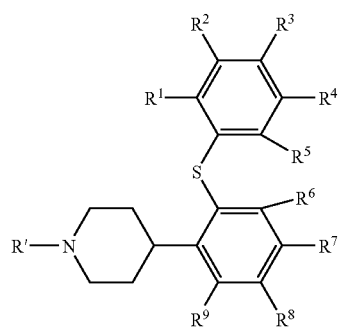

wherein $R^1$—$R^9$ are as previously described, and R' is a carbamate or a benzyl-derived protective group. These protective groups may be linked to a solid support, for example the Wang resin-based carbamate linker.

b) Chemical transformation of a compound with formula III to the corresponding diazonium compound and subsequent reaction with a thiophenol of formula IV

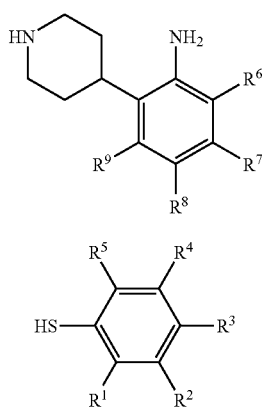

wherein $R^1$—$R^9$ are as previously described.

c) Reacting a compound of formula V with a thiophenol of formula IV in the presence of a palladium or copper catalyst

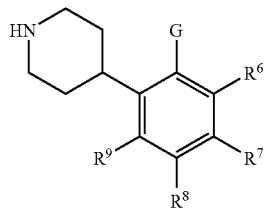

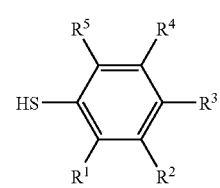

wherein $R^1$—$R^9$ are as previously described, and G is a chlorine, bromine, or iodine atom or a sulfonyl ester. The sulfonyl ester is derived from the corresponding phenol by reaction with 4-methyl-benzenesulfonyl chloride, trifluoro-methanesulfonic acid anhydride, 1,1,2,2,3,3,4,4,4-nonafluoro-butane-1-sulfonyl fluoride, or related compounds; or d) Hydrogenate the double bond in a compound of formula VI

VI wherein $R^1$—$R^9$ are as described above.

The deprotection according to method a) was performed by standard techniques, known to the persons skilled in the art and detailed in the textbook *Protective Groups in Organic Synthesis*, Greene and Wuts, Wiley Interscience, (1991), ISBN 0471623016. The cleavage from a polymer support, such as from the Wang resin based carbamate linker, according to method a) was performed according to literature known procedures (Zaragoza *Tetrahedron Lett.* 1995, 36, 8677-8678 and Conti et al. *Tetrahedron Lett.* 1997, 38, 2915-2918).

VII

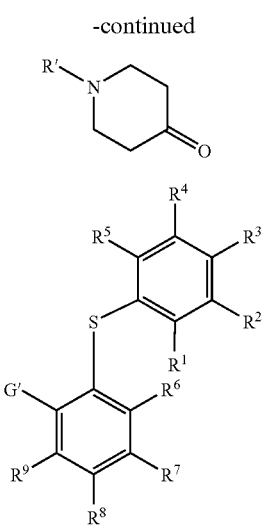

Compounds of formula II can be prepared by dehydrating a compound of formula VII under conditions that do not lead to cleavage of the N—R' bond followed by hydrogenation of the double bond. Alternatively, compounds of formula VII can be dehydrated with subsequent or concomitant cleavage of the N—R' bond to provide compounds of formula VI; subsequent protection of the amino group and hydrogenation of the double bond then provides compounds of formula II. The reduction of the double bond may be performed using standard heterogeneous hydrogenation procedures or using homogeneous hydrogenation methods such as e.g. Crabtree's or Wilkinson's catalysts (see e.g. *Encyclopedia of Reagents for Organic Synthesis*, Paquette (Ed.), Wiley (1995), ISBN 0471936235, p. 1447 and p 1253, respectively), or vice-versa. The dehydration reaction and optional deprotection of a compound of formula VII to yield compounds II or VI was performed in a similar manner as described in Palmer et al. *J. Med. Chem.* 1997, 40, 1982-1989.

The starting material of formula VII wherein R'=H was prepared from a compound of formula VII wherein R' is a carbamate or benzyl-derived protective group by deprotection under standard conditions known to the persons skilled in the art and detailed in the textbook *Protective Groups in Organic Synthesis*, Greene and Wuts, Wiley Interscience, (1991), ISBN 0471623016. Compounds of formula VII wherein R'=tert-butyl oxo carbonyl (BOC), may be prepared as described in Palmer et al. *J. Med. Chem.* 1997, 40, 1982-1989. Compounds VII were prepared from the corresponding properly substituted 1-bromo-phenylsulfanylbenzenes or 1-iodo-phenylsulfanylbenzenes of formula IX by metal-halogen exchange followed by addition of an appropriate electrophile of the formula VIII in a similar manner as described in Palmer et al. *J. Med. Chem.* 1997, 40, 1982-1989 or by following the procedures of Kitagawa et al. *Angew. Chem. Int. Ed.* 2000, 39, 2481-2483, or of Boymond et al. *Angew. Chem. Int. Ed.* 1998, 37, 1701-1703. Compounds VII, VIII, and IX have $R^1$—$R^9$ and R' as previously described, and G' is a bromine or iodine atom. The properly substituted 1-bromo-phenylsulfanylbenzenes or 1-iodo-phenylsulfanylbenzenes were prepared from thiophenols IV and properly substituted aryliodides or aryl bromides according to the general procedures by Schopfer and Schlapbach *Tetrahedron* 2001, 57, 3069-3073; Bates et al. *Org. Lett.* 2002, 4, 2803-2806 and Kwong et al. *Org. Lett.* 2002, 4, 581-584.

Starting materials of formula VII can also be prepared by palladium or copper catalysed coupling of a thiophenol of formula X with a compound of formula XI according to Schopfer and Schlapbach *Tetrahedron* 2001, 57, 3069-3073; Bates et al. *Org. Lett.* 2002, 4, 2803-2806, or Kwong et al. *Org. Lett.* 2002, 4, 581-584. Compounds X can be prepared by ortholithiation of compounds IV, or by metal-halogen exchange of properly substituted 2-bromo-thiophenol or 2-iodo-thiophenol derivatives, followed by addition of electrophile of formula VIII, as exemplified in the experimental. Compounds of formula X and XI have $R^1$—$R^9$, R', and G as described previously. The sulfonyl esters can be derived from the corresponding phenol by reaction with 4-methyl-benzenesulfonyl chloride, trifluoro-methanesulfonic acid anhydride, 1,1,2,2,3,3,4,4,4-nonafluoro-butane-1-sulfonyl fluoride, or related compounds, as described by e.g. Cho et al. *J. Org. Chem.*, 2003, 68, 3017-3025, Arnould et al. *Tetrahedron Lett.* 1996, 37, 45-23-4524, and Anderson et al. *J. Org. Chem.* 2003, 68, 9563-9573. The phenol in terms can be prepared from the analogous anisole or suitably protected phenol by standard techniques, known to the persons skilled in the art and detailed in the textbook *Protective Groups in Organic Synthesis*, Greene and Wuts, Wiley Interscience, (1991), ISBN 0471623016.

Starting materials of formula V and XI can be prepared by diazotation of properly substituted aniline derivatives followed by addition of either copper bromide or copper iodide as described in the textbook *Advanced Organic Chemistry* March, John Wiley & Sons (1992), ISBN 0471601802, by diazotation of the corresponding aniline derivative followed by addition of potassium iodide as described by Tunney and Stille *J. Org. Chem.* 1987, 52, 748-753, or by diazotization under the conditions reported by Doyle et al. *J. Org. Chem.* 1977, 42, 2426-2431 and Doyle et al. *J. Org. Chem.* 1980, 45, 2570-2575. Alternatively, compound V in which G is a sulfonyl ester may be derived from the corresponding phenol as described above for compound XI. The phenol in terms can be prepared from the analogous anisole or suitably protected phenol by standard techniques, known to the persons skilled in the art and detailed in the textbook *Protective Groups in Organic Synthesis*, Greene and Wuts, Wiley Interscience, (1991), ISBN 0471623016.

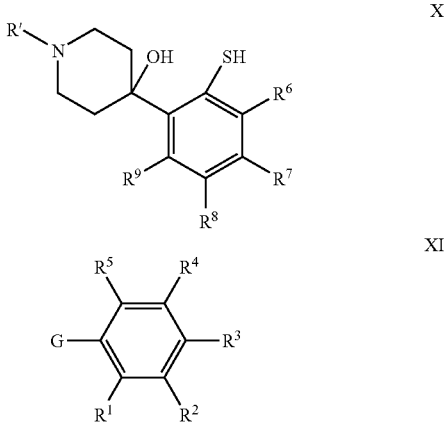

Compounds II can also be prepared by removal of the hydroxyl group from compounds VII using standard deoxygenation procedures (e.g. Barton-type reduction). One example of this uses activation with methyl oxalyl chloride followed by reduction with tri-n-butyltin hydride and 2-[(cyano-dimethyl-methyl)-azo]-2-methyl-propionitrile (AIBN) as described by Hansen et al. *Synthesis* 1999, 1925-1930. Alternatively, one can use trifluoro-acetic acid and triethyl-silane or use sodium borohydride or related reducing reagents as described in the textbook *Reductions in Organic Chemistry*, Hudlicky, ACS Monograph 188, The American Chemical Society (1996), ISBN 0841233446.

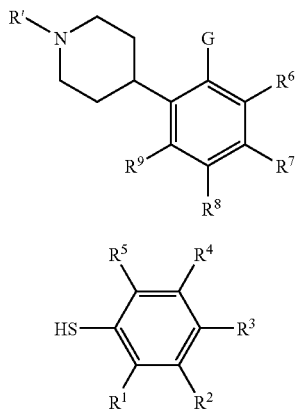

Compounds II can also be prepared by reacting compound XII with thiophenol IV in the presence of a palladium or copper catalyst using the methods described previously for compounds X and XI. Compound XII has $R^6$—$R^9$, R', and G are as defined previously. Compound XII may be prepared from compound III via the general diazotization methods outlined for compounds V and IX below, or from compound XX as discussed below.

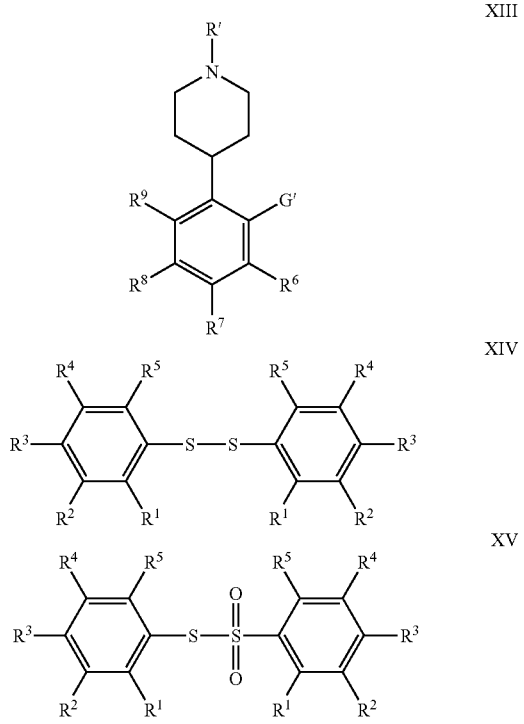

Compounds II can also be prepared by reacting compound XIII with an alkyl metal species followed by reaction with disulfide XIV, e.g. via the method reported by Carreno et al. *Tetrahedron,* 1991, 47, 605-614. Alternatively, the metallated species derived from compounds XIII may be quenched with compounds of formula XV according to the procedure of Marchand et al. *Tetrahedron* 2000, 56, 7331-7338. Compounds XIV and XV are either commercially available or can be prepared from thiophenols IV, e.g. via the methods described in the textbook *Advanced Organic Chemistry* March, John Wiley & Sons (1992), ISBN 0471601802, or by the procedures reported by Barnard *J. Chem. Soc.* 1957, 4673-4675, Miller *J. Chem. Soc.* 1925, 224-233, or Evans et al. *J. Org. Chem.* 1990, 55, 2337-2344. Compounds XIII can be prepared using the same techniques as discussed for compounds XII. For compounds XIII and XIV, $R^1$—$R^9$, R', and G' are as defined previously.

Diazotation of compound III followed by reaction with a thiophenol IV to yield compound I can be performed by addition of the diazonium salt of the corresponding aniline to a solution of sodium salt of a thiophenol in an aqueous suspension of copper under conditions similar to those described for starting material XI below. The starting material of formula III are either commercially available or can be prepared by methods analogues to those described in the literature (e.g. Berridge, M. S. et al. *J. Med. Chem.* 1993, 36, 1284-1290). Thiophenols IV are either commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, or from compounds XI using the methods of Arnould et al. *Tetrahedron Lett.* 1996, 37, 4523-4524 and Rane et al. *Tetrahedron Lett.* 1994, 35, 3225-3226 followed by deprotection under standard conditions known to the persons skilled in the art and detailed in the textbook *Protective Groups in Organic Synzthesis*, Greene and Wuts, Wiley Interscience, (1991), ISBN 0471623016.

The coupling of a compound of formula V with a thiophenol of formula IV according to method c) was performed in the presence of a palladium or copper catalyst e.g. by using the method described by Schopfer and Schlapbach *Tetrahedron* 2001, 57, 3069-307, Bates et al. *Org. Lett.* 2002, 4, 2803-2806, or Kwong et al. *Org. Lett.* 2002, 4, 581-584.

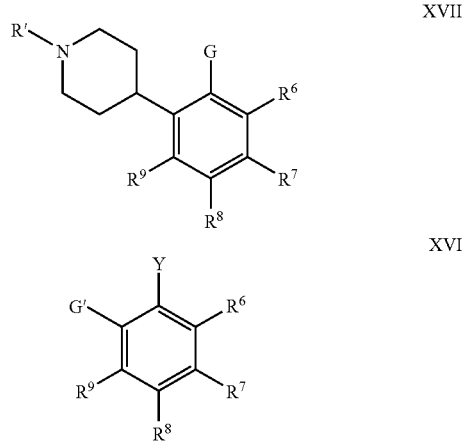

Compounds V can be prepared by from compounds XII by N-deprotection using standard techniques, known to the persons skilled in the art and detailed in the textbook *Protective Groups in Organic Synthesis*, Greene and Wuts, Wiley Interscience, (1991), ISBN 0471623016. Compounds XVII can be derived from compounds XVI by palladium catalysed reaction with 4-(4,4,5,5-tetramethyl-[1,3,2]dioxaborolan-2-yl)-3,6-dihydro-2H-pyridine-1-carboxylic acid tert-butyl ester (or related boronic acid derivatives) using the method of Eastwood *Tetrahedron Lett.* 2000, 41, 3705-3708 or by using the conditions for the Suzuki coupling reported by Zhuravel and Nguyen *Tetrahedron Lett.* 2001, 42, 7925-7928 as exemplified in the experimental followed by reduction of the double bond as described previously. Compounds of formula XVI have $R^6$—$R^9$, and G' as described above, while Y is either a chlorine, bromine, or iodine atom or a hydroxyl group, or a methoxy group or

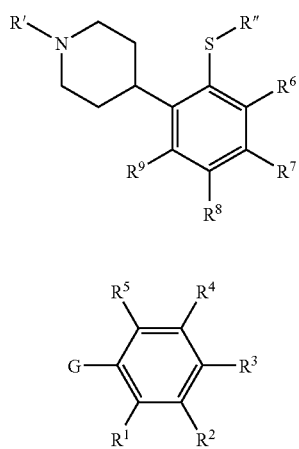

XVII

XI alternatively protected hydroxyl group that can be deprotected under conditions, known to the persons skilled in the art and detailed in the textbook *Protective Groups in Organic Synthesis*, Greene and Wuts, Wiley Interscience, (1991), ISBN 0471623016, or a sulfonyl ester as described for compounds of formula XI.

Compounds of formula II can further be prepared by coupling of compounds of structures XVII when R" is a hydrogen and compound XI in the presence of a suitable palladium or copper catalyst as described by Schopfer and Schlapbach *Tetrahedron* 2001, 57, 3069-3073; Bates et al. *Org. Lett.* 2002, 4, 2803-2806 or Kwong et al. *Org. Lett.* 2002, 4, 581-584. Compound XVII has $R^6$—$R^9$, and R' as defined previously, and R" is a hydrogen or a trialkyl, a dialkylaryl, a alkyldiaryl silyl protection group. Compounds of formula XVII for which R" is a silyl group can be prepared from compounds of formula XII under the conditions reported by Arnould et al. *Tetrahedron Lett.* 1996, 37, 45-23-4524 and Rane et al. *Tetrahedron Lett.* 1994, 35, 3225-3226. The coupling of compounds XVII and XI when R" is a silyl group can be effected by the use of copper or palladium catalyst in the presence of a stoichiometric amount of fluoride ions, e.g. in the form of tetra-n-butyl ammonium fluoride (TBAF) under conditions closely related to those reported by Arnould et al. *Tetrahedron Lett.* 1996, 37, 45-23-4524 and Rane et al. *Tetrahedron Lett.* 1994, 35, 3225-3226 as detailed in the experimental.

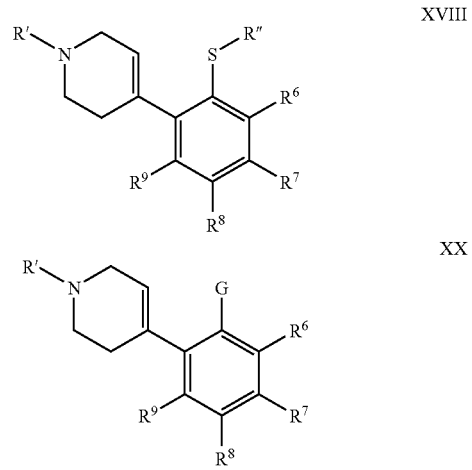

XVIII

XX

Compounds of formula II can be prepared by coupling of compounds XVIII and XI in the presence of a suitable copper or palladium catalyst as detailed for the analogous coupling of compounds XVII and XI above, followed by reduction of the double bond under the conditions outlined above for compound VI. Compounds XVIII have $R^6$—$R^9$, R', and R" as defined previously. Compounds of formula XVIII for which R" is a silyl group can be prepared from compounds of formula XX wherein $R^6$—$R^9$, R', and G are as defined above under the conditions reported by Arnould et al. *Tetrahedron Lett.* 1996, 37, 4523-4524 and Rane et al. *Tetrahedron Lett.* 1994, 35, 3225-3226. Compound XX can be derived from compound XVI by copper or palladium catalysed reaction with 4-(4,4,5,5-tetramethyl-[1,3,2]dioxaborolan-2-yl)-3,6-dihydro-2H-pyridine-1-carboxylic acid tert-butyl ester (or related boronic acid derivatives) as described by Eastwood *Tetrahedron Lett.* 2000, 41, 3705-3708 or by using the conditions for the Suzuki coupling reported by Zhuravel and Nguyen *Tetrahedron Lett.* 2001, 42, 7925-7928 as exemplified in the experimental. Alternatively, compound XX can be derived from compound XXI by directed ortho lithiation (L=hydrogen) or halide-lithium exchange (L=iodide or bromide), trapping with electrophile VIII as described for compound XXI below, followed by an elimination-protection sequence as previously described for compounds VII. For compounds XXI

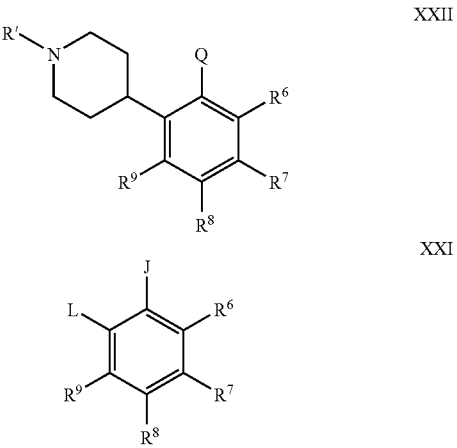

XXII

XXI $R^6$—$R^9$ are as defined above while J is a methoxy group or a similarly directing hydroxyl derivative, and L is a hydrogen, bromide, or iodide atom.

Compound X may be prepared from compounds XXI by directed ortho lithiation or halide-metal exchange according to the methods reported by Palmer et al. *J. Med. Chem.* 1997, 40, 1982-1989, Kitagawa et al. *Angew. Chem. Int. Ed.* 2000, 39, 2481-2483, or Boymond et al *Angew. Chem. Int. Ed.* 1998, 37, 1701-1703, or according to the procedures reported in the textbook *Organometallics in Synthesis. A. Manual*, Schlosser (Ed), John Wiley & Sons, Ltd (2002), ISBN 0471984167 followed by quenching with eletrophiles of the formula VIII. Upon deoxygenation or elimination-reduction as described above for compound VII, compounds XXI may be transformed into compounds XXII for which $R^6$—$R^9$ are as defined above, and Q is an sulfonyl ester as described for compounds XI. Hence, compounds XXII can be transformed into compounds XVII under the conditions described for compounds XVII. The product of the reaction of the lithiated compound XXI and the electrophile VIII can be activated as a sulfonyl ester after transformation of J into a hydroxyl group by methods known to the persons skilled in the art and detailed in the textbook *Protective Groups in Organic Synthesis*, Greene and Wuts, Wiley Interscience, (1991), ISBN 0471623016. The resulting sulfonyl esters can be transformed into compounds X under the conditions discussed for compounds XVII followed by cleavage of the silyl protective group by methods known to the persons skilled in the art and detailed in the textbook *Protective Groups in Organic Synthesis*, Greene and Wuts, Wiley Interscience, (1991), ISBN 0471623016.

The reduction of the double bond according to method d) was generally performed by catalytic hydrogenation at low pressure (<3 bar) in a Parr shaker apparatus. Starting material of formula VI may be prepared from compounds of formula VII.

EXAMPLES

Analytical LC-TOF data were obtained on a 4 channel Micromass LCT instrument equipped with MUX electrospay source and Waters 1525 LC system. Analytical LC-MS data were obtained on a PE Sciex API 150EX instrument equipped with IonSpray source and Shimadzu LC-8A/SLC-10A LC system. Column: 30×4.6 mm Waters Symmetry C18 column with 3.5 µm particle size; Solvent system: A=water/TFA (100:0.05) and B=water/acetonitrile/TFA (5:95:0.03) (TFA=trifluoro-acetic acid); Method: Linear gradient elution with 90% A to 100% B in 4 min and with a flow rate of 2 mL/min. Purity was determined by integration of the UV (254 nm) and ELSD trace. The retention times (RT) are expressed in minutes.

Preparative LC-MS-purification was performed on the same instrument. Column: 50×20 mm YMC ODS-A with 5 µm particle size; Method: Linear gradient elution with 80% A to 100% B in 7 min and with a flow rate of 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Chloroform (99.8% D) or dimethyl sulfoxide (99.8% D) were used as solvents. Tetramethylsilane (TMS) was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet and b=broad singlet.

Reactions were run under inert atmosphere and dry conditions unless otherwise stated. Reactions carried out under microwave conditions were performed in a SmithSynthesizer from Personal Chemistry operating at 2450 MHz.

Preparation of Intermediates 1-bromo-2-(4-chloro-phenylsulfanyl)-5-(trifluoromethyl)-benzene (Intermediate for 1a)

To a stirred solution of tris(dibenzylidene)dipalladium(0) (Pd$_2$dba$_3$, 0.183 g, 0.2 mmol) and bis(2-diphenylphosphinophenyl)ether (DPEphos, 0.215 g, 0.2 mmol) in toluene (80 mL) was added 3-bromo-4-iodobenzotrifluoride (7.02 g, 20 mmol; prepared from 2-bromo-4-trifluoromethyl-phenylamine by diazotization according to the general procedure by Tunney and Stille *J. Org. Chem.* 1987, 52, 748-753), 4-chlorothiophenol (2.89 g, 20 mmol) and potassium tert-butoxide (2.46 g, 22 mmol) at room temperature (rt). The reaction mixture was stirred for 2.5 h at 100° C. and then cooled to room temperature (rt) and filtered through celite. The solvent was evaporated off and the crude product was purified by flash chromatography on silica gel (eluent: ethyl acetate/heptane 2:8) to produce 4.53 g (81%) of 1-bromo-2-(4-chloro-phenylsulfanyl)-5-(trifluoromethyl)-benzene as an oil.

The following intermediates for 1b-1m and 2a-2x were prepared analogously:

1-Bromo-2-(4-methoxy-phenylsulfanyl)-benzene (intermediate for 1b). Prepared from 4-methoxy-benzenethiol and 1-bromo-2-iodo-benzene.

1-Bromo-2-(2,4-dimethyl-phenylsulfanyl)-5-(trifluoromethyl)-benzene (intermediate for 1c). Prepared from 2,4-dimethyl-benzenethiol and 2-bromo-1-iodo-4-trifluoromethyl-benzene.

1-Bromo-2-(4-chloro-phenylsulfanyl)-4-fluoro-benzene (intermediate for 1d). Prepared from 4-chloro-benzenethiol and 1-bromo-4-fluoro-2-iodo-benzene.

1-Bromo-4-fluoro-2-(4-methoxy-phenylsulfanyl)-benzene (intermediate for 1e). Prepared from 4-methoxy-benzenethiol and 1-bromo-4-fluoro-2-iodo-benzene.

1-Bromo-2-(4-methyl-phenylsulfanyl)-5-methyl-benzene (intermediate for 1f). Prepared from 4-methyl-benzenethiol and 2-bromo-1-iodo-4-methyl-benzene.

1-Bromo-2-(2,4-dimethyl-phenylsulfanyl)-5-methyl-benzene (intermediate for 1 g) Prepared from 2,4-dimethyl-benzenethiol and 2-bromo-1-iodo-4-methyl-benzene.

1-Bromo-2-(4-fluoro-2-methyl-phenylsulfanyl)-5-methyl-benzene (intermediate for 1 h). Prepared from 4-fluoro-1-iodo-2-methyl-benzene and 2-bromo-4-methyl-benzenethiol (prepared from 2-bromo-4-methyl-phenylamine by diazotization according to the procedure reported for the conversion of 3-toluidine to 3-thiocresol by Tarbell and Fuliushima *J. Am. Chem. Soc.* 1946, 68, 1456-1460).

1-Bromo-2-(4-methoxy-phenylsulfanyl)-5-methyl-benzene (intermediate for 1i) Prepared from 4-methoxy-benzenethiol and 2-bromo-1-iodo-4-methyl-benzene.

1-Bromo-2-(4-chloro-2-methyl-phenylsulfanyl)-benzene (intermediate for 1j). Prepared from 4-chloro-1-iodo-2-methyl-benzene and 2-bromo-benzenethiol.

1-Bromo-2-(4-chloro-2-fluoro-phenylsulfanyl)-benzene (intermediate for 1k). Prepared from 4-chloro-2-fluoro-1-iodo-benzene and 2-bromo-benzenethiol.

1-Bromo-2-(2,4-dichloro-phenylsulfanyl)-benzene (intermediate for 1l). Prepared from 2,4-dichloro-benzenethiol and 2-bromo-1-iodo-benzene.

1-Bromo-2-(2-chloro-4-methoxy-phenylsulfanyl)-benzene (intermediate for 1m). Prepared from 2-bromo-benzenethiol and 2-chloro-1-iodo-4-methoxy-benzene (prepared from 4-amino-3-chloro-phenol by diazotization according to the general procedure by Tunney and Stille *J. Org. Chem.* 1987, 52, 748-753 followed by alkylation with methyl iodide according to the general procedure by Uozumi et al. *J. Org. Chem.* 1993, 58, 1945-1945)

1-Bromo-2-(4-chloro-phenylsulfanyl)-benzene (intermediate for 2a). Prepared from 4-chloro-benzenethiol and 1-bromo-2-iodo-benzene.

2-Bromo-5-fluoro-1-(4-methoxy-phenylsulfanyl)-benzene (intermediate for 2b). Prepared from 4-methoxy-benzenethiol and 2-bromo-4-fluoro-1-iodo-benzene (prepared from 2-bromo-4-fluoro-phenylamine by diazotization according to the general procedure by Tunney and Stille *J. Org. Chem.* 1987, 52, 748-753)

1-Bromo-2-(4-chloro-phenylsulfanyl)-5-fluoro-benzene (intermediate for 2c). Prepared from 4-chloro-benzenethiol and 2-bromo-4-fluoro-1-iodo-benzene.

1-Bromo-3-fluoro-2-(4-methoxy-phenylsulfanyl)-benzene (intermediate for 2d). Prepared from 4-methoxy-benzenethiol and 1-bromo-3-fluoro-2-iodo-benzene (prepared from 2-bromo-6-fluoro-phenylamine by diazotization according to the general procedure by Tunney and Stille *J. Org. Chem.* 1987, 52, 748-753).

1,5-Dibromo-2-(2,4-dimethyl-phenylsulfanyl)-benzene (intermediate for 2e). Prepared from 2,4-dimethyl-benzenethiol and 2,4-dibromo-1-iodo-benzene (prepared from 2,4-dibromo-phenylamine by diazotization according to the general procedure by Tunney and Stille *J. Org. Chem.* 1987, 52, 748-753).

1-Bromo-4-fluoro-2-(4-methyl-phenylsulfanyl)-benzene (intermediate for 2f). Prepared from 4-methyl-benzenethiol and 1-bromo-4-fluoro-2-iodo-benzene.

1-Bromo-2-(4-chloro-phenylsulfanyl)-5-methyl-benzene (intermediate for 2 g). Prepared from 4-chloro-benzenethiol and 2-bromo-1-iodo-4-methyl-benzene.

1-Bromo-2-(4-methyl-phenylsulfanyl)-5-trifluoromethyl-benzene (intermediate for 2h). Prepared from 4-methyl-benzenethiol and 3-bromo-4-iodo-benzotrifluoride.

1-Bromo-5-fluoro-2-(2,4-dimethyl-phenylsulfanyl)-benzene (intermediate for 2i). Prepared from 2,4-dimethyl-benzenethiol and 2-bromo-4-fluoro-1-iodo-benzene.

1-Bromo-2-(4-fluoro-phenylsulfanyl)-5-fluoro-benzene (intermediate for 2j). Prepared from 4-fluoro-benzenethiol and 2-bromo-4-fluoro-1-iodo-benzene.

1-Bromo-2-(2-chloro-4-fluoro-phenylsulfanyl)-5-fluoro-benzene (intermediate for 2k). Prepared from 2-chloro-4-fluoro-benzenethiol and 2-bromo-4-fluoro-1-iodo-benzene.

1-Bromo-5-fluoro-2-(4-methyl-phenylsulfanyl)-benzene (intermediate for 2l). Prepared from 4-methyl-benzenethiol and 2-bromo-4-fluoro-1-iodo-benzene.

1-Bromo-5-fluoro-2-(3-methoxy-phenylsulfanyl)-benzene (intermediate for 2m). Prepared from 3-methoxy-benzenethiol and 2-bromo-4-fluoro-1-iodo-benzene.

1-Bromo-2-(2-chloro-4-methyl-phenylsulfanyl)-5-fluoro-benzene (intermediate for 2n). Prepared from 2-chloro-4-methyl-benzenethiol and 2-bromo-4-fluoro-1-iodo-benzene.

1-Bromo-2-(2-chloro-4-methoxy-phenylsulfanyl)-5-fluoro-benzene (intermediate for 2o). Prepared from 2-chloro-1-iodo-4-methoxy-benzene and 2-bromo-4-fluoro-benzenethiol (prepared from 2-bromo-4-fluoro-phenylamine by diazotization according to the procedure reported for the conversion of 3-toluidine to 3-thiocresol by Tarbell and Fukushima *J. Am. Chem. Soc.* 1946, 68, 1456-1460).

1-Bromo-2-(4-chloro-2-fluoro-phenylsulfanyl)-5-fluoro-benzene (intermediate for 2p). Prepared from 4-chloro-2-fluoro-1-iodo-benzene and 2-bromo-4-fluoro-benzenethiol.

1-Bromo-2-(2-fluoro-4-methyl-phenylsulfanyl)-5-fluoro-benzene (intermediate for 2q). Prepared from 2-fluoro-1-iodo-4-methyl-benzene and 2-bromo-4-fluoro-benzenethiol.

1-Bromo-2-(2-chloro-phenylsulfanyl)-5-fluoro-benzene (intermediate for 2r). Prepared from 2-chloro-benzenethiol and 2-bromo-4-fluoro-1-iodo-benzene.

1-Bromo-2-(2,4-dichloro-phenylsulfanyl)-5-fluoro-benzene (intermediate for 2s). Prepared from 2,4-dichloro-benzenethiol and 2-bromo-4-fluoro-1-iodo-benzene.

1-Bromo-2-(2,4-difluoro-phenylsulfanyl)-5-fluoro-benzene (intermediate for 2t). Prepared from 2,4-difluoro-benzenethiol and 2-bromo-4-fluoro-1-iodo-benzene.

1-Bromo-2-(2,4-dimethyl-phenylsulfanyl)-3-fluoro-benzene (intermediate for 2u). Prepared from 2,4-dimethyl-benzenethiol and 1-bromo-3-fluoro-2-iodo-benzene.

1-Bromo-5-fluoro-2-(phenylsulfanyl)-benzene (intermediate for 2v). Prepared from benzenethiol and 2-bromo-4-fluoro-1-iodo-benzene.

1-Bromo-2-(4-bromo-2-fluoro-phenylsulfanyl)-5-fluoro-benzene (intermediate for 2x). Prepared from 4-bromo-2-fluoro-1-iodo-benzene and 2-bromo-4-fluoro-benzenethiol.

4-(5-Fluoro-2-mercapto-phenyl)-4-hydroxy-piperidine-1-carboxylic acid tert-butyl ester (Intermediate for 2a1-2a6)

To a solution of 2-bromo-4-fluoro-thiophenol (6.0 g, 28.9 mmol) in dry tetrahydrofuran (TBF, 25 mL) at −78° C. was slowly added methyl lithium (1M in cumene/TBF, 28.9 mL, 28.9 mmol). After 30 min at −78° C., tert-butyl lithium (1.7 M in THF, 39.9 mL, 63.8 mmol) was added and the reaction mixture was stirred 30 min at −78° C. A solution of 4-oxo-piperidine-1-carboxylic acid tert-butyl ester (5.77 g, 28.9 mmol) in THE (20 mL) was added and the reaction mixture was allowed to warm to rt and stirred overnight. Water (50 mL) and ethyl acetate (25 mL) were added, and organic phase was discarded. The aqueous phase was extracted with ethyl acetate (50 mL) and saturated aqueous ammonium chloride (25 mL). The organic phase was washed with saturated aqueous ammonium chloride (25 mL) and dried over magnesium sulfate, and evaporated to afford the crude product. The crude product was purified by flash chromatography on silica gel (eluent: An increasing amount (0-20%) of ethyl acetate in heptane). Yield: 4.67 g (49%).

4-(2-Tri-iso-propylsilanylsulfanyl-phenyl)-piperidine-1-carboxylic acid tert-butyl ester (Intermediate for 3a1-3a6)

To a 10 mL microwave vial was added 4-(2-hydroxy-phenyl)-piperidine-1-carboxylic acid tert-butyl ester (0.30 g, 1.08 mmol), N-phenyl-bis(trifluoromethanesulfoneimide) (393 mg, 1.1 mmol), and potassium carbonate (448 mg, 3.25 mmol). THE (2.2 mL) was added and the vial was closed with a septum. The mixture was heated under microwave conditions at 120° C. for 10 min. The reaction mixture was cooled to rt and diluted with diethyl ether (10 mL). The mixture was filtered through celite, the solvent was evaporated off and the crude product was purified by chromatography on silica gel (eluent: An increasing amount (0-100%) of ethyl acetate in heptane) to produce 349 mg of 4-(2-trifluoromethanesulfonyloxy-phenyl)-piperidine-1-carboxylic acid tert-butyl ester. Some of this material (92 mg, 0.22 mmol) and tri-(iso-propyl)-silanethiol (59 mg, 0.31 mmol) was dissolved in dry toluene (1.1 mL) and added to palladium(II) acetate (5 mg, 0.022 mmol), (S)-2,2'-bis-(di-p-tolyl-phosphanyl)-[1,1'] binaphthalenyl (S-(−)-Tol-BINAP, 16 mg, 0.024 mmol) and sodium tert-butoxide (30 mg, 0.31 mmol) placed in a 10 mL microwave vial. TBF (2.2 mL) was added and the vial was closed with a septum. The mixture was heated under microwave conditions at 120° C. for 30 min. The reaction mixture was cooled to rt and the solvent was evaporated off. The crude product was purified by flash chromatography on silica gel (eluent: An increasing amount (0-100%) of ethyl acetate in heptane). Yield of 4-(2-tri-iso-propylsilanylsulfanyl-phenyl)-piperidine-1-carboxylic acid tert-butyl ester: 64 mg (65%).

4-(5-Methyl-2-tri-iso-propylsilanylsulfanyl-phenyl)-piperidine-1-carboxylic acid tert-butyl ester (intermediate for 3b1-3b12) was prepared in a similar way from 4-(2-hydroxy-5-methyl-phenyl)-piperidine-1-carboxylic acid tert-butyl ester. This compound was prepared from 2-bromo-4-methyl-phenol by the following procedure: A mixture of 2-bromo-4-methyl-phenol (1.12 g, 6.0 mmol), 4-(4,4,5,5-tetramethyl-[1,3,2]dioxaborolan-2-yl)-3,6-dihydro-2H-pyridine-1-carboxylic acid tert-butyl ester (1.86 g, 6.0 mmol), dichloro[1,1']-bis(diphenylphosphino)ferrocene]palladium (II) dichloromethane adduct (0.245 g, 0.3 mmol), and potassium carbonate (2.48 g, 18.0 mmol) was suspended in 1,2-dimethoxy-ethane (DME, 23 mL) and water (7 mL). The suspension was stirred overnight at 90° C., cooled to RT, and then quenched at 5° C. by adding aqueous hydrochloric acid (2M, 18 mL). Diethyl ether (18 mL) was added, the phases were separated and the aqueous phase was extracted with diethyl ether (2×18 mL) The combined organic phases were washed with saturated aqueous sodium chloride (30 mL), and dried over magnesium sulfate, and evaporated. The crude product was purified by chromatography on silica gel (eluent: An increasing amount (0-100%) of ethyl acetate in heptane). Yield: 1.03 g (59%) of the intermediate 4-(2-hydroxy-5-methyl-phenyl)-3,6-dihydro-2H-pyridine-1-carboxylic acid tert-butyl ester. This material was dissolved in ethanol (35 mL), 20% Pd/C (0.1 g) was added, and the mixture was treated with hydrogen gas (3 bar) on a Parr shaker apparatus overnight. The mixture was filtered through celite and the solvent was evaporated off to produce 4-(2-hydroxy-5-methyl-phenyl)-piperidine-1-carboxylic acid tert-butyl ester. Yield: 0.91 g (91%).

4-(5-Methoxy-2-tri-iso-propylsilanylsuyfanyl-phenyl)-piperidine-1-carboxylic acid tert-butyl ester (intermediate for 3c1-3c4) was prepared in a similar way from 4-(2-hydroxy-5-methoxy-phenyl)-piperidine-1-carboxylic acid tert-butyl ester. This compound was prepared from 2-bromo-4-methoxy-phenol (prepared by bromination from 4-methoxy-phenol according to the procedure by Carreno et al. *Synlett* 1997, 1241-1242) was coupled to 4-(4,4,5,5-tetramethyl-[1,3,2]dioxaborolan-2-yl)-3,6-dihydro-2H-pyridine-1-carboxylic acid tert-butyl ester, and the product was reduced with Pd/C and hydrogen gas as described for 4-(2-hydroxy-5-methyl-phenyl)-piperidine-1-carboxylic acid tert-butyl ester.

4-(2-Fluoro-6-tri-iso-propylsilanylsulfanyl-phenyl)-piperidine-1-carboxylic acid tert-butyl ester (intermediate for 3d1-3d27). A solution of 1-fluoro-3-methoxy-benzene (10.0 g, 79.3 mmol) in dry THF (100 mL) was treated with n-butyl lithium (1.6M in hexane, 49.8 mL, 79.3 mmol) at −78° C. for five hours. A solution of 4-oxo-piperidine-1-carboxylic acid tert-butyl ester (15.8 g, 79.3 mmol) in THF (50 mL) was added at a rate so that the temperature was maintained below −5° C., and the reaction mixture was allowed to warm to rt and stirred overnight. Saturated aqueous ammonium chloride (50 mL) followed by ethyl acetate (10 mL) was added. The organic layer was washed with saturated aqueous ammonium chloride (50 mL), dried over magnesium sulfate, and evaporated in vacuo to afford the crude product. Purification by chromatography over silica gel (eluent: ethyl acetate/heptane 1:1) provided 7.80 g (31%) of 4-(2-fluoro-6-methoxy-phenyl)-4-hydroxy-piperidine-1-carboxylic acid tert-butyl ester. A solution of this compound in acetic acid (70 mL) was treated with concentrated aqueous hydrochloric acid (30 mL) at reflux overnight. The volatiles were removed in vacuo, and the residue was partitioned between methylene chloride (100 mL) and a mixture of saturated aqueous sodium bicarbonate (100 mL) and aqueous sodium hydroxide (10%, to adjust pH to 11). The organic layer was dried over magnesium sulfate and the volatiles were removed in vacuo. The residue was refluxed overnight in a mixture of 33% hydrogen bromide in acetic acid (10 mL) and concentrated aqueous hydrobromic acid (20 mL). Approximately 15 mL of the solvent was removed in vacuo and the residue was cooled on an icebath for 3 h to precipitate 4.10 g (59% overall) of 4-(5-fluoro-2-methoxy-phenyl)-1,2,3,6-tetrahydro-pyridine as the hydrobromic acid salt. A slurry of this compound (4.10 g, 14.2 mmol) in 1,2-dichloro-ethane (100 mL) and triethyl amine (2.3 mL) is stirred at rt for 30 min before Boc$_2$O (2.78 g, 14.0 mmol) was added. After stirring overnight, the precipitate was filtered off, and the filtrate is washed with saturated aqueous ammonium chloride (50 mL) and dried over magnesium sulfate. The volatiles were removed in vacuo to yield 1.02 g (23%) of 4-(2-fluoro-6-hydroxy-phenyl)-1,2,3,6-tetrahydro-pyridine-1-carboxylic acid tert-butyl ester. This material was dissolved in a mixture of ethyl acetate (10 mL) and ethanol (40 mL) and treated overnight with 5% Pd/C (0.1 g) and hydrogen gas (3 bar) using a Parr shaker apparatus. The catalyst was removed by filtration, and the volatiles were removed in vacuo. The residue (1.0 g) was suspended in 1,2-dichloro-ethane (20 mL) and treated with ethyl-di-iso-propyl-amine (0.53 g, 4.1 mmol) at 0° C. for 30 min before 1,1,2,2,3,3,4,4,4-nonafluoro-butane-1-sulfonyl fluoride (1.12 g, 3.7 mmol) was added and stirring was continued overnight at rt. The precipitate was filtered off, and the filtrate was washed with water (20 mL), dried over magnesium sulfate, and evaporated to afford the crude product. Purification by chromatography over silica gel (eluent: ethyl acetate/heptane 1:4) provided 1.27 g (65% over two steps) of 4-[2-fluoro-6-(nonafluorobutane-1-sulfonyloxy)-phenyl]-piperidine-1-carboxylic acid tert-butyl ester. A mixture of this compound (1.27 g, 2.2 mmol) and sodium tert-butoxide (0.27 g, 2.9 mmol) in dry toluene (25 mL) was added to a solution of Pd$_2$dba$_3$ (0.10 g, 0.11 mmol) and DPEphos (0.12 g, 0.22 mmol) in dry toluene (25 mL). Tri-iso-propyl-silanethiol (0.42 g, 2.2 mmol) was added, and the mixture was stirred for 5 h at 100° C. After cooling to rt, the crude mixture was washed with water (50 mL), dried over magnesium sulfate, and the volatiles were removed in vacuo. The residue was purified by chromatography over silica gel (eluent: ethyl acetate/heptane 1:4) to yield 0.8 g (78%) of 4-(2-fluoro-6-tri-iso-propylsilanylsulfanyl-phenyl)-piperidine-1-carboxylic acid tert-butyl ester.

4-(5-Fluoro-2-tri-iso-propylsilanylsulfanyl-phenyl)-piperidine-1-carboxylic acid tert-butyl ester (Intermediate for 3e1-3e10)

A mixture of 2-bromo-4-fluoro-1-methoxy-benzene (36.2 g, 176.7 mmol) and dry TBF (25 mL) was added to a cooled solution of n-butyl lithium (2.1 M in hexane, 101 mL, 212.1 mmol) in dry THE (100 mL) at rate so that the temperature was maintained below −40° C. The mixture was stirred for 30 min at −78° C. before 4-oxo-piperidine-1-carboxylic acid ethyl ester (30.4 g, 176.7 mmol) was added at a rate so that the temperature was maintained below −50° C. The resulting mixture was allowed to warm to rt and stirring was continued overnight. Water (100 mL) and ethyl acetate (100 mL) was added. The organic layer was washed with saturated aqueous ammonium chloride (100 mL), dried over magnesium sulfate, and evaporated in vacuo to afford 52.3 g (>95%.) of 4-(5-fluoro-2-methoxy-phenyl)-4-hydroxy-piperidine-1-carboxylic acid ethyl ester, which was sufficiently pure for the next step. This material was dissolved in triethyl-silane (100 mL) and TFA (200 mL) and stirred at rt for 3 days. The volatiles were removed in vacuo and the residue was purified by chromatography on silica gel (eluent: ethyl acetate/heptane 1:3) to afford 44.4 g (ca. 90%) of 4-(5-fluoro-2-methoxy-phenyl)-piperidine-1-carboxylic acid ethyl ester. This material was refluxed overnight in a mixture of 33% hydrogen bromide in acetic acid (75 mL) and concentrated aqueous hydrobromic acid (75 mL). The crude mixture was cooled on an icebath, and 18.9 g (43%) of 4-fluoro-2-piperidin-4-yl-phenol as the hydrobromic acid salt. A slurry of this compound (23.9 g, 86.5 mmol) in dichloromethane (200 mL) was treated with triethyl amine (13.2 mL, 95.2 mmol) for 1 h before Boc₂O (18.9 g, 86.5 mmol) was added and stirring was continued for 30 min. The crude mixture was washed with saturated aqueous ammonium chloride (50 mL) and water (25 mL). The organic layer was dried over magnesium sulfate and the volatiles were removed in vacuo. The residue crystallized to yield 14.2 g (55%) of 4-(5-fluoro-2-hydroxy-phenyl)-piperidine-1-carboxylic acid tert-butyl ester. This compound was transformed into 4-(5-fluoro-2-tri-iso-propylsilanylsulfanyl-phenyl)-piperidine-1-carboxylic acid tert-butyl ester in a similar way as described for 4-(2-fluoro-6-tri-iso-propylsilanylsulfanyl-phenyl)-piperidine-1-carboxylic acid tert-butyl ester.

4-(4-Fluoro-2-tri-iso-propylsilanylsulfanyl-phenyl)-piperidine-1-carboxylic acid tert-butyl ester (Intermediate for 3f1-3f13)

Using the procedure described for 4-(2-hydroxy-5-methyl-phenyl)-piperidine-1-carboxylic acid tert-butyl ester, 2-bromo-5-fluoro-phenol was converted into 4-(4-fluoro-2-hydroxy-phenyl)-piperidine-1-carboxylic acid tert-butyl ester. This compound was transformed into 4-(4-fluoro-2-triisopropylsilanylsulfanyl-phenyl)-piperidine-1-carboxylic acid tert-butyl ester under conditions described for 4-(2-fluoro-6-tri-iso-propylsilanylsulfanyl-phenyl)-piperidine-1-carboxylic acid tert-butyl ester.

4-Hydroxy-4-(2-mercapto-phenyl)-piperidine-1-carboxylic acid tert-butyl ester (Intermediate for 4a)

This intermediate was prepared from 2-bromo-benzenethiol and 4-oxo-piperidine-1-carboxylic acid tert-butyl ester in a similar way as described for 4-(5-fluoro-2-mercapto-phenyl)-4-hydroxy-piperidine-1-carboxylic acid tert-butyl ester.

Preparation of Further Intermediates

1-tert-Butoxycarbonyl-4-[2-(4-chlorophenylsulfanyl)-5-trifluoromethyl-phenyl]-piperidine-4-ol (Intermediate for 1a)

A solution of n-butyl lithium (2.5 M in hexane, 6.5 mL, 16.2 mmol) was slowly added to a stirred solution of 1-bromo-2-(4-chlorophenylsulfanyl)-5-(trifluoromethyl) benzene (5.96 g, 16.2 mmol) in dry THF (40 mL) under argon at −78° C. The solution was stirred for 10 min before 4-oxo-piperidine-1-carboxylic acid tert-butyl ester (3.23 g, 16.2 mmol) was added in one portion. The solution was allowed to warm to rt and then stirred overnight. Saturated aqueous ammonium chloride (80 mL) was added and the solution was extracted with ethyl acetate (80 mL). The organic phase was washed with saturated aqueous sodium chloride (50 mL), dried over magnesium sulfate and the solvent was evaporated off. The crude product was purified by flash chromatography on silica gel (eluent: ethyl acetate/heptane 2:8) to produce the target compound as a white foam, yield: 4.53 g (57%).

The following intermediates for 1b-1m and 2a-2x were prepared analogously from the corresponding previously described intermediates:

1-tert-Butoxycarbonyl-4-[2-(4-methoxy-phenylsulfanyl)-phenyl]-piperidine-4-ol (intermediate for 1b).

1-tert-Butoxycarbonyl-4-[2-(2,4-dimethyl-phenylsulfanyl)-5-(trifluoromethyl-phenyl]-piperidine-4-ol (intermediate for 1c).

1-tert-Butoxycarbonyl-4-[2-(4chloro-phenylsulfanyl)-4-fluoro-phenyl]-piperidine-4-ol (intermediate for 1d).

1-tert-Butoxycarbonyl-4-[2-(4-methoxy-phenylsulfanyl)-4-fluoro-phenzyl]-piperidine-4-ol (intermediate for 1e).

1-tert-Butoxycarbonyl-4-[2-(4-methyl-phenylsulfanyl)-5-methyl-phenyl]-piperidine-4-ol (intermediate for 1f).

1-tert-Butoxycarbonyl-4-[2-(2,4-dimethyl-phenylsulfanyl)-5-methyl-phenyl]-piperidine-4-ol (intermediate for 1g).

1-tert-Butoxycarbonyl-4-[2-(4-fluoro-2-methyl-phenylsulfanyl)-5-methyl-phenyl]-piperidine-4-ol (intermediate for 1h).

1-tert-Butoxycarbonyl-4-[2-(4-methoxy-phenylsulfanyl)-5-methyl-phenyl]-piperidine-4-ol (intermediate for 1i).

1-tert-Butoxycarbonyl-4-[2-(4-chloro-2-methyl-phenylsulfanyl)-phenyl]-piperidine-4-ol (intermediate for 1j)

1-tert-Butoxycarbonyl-4-[2-(4chloro-2-fluoro-phenylsulfanyl)-phenyl]-piperidine-4-ol (intermediate for 1k)

1-tert-Butoxycarbonyl-4-[2-(2,4-dichloro-phenylsulfanyl)-phenyl]-piperidine-4-ol (intermediate for 1l)

1-tert-Butoxycarbonyl-4-[2-(2-chloro-4-methoxy-phenylsulfanyl)-phenyl]-piperidine-4-ol (intermediate for 1m)

1-tert-Butoxycarbonyl-4-[2-(4-chloro-phenylsulfanyl)-phenyl]-piperidine-4-ol (intermediate for 2a).

1-tert-Butoxycarbonyl-4-[2-(4-methoxy-phenylsulfanyl)-5-fluoro-phenyl]-piperidine-4-ol (intermediate for 2b).

1-tert-Butoxycarbonyl-4-[2-(4-chloro-phenylsulfanyl)-5-fluoro-phenyl]-piperidine-4-ol (intermediate for 2c).

1-tert-Butoxycarbonyl-4-[2-(4-methoxphenylsulfanyl)-3-fluoro-phenyl]-piperidine-4-ol (intermediate for 2d)

1-tert-Butoxycarbonyl-4-[2-(2,4-dimethyl-phenylsulfanyl)-5-bromo-phenyl]-piperidine-4-ol (intermediate for 2e)

1-tert-Butoxycarbonyl-4-[2-(4methyl-phenylsulfanyl)-4-fluoro-phenyl]-piperidine-4-ol (intermediate for 2f)

1-tert-Butoxycarbonyl-4-[2-(4-chloro-phenylsulfanyl)-5-methyl-phenyl]-piperidine-4-ol (intermediate for 2g)

1-tert-Butoxycarbonyl-4-[2-(4-methyl-phenylsulfanyl)-5-trifluoromethyl-phenyl]-piperidine-4-ol (intermediate for 2h)

1-tert-Butoxycarbonyl-4-[2-(2,4-dimethyl-phenylsulfanyl)-5-fluoro-phenyl]-piperidine-4-ol (intermediate for 2i)

1-tert-Butoxycarbonyl-4-[2-(4-fluoro-phenylsulfanyl)-5-fluoro-phenyl]-piperidine-4-ol (intermediate for 2j)

1-tert-Butoxycarbonyl-4-[2-(2-chloro-4-fluoro-phenylsulfanyl)-5-fluoro-phenyl]-piperidine-4-ol (intermediate for 2k)

1-tert-Butoxycarbonyl-4-[2-(4-methyl-phenylsulfanyl)-5-fluoro-phenyl]-piperidine-4-ol (intermediate for 2l)

1-tert-Butoxycarbonyl-4-[2-(3-methoxy-phenylsulfanyl)-5-fluoro-phenyl]-piperidine-4-ol (intermediate for 2m)

1-tert-Butoxycarbonyl-4-[2-(2-chloro-4-methyl-phenylsulfanyl)-5-fluoro-phenyl]-piperidine-4-ol (intermediate for 2n)

1-tert-Butoxycarbonyl-4-[2-(2-chloro-4-methoxy-phenylsulfanyl)-5-fluoro-phenyl]-piperidine-4-ol (intermediate for 2o)

1-tert-Butoxycarbonyl-4-[2-(4-chloro-2-fluoro-phenylsulfanyl)-5-fluoro-phenyl]-piperidine-4-ol (intermediate for 2p)

1-tert-Butoxycarbonyl-4-[2-(2-fluoro-4-methyl-phenylsulfanyl)-5-fluoro-phenyl]-piperidine-4-ol (intermediate for 2q)

1-tert-Butoxycarbonyl-4-[2-(2-chloro-phenylsulfanyl)-5-fluoro-phenyl]-piperidine-4-ol (intermediate for 2r)

1-tert-Butoxycarbonyl-4-[2-(2,4-dichloro-phenylsulfanyl)-5-fluoro-phenyl]-piperidine-4-ol (intermediate for 2s).

1-tert-Butoxycarbonyl-4-[2-(2,4-difluoro-phenylsulfanyl)-5-fluoro-phenyl]-piperidine-4-ol (intermediate for 2t).

1-tert-Butoxycarbonyl-4-[2-(2,4-dimethyl-phenylsulfanyl)-3-fluoro-phenyl]-piperidine-4-ol (intermediate for 2u).

1-tert-Butoxycarbonyl-4-[2-(phenylsulfanyl)-5-fluoro-phenyl]-piperidine-4-ol (intermediate for 2v).

1-tert-Butoxycarbonyl-4-[2-(4-bromo-2-fluoro-phenylsulfanyl)-5-fluoro-phenyl]-piperidine-4-ol (intermediate for 2x).

Further intermediates for 2a1-2a6 were prepared from 4-hydroxy-4-(2-mercapto-5-fluoro-phenyl)-piperidine-1-carboxylic acid tert-butyl ester, and appropriately substituted aryliodides as detailed below by the palladium-catalysed coupling procedure described for 1-bromo-2-(4-chloro-phenylsulfanyl)-5-(trifluoromethyl)-benzene.

1-tert-Butoxycarbonyl-4-[2-(3-chloro-phenylsulfanyl)-5-fluoro-phenyl]-piperidine-4-ol (intermediate for 2a1). Prepared from 4-hydroxy-4-(2-mercapto-5-fluoro-phenyl)-piperidine-1-carboxylic acid tert-butyl ester and 1-chloro-3-iodo-benzene.

1-tert-Butoxycarbonyl-4-[2-(3-fluoro-phenylsulfanyl)-5-fluoro-phenyl]-piperidine-4-ol (intermediate for 2a2). Prepared from 4-hydroxy-4-(2-mercapto-5-fluoro-phenyl)-piperidine-1-carboxylic acid tert-butyl ester and 1-fluoro-3-iodo-benzene.

1-tert-Butoxycarbonyl-4-[2-(2-fluoro-4-methoxy-phenylsulfanyl)-5-fluoro-phenyl]-piperidine-4-ol (intermediate for 2a3). Prepared from 4-hydroxy-4-(2-mercapto-5-fluoro-phenyl)-piperidine-1-carboxylic acid tert-butyl ester and 2-fluoro-1-iodo-4-methoxy-benzene (prepared from 3-fluoro-4-nitro-phenol by reduction to 4-amino-3-fluoro-phenol as reported by Hogdson and Nicholson *J. Chem. Soc.* 1941, 645-646 followed by diazotization according to the general procedure by Tunney and Stille *J. Org. Chem.* 1987, 52, 748-753 followed by alkylation with methyl iodide according to the general procedure by Uozumi et al. *J. Org. Chem.* 1993, 58, 1945-1945).

1-tert-Butoxycarbonyl-4-[2-(4-methoxy-2-methyl-phenylsulfanyl)-5-fluoro-phenyl]-piperidine-4-ol (intermediate for 2a4). Prepared from 4-hydroxy-4-(2-mercapto-5-fluoro-phenyl)-piperidine-1-carboxylic acid tert-butyl ester and 1-iodo-4-methoxy-2-methyl-benzene (prepared from 4-methoxy-2-methyl-phenylamine by diazotization according to the general procedure by Tunney and Stille *J. Org. Chem.* 1987, 52, 748-753).

1-tert-Butoxycarbonyl-4-[2-(2-methyl-phenylsulfanyl)-5-fluoro-phenyl]-piperidine-4-ol (intermediate for 2a5). Prepared from 4-hydroxy-4-(2-mercapto-5-fluoro-phenyl)-piperidine-1-carboxylic acid tert-butyl ester and 1-iodo-2-methyl-benzene.

1-tert-Butoxycarbonyl-4-[2-(2-fluoro-phenylsulfanyl)-5-fluoro-phenyl]-piperidine-4-ol (intermediate for 2a6). Prepared from 4-hydroxy-4-(2-mercapto-5-fluoro-phenyl)-piperidine-1-carboxylic acid tert-butyl ester and 2-fluoro-1-iodo-benzene.

1-tert-Butoxycarbonyl-4-[2-(4-methoxycarbonyl-phenylsulfanyl)-phenyl]-piperidine-4-ol (intermediate for 4a) was prepared from 4-hydroxy-4-(2-mercapto-phenyl)-piperidine-1-carboxylic acid tert-butyl ester, and 4-iodo-benzoic acid methyl ester by the palladium-catalysed coupling procedure described for 1-bromo-2-(4-chloro-phenylsulfanyl)-5-(trifluoromethyl)-benzene.

COMPOUNDS OF THE INVENTION

Method A

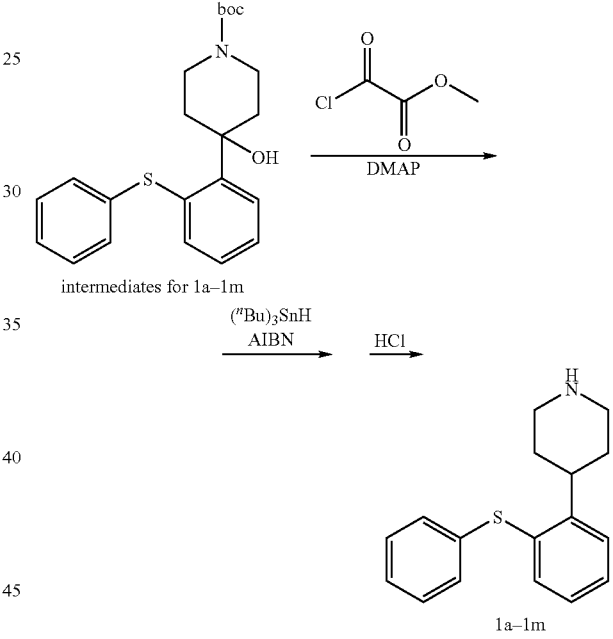

Example 1

1a, 4-[2-(4-Chloro-phenylsulfanyl)-5-trifluoromethyl-phenyl]-piperidine fumaric acid salt Chloro-oxo-acetic acid methyl ester (1.37 g, 11.2 mmol) was added to a stirred solution of 1-tert-butoxycarbonyl-4-[2-(4-chloro-phenylsulfanyl)-5-trifluoromethyl-phenyl]-piperidine-4-ol (0.98 g, 2.0 mmol) and dimethyl-pyridin-4-yl-amine (DMAP, 0.44 g, 3.6 mmol) in dry acetonitrile (6.4 mL) at 0° C. under argon. The reaction mixture was allowed to reach room temperature and then stirred overnight. Ethyl acetate (40 mL) was added and the precipitated salts were removed by filtration through celite. The organic phase was washed with saturated aqueous sodium bicarbonate (40 mL), saturated aqueous sodium chloride (40 mL), and dried over magnesium sulfate. The volatiles were evaporated off, and the crude material was dried in vacuo. This material was dissolved in dry toluene (13 mL) under argon. Tri-n-butyl tin hydride (0.81 g, 3.0 mmol) and 2-[(cyano-dimethyl-methyl)-azo]-2-methyl-propionitrile (AIBN, 82 mg, 0.5 mmol) were added. The solution was stirred under argon at 90° C. for 3.5 h. The solvent was evaporated, and the crude material was purified by chromatography on silica gel (eluent: ethyl acetate/heptane 1:9) to produce 4-[2-(4-chloro-phenylsulfanyl)-5-trifluoromethyl-phenyl]-piperidine-1-carboxylic acid tert-butyl ester as a clear oil (0.77 g, 82%). This oil was dissolved in methanol (8 mL) and hydrogen chloride in diethyl ether (2M, 8 mL) was added at 0° C. The reaction mixture was allowed to warm to room temperature and stirred overnight. The solvent was evaporated off and ethyl acetate (25 mL) was added. The organic phase was extracted with aqueous sodium hydroxide (2M, 8 mL) and washed with saturated aqueous sodium chloride (10 mL), dried over magnesium sulfate, and the solvent was evaporated off. This material (588 mg) was dissolved in ethyl acetate (2.2 mL) and fumaric acid (183 mg, 1.58 mmol) dissolved in hot ethanol (96%, 4.4 mL) was added. The target compound was collected as a white solid. LC/MS (m/z) 372.1 (MH$^+$); RT=2.54; purity (UV, ELSD): 97%, 100%; yield: 0.187 g (19%).

The following compounds of the invention 1b-1m were prepared analogously from the corresponding previously described intermediates:

1b, 4-[2-(4-Methoxy-phenylsulfanyl)-phenyl]-piperidine oxalic acid salt was collected as a white solid. LC/MS (m/z) 299.9 (MH$^+$); RT=2.04; purity (UV, ELSD): 95%, 97%; yield: 0.090 g (10%).

1c, 4-[2-(2,4-Dimethyl-phenylsulfanyl)-5-trifluoromethyl-phenyl]-piperidine oxalic acid salt was collected as a white solid. LC/MS (m/z) 366.2 (MH$^+$); RT=2.45; purity (UV, ELSD): 97%, 99%; yield: 0.61 g (45%).

1d, 4-[2-(4-Chloro-phenylsulfanyl)-4-fluoro-phenyl]-piperidine oxalic acid salt was collected as a white solid. LC/MS (m/z) 322.1 (MH$^+$); RT=2.33; purity (UV, ELSD): 83%, 97%; yield: 0.385 g (51%).

1e, 4-[2-(4-Methoxy-phenylsulfanyl)-4-fluoro-phenyl]-piperidine hydrochloric acid salt was collected as a white solid. LC/MS (m/z) 318.1 (MH$^+$); RT=2.12; purity (UV, ELSD): 96%, 99%; yield: 0.308 g (30%).

1f, 4-[2-(4-Methyl-phenylsulfanyl)-5-methyl-phenyl]-piperidine oxalic acid salt was collected as a white solid. LC/MS (n/z) 298.2 (MH$^+$); RT=2.29; purity (UV, ELSD): 98%, 99%; yield: 0.233 g (33%).

1g, 4-[2-(2,4-Dimethyl-phenylsulfanyl)-5-methyl-phenyl]-piperidine oxalic acid salt was collected as a white solid. LC/MS (m/z) 312.0 (MH$^+$); RT=2.41; purity (UV, ELSD): 98%, 100%; yield: 0.233 g (33%).

1h, 4-[2-(4-Fluoro-2-methyl-phenylsulfanyl)-5-methyl-phenyl]-piperidine oxalic acid salt was isolated as a white solid. LC/MS (m/z) 316.0 (MH$^+$); RT=2.33; purity (UV, ELSD): 96%, 100%; yield: 0.336 g (34%).

1i, 4-[2-(4-Methoxy-phenylsulfanyl)-5-methyl-phenyl]-piperidine oxalic acid salt was collected as a white solid. LC/MS (m/z) 313.8 (MH$^+$); RT=2.16; purity (UV, ELSD): 96%, 99%; yield: 0.375 g (34%).

1j, 4-[2-(4-Chloro-2-methyl-phenylsulfanyl)-phenyl]-piperidine trifluoro-acetic acid salt was collected as a clear oil. LC/TOF (m/z) 318.0 (MH$^+$); RT=2.36; purity (UV, ELSD): 99.7%, 99.0%.

1k, 4-[2-(4-Chloro-2-fluoro-phenylsulfanyl)-phenyl]-piperidine trifluoro-acetic acid salt was collected as a clear oil. LC/MS (m/z) 322.0 (MH$^+$); RT=2.27; purity (UV, ELSD): 94.6%, 99.7%.

1l, 4-[2-(2,4-Dichloro-phenylsulfanyl)-phenyl]-piperidine trifluoro-acetic acid salt was collected as a clear oil. LC/MS (m/z) 337.9 (MH$^+$); RT=2.37; purity (UV, ELSD): 94.9%, 99.6%.

1m, 4-[2-(2-Chloro-4-methoxy-phenylsulfanyl)-phenyl]-piperidine trifluoro-acetic acid salt was collected as a clear oil. LC/MS (m/z) 334.0 (MH$^+$); RT2.23; purity (UV, ELSD): 95.9, 99.9.

Method B

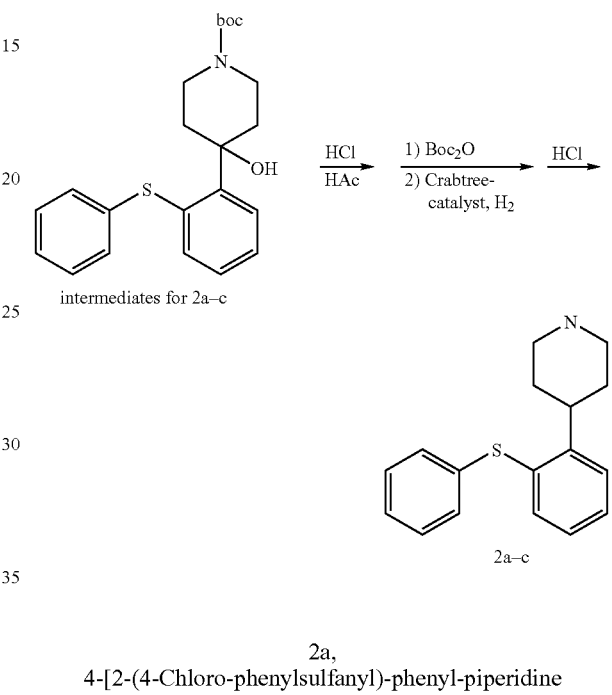

2a,
4-[2-(4-Chloro-phenylsulfanyl)-phenyl-piperidine oxalic acid salt

Concentrated aqueous hydrochloric acid (150 mL) was added to a stirred solution of 1-tert-butoxycarbonyl-4-[2-(4-chloro-phenylsulfanyl)-phenyl]-piperidine-4-ol (12.13 g, 28.9 mmol) in acetic acid (450 mL). The solution was refluxed overnight, cooled to room temperature and then stirred on an ice bath. A saturated aqueous solution of sodium hydroxide (250 mL) was slowly added and the unclear solution was extracted with ethyl acetate (3×450 mL). The combined organic phases were washed with saturated aqueous sodium chloride (450 mL), dried over magnesium sulfate and the solvents evaporated off. The crude material (8.02 g) was dissolved in THF (195 mL) and di-tert-butyl dicarbonate (Boc$_2$O, 6.96 g, 31.9 mmol) and triethyl amine (5 mL) were added. The mixture was stirred overnight and then quenched by addition of saturated aqueous ammonium chloride (200 mL). The organic phase was dried over magnesium sulfate, and the solvent was evaporated off. The crude material was purified by chromatography on silica gel (eluent: An increasing amount of ethyl acetate (0-20%) in heptane) to produce 4-[2-(4-chloro-phenylsulfanyl)-phenyl]-piperidine-1-carboxylic acid tert-butyl ester as a white solid (5.63 g). This material was dissolved in methylene chloride (130 mL). Hydrogen gas (3 bar) was bubbled through the solution using a Parr shaker apparatus and (1,5-cyclooctadiene)(pyridine)(tricyclohexylphosphine)(hexafluorophosphine) iridium(I) (Crabtree's catalyst, 0.495 g, 1.40 mmol) was added and the hydrogenation was allowed to continue overnight. The catalyst was filtered off and the crude product was purified by chromatography on silica gel (eluent: An increasing amount of ethyl acetate (0-20%) in heptane) to produce 4-[2-(4-chloro-phenylsulfanyl)-phenyl]-piperidine-1-carboxylic acid tert-butyl ester (5.37 g). This material was dissolved in methanol (70 mL) and hydrogen chloride in diethyl ether (2M, 67 mL, 133 mmol) was added and the reaction mixture was stirred overnight. The solvent was evaporated off, and aqueous sodium hydroxide (2M, 200 mL), and ethyl acetate (400 mL) were added. The phases were separated, and the aqueous phase was extracted with ethyl acetate (400 mL). The combined organic phases were washed with saturated aqueous sodium chloride (300 mL), dried over magnesium sulfate, and the solvent was evaporated off. The residue was purified by chromatography on silica gel (eluent: An increasing amount of ethanol (0-25%) in ethyl acetate containing 5% triethyl-amine) to produce 4-[2-(4-chloro-phenylsulfanyl)-phenyl]-piperidine (1.63 g). This material was dissolved in THF at 50° C. and a solution of oxalic acid (0.48 g) in THF was slowly added. 4-[2-(4-chloro-phenylsulfanyl)-phenyl]-piperidine oxalic acid salt was collected as a white solid. LC/MS (m/z) 304.0 (MH$^+$); RT=2.29; purity (UV, ELSD): 96%, 96%; yield: 1.86 g (15%).

The following compounds of the invention 2b-2x and 2a1-2a6 were prepared analogously from the corresponding previously described intermediates:

2b, 4-[2-(4-Methoxy-phenylsulfanyl)-5-fluoro-phenyl]-piperidine oxalic acid salt was collected as a white solid. LC/MS (m/z) 318.1 (MH$^+$); RT=2.16; purity (UV, ELSD): 91%, 98%.

2c, 4-[2-(4-Chloro-phenylsulfanyl)-5-fluoro-phenyl]-piperidine oxalic acid salt was collected as a white solid. LC/MS (m/z) 321.9 (MH$^+$); RT=2.33; purity (UV, ELSD): 94%, 96%; yield: 0.241 g.

2d, 4-[2-(4-Methoxy-phenylsulfanyl)-3-fluoro-phenyl]-piperidine oxalic acid salt was collected as a white solid. LC/MS (m/z) 318.1 (MH$^+$); RT=2.12; purity (UV, ELSD): 98.6%, 98.5%.

2e, 4-[2-(2,4-Dimethyl-phenylsulfanyl)-5-bromo-phenyl]-piperidine fumaric acid salt was collected as a white solid. LC/MS (m/z) 378.0 (MH$^+$); RT=2.50; purity (UV, ELSD): 99.3%, 98.5%.

2f, 4-[2-(4-Methyl-phenylsulfanyl)-4-fluoro-phenyl]-piperidine trifluoro-acetic acid salt was collected as a clear oil. LCMS (m/z) 302.1 (MH$^+$); RT=2.12; purity (UV, ELSD): 73.3%, 97.9%.

2g, 4-[2-(4-Chloro-phenylsulfanyl)-5-methyl-phenyl]-piperidine trifluoro-acetic acid salt was collected as a clear oil. LC/MS (m/z) 317.0 (MH$^+$); RT=2.41; purity (UV, ELSD): 94.9%, 99.8%.

2h, 4-[2-(4-Methyl-phenylsulfanyl)-5-trifluoromethyl-phenyl]-piperidine trifluoro-acetic acid salt was collected as a clear oil. LC/MS (m/z) 352.2 (MH$^+$); RT=2.49; purity (UV, ELSD): 95.0%, 99.8%.

2i, 4-[2-(2,4-Dimethyl-phenylsulfanyl)-5-fluoro-phenyl]-piperidine oxalic acid salt was collected as a white solid. LC/MS (m/z) 316.1 (MH$^+$); RT=2.38; purity (UV, ELSD): 95.1%, 100%.

2j, 4-[2-(4-Fluoro-phenylsulfanyl)-5-fluoro-phenyl]-piperidine oxalic acid salt was collected as a white solid. LC/MS (m/z) 306.0 (MH$^+$); RT=2.10; purity (UV, ELSD): 88.1%, 97.6%.

2k, 4-[2-(2-Chloro-4-fluoro-phenylsulfanyl)-5-fluoro-phenyl]-piperidine oxalic acid salt was collected as a white solid. LC/MS (m/z) 340.0 (MH$^+$); RT=2.20; purity (UV, ELSD): 95.1%, 100%.

2l, 4-[2-(4-Methyl-4-phenylsulfanyl)-5-fluoro-phenyl]-piperidine fumaric acid salt was collected as a white solid. LC/MS (m/z) 302.0 (MH$^+$); RT=2.26; purity (UV, ELSD): 96%, 99.7%.

2m, 4-[2-(3-Methoxy-phenylsulfanyl)-5-fluoro-phenyl]-piperidine oxalic acid salt was collected as a white solid. LC/MS (m/z) 318.0 (MH$^+$); RT=2.17; purity (UV, ELSD): 91.1%, 97.1%.

2n, 4-[2-(2-Chloro-4-methyl-phenylsulfanyl)-5-fluoro-phenyl]-piperidine fumaric acid salt was collected as a white solid. LC/MS (m/z) 335.9 (MH$^+$); RT=2.24; purity (UV, ELSD): 95.8%, 99.6%.

2o, 4-[2-(2-Chloro-4-methoxy-phenylsulfanyl)-5-fluoro-phenyl]-piperidine fumaric acid salt was collected as a white solid. LC/MS (m/z) 352.2 (MH$^+$); RT=2.27; purity (UV, ELSD): 95.8%, 97.2%.

2p, 4-[2-(4-Chloro-2-fluoro-phenylsulfanyl)-5-fluoro-phenyl]-piperidine fumaric acid salt was collected as a white solid. LC/MS (m/z) 340.0 (MH$^+$); RT=2.25; purity (UV, ELSD): 97.4%, 99.9%.

2q, 4-[2-(2-Fluoro-4-methyl-phenylsulfanyl)-5-fluoro-phenyl]-piperidine fumaric acid salt was collected as a white solid. LC/MS (m/z) 320.0 (MH$^+$); RT=2.22; purity (UV, ELSD): 92.7%, 97.1%.

2r, 4-[2-(2-Chloro-phenylsulfanyl)-5-fluoro-phenyl]-piperidine hydrobromic acid salt was collected as a clear oil. LC/MS (m/z) 321.9 (MH$^+$); RT=2.14 min; purity (UV, ELSD): 72.0%, 96.6%.

2s, 4-[2-(2,4-Dichloro-phenylsulfanyl)-5-fluoro-phenyl]-piperidine fumaric acid salt was collected as a white solid. LC/MS (m/z) 358.0 (MH$^+$); RT=2.34; purity (UV, ELSD): 97%, 99%.

2t, 4-[2-(2,4-Difluoro-phenylsulfanyl)-5-fluoro-phenyl]-piperidine fumaric acid salt was collected as a white solid. LC/MS (m/z) 324.0 (MH$^+$); RT=2.11; purity (UV, ELSD): 97.0%, 100%.

2u, 4-[2-(2,4-Dimethyl-phenylsulfanyl)-3-fluoro-phenyl]-piperidine trifluoro-acetic acid salt was collected as a clear oil. LC/NS (m/z) 314.0 (MH$^+$); RT=2.33; purity (UV, ELSD): 85.3%, 98.5%.

2v, 4-[2-(Phenylsulfanyl)-5-fluoro-phenyl]-piperidine trifluoro-acetic acid salt was collected as a clear oil. LC/MS (m/z) 288.0 (MH$^+$); RT=2.06; purity (UV, ELSD): 98.6%, 99.4%.

2x, 4-[2-(4-Bromo-2-fluoro-phenylsulfanyl)-5-fluoro-phenyl]-piperidine trifluoro-acetic acid salt was collected as a clear oil. LC/MS (m/z) 386.0 (MH$^+$); RT=2.16; purity (UV, ELSD): 96.7%, 99.3%.

2a1, 4-[2-(3-Chloro-phenylsulfanyl)-5-fluoro-phenyl]-piperidine oxalic acid salt was collected as a white solid. LC/MS (m/z) 322.0 (MH$^+$); RT=2.22; purity (UV, ELSD): 95.4%, 89%.

2a2, 4-[2-(3-Fluoro-phenylsulfanyl)-5-fluoro-phenyl]-piperidine oxalic acid salt was collected as a clear oil. LC/MS (m/z) 306.0 (MH$^+$); RT=2.23; purity (UV, ELSD): 90%, 99%.

2a3, 4-[2-(2-Fluoro-4-methoxy-phenylsulfanyl)-5-fluoro-phenyl]-piperidine fumaric acid salt was collected as a white solid. LC/MS (m/z) 336.0 (MH$^+$); RT=2.06; purity (UV, ELSD): 97.3%, 99.9%.

2a4, 4-[2-(2-Methyl-4-methoxy-phenylsulfanyl)-5-fluoro-phenyl]-piperidine trifluoro-acetic acid salt was collected as a clear oil. LC/MS (m/z) 332.0 (MH$^+$); RT=2.16; purity (UV, ELSD): 96%, 100%.

2a5, 4-[2-(2-Methyl-phenylsulfanyl)-5-fluoro-phenyl]-piperidine fumaric acid salt was collected as a white solid. LC/MS (m/z) 302.1 (MH$^+$); RT=2.20; purity (UV, ELSD): 79.9%, 99.0%.

2a6, 4-[2-(2-Fluoro-phenylsulfanyl)-5-fluoro-phenyl]-piperidine hydrobromic acid salt was collected as a clear oil. LC/MS (m/z) 306.0 (MH$^+$); RT=2.17; purity (UV, ELSD): 86.7%, 94.0%.

Method C

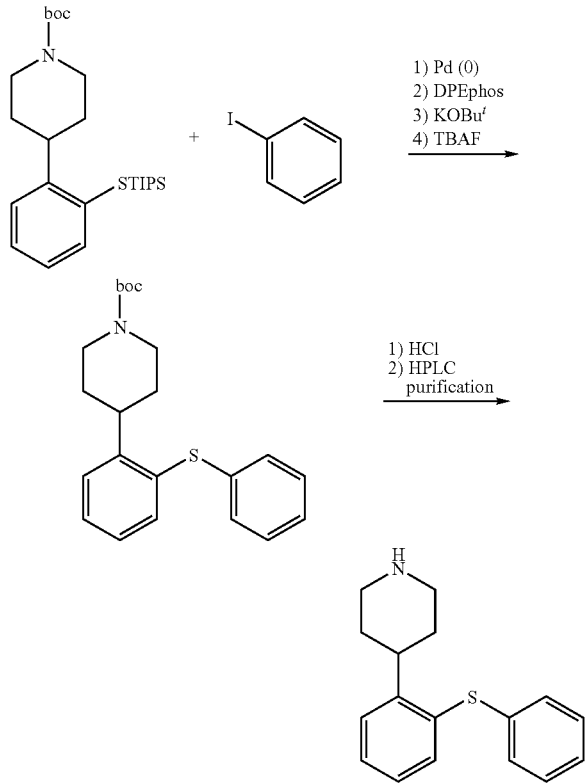

3a1, 4-[2-(4-Trifluoromethyl-phenylsulfanyl)-phenyl]-piperidine trifluoro-acetic acid salt A mixture of 4-(2-tri-iso-propylsilanylsulfanyl-phenyl)-piperidine-1-carboxylic acid tert-butyl ester (38 mg, 0.085 mmol) and 1-iodo-4-trifluoromethyl-benzene (23 mg, 0.085 mmol) was dissolved in dry degassed toluene (0.3 mL). Pd$_2$dba$_3$ (1 mg) and DPEphos (1 mg) dissolved in dry toluene (0.2 mL) were added. To this solution were added potassium tert-butoxide (10 mg) and tetra-n-butyl ammonium fluoride (TBAF, 1M in TBF, 0.1 mL, 0.1 mmol) and the reaction mixture was stirred at 110° C. for 1 h under argon. The solution was filtered and the solvent was evaporated off. The crude product was purified by chromatography on silica gel (eluent: An increasing amount (0-100%) of ethyl acetate in heptane) to produce 4-[2-(4-trifluoromethyl-phenylsulfanyl)-phenyl]-piperidine-1-carboxylic acid tert-butyl ester (3a1) as a clear oil (22 mg, 59% yield). This material was dissolved in methanol (1 mL) and hydrogen chloride in diethyl ether (2M, 1 mL) was added and the solution was stirred overnight at rt. The solvent was evaporated of and the crude product was purified by BPLC (containing 0.1% TFA in the standard eluent) to produce 4-[2-(4-trifluoromethyl-phenylsulfanyl)-phenyl]-piperidine 3a1 as the trifluoro-acetic acid salt. Yield: 3.2 mg (8% overall). LC/TOF (m/z) 338.0 (MH$^+$); RT=2.29 min; purity (UV, ELSD): 98.3%, 97.1%.

The following compounds of the invention 3a1-3a6 (prepared from 4-(2-tri-iso-propylsilanylsulfanyl-phenyl)-piperidine-1-carboxylic acid tert-butyl ester) 3b1-3b12 (prepared from 4-(2-tri-iso-propylsilanylsulfanyl-5-methyl-phenyl)-piperidine-1-carboxylic acid tert-butyl ester) 3c1-3c4 (prepared from 4-(2-tri-iso-propylsilanylsulfanyl-5-methoxy-phenyl)-piperidine-1-carboxylic acid tert-butyl ester) 3d1-3d27 (prepared from 4-(2-fluoro-6-tri-iso-propylsilanylsulfanyl-phenyl)-piperidine-1-carboxylic acid tert-butyl ester) 3e1-3e10 (prepared from 4-(5-fluoro-2-tri-iso-propylsilanylsulfanyl-phenyl)-piperidine-1-carboxylic acid tert-butyl ester) 3f1-3f13 (prepared from 4-(4-fluoro-2-tri-iso-propylsilanylsulfanyl-phenyl)-piperidine-1-carboxylic acid tert-butyl ester) were prepared analogously:

3a2, 4-[2-(2-Chloro-4-fluoro-phenylsulfanyl)-phenyl]-piperidine trifluoro-acetic acid salt was prepared from 2-chloro-4-fluoro-1-iodo-benzene and collected as a clear oil (5.0 mg). LC/TOF (m/z) 322.0 (MH$^+$); RT=2.27 min; purity (UV, ELSD): 98.4%, 97.7%.

3a3, 4-[2-(4-Methoxy-2-methyl-phenylsulfanyl)-phenyl]-piperidine trifluoro-acetic acid salt was prepared from 1-iodo-4-methoxy-2-methyl-benzene was and collected as a clear oil (5.8 mg). LC/MS (m/z) 314.0 (MH$^+$); RT=2.24 min; purity (UV, ELSD): 98.4%, 100%.

3a4, 4-[2-(2,4-Difluoro-phenylsulfanyl)-phenyl]-piperidine trifluoro-acetic acid salt was prepared from and 2,4-difluoro-1-iodo-benzene and collected as a clear oil (3.7 mg). LC/MS (m/z) 306.0 (MH$^+$); RT=2.24 min; purity (UV, ELSD): 97.9%, 100%.

3a5, 4-[2-(2,3-Dimethyl-phenylsulfanyl)-phenyl]-piperidine trifluoro-acetic acid salt was prepared from 1-iodo-2,3-dimethyl-benzene and collected as a clear oil (6.0 mg). LC/MS (m/z) 298.1 (MH$^+$); RT=2.37 min; purity (UV, ELSD): 95.9%, 95.9%.

3a6, 4-[2-(3,4-Dimethyl-phenylsulfanyl)-phenyl]-piperidine trifluoro-acetic acid salt was prepared from 4-iodo-1,2-dimethyl-benzene and collected as a clear oil (4.2 mg). LC/MS (m/z) 298.0 (MH$^+$); RT=2.37 min; purity (UV, ELSD): 96.6%, 100%.

3b1, 4-[2-(2-Chloro-4-methoxy-phenylsulfanyl)-5-methyl-phenyl]-piperidine trifluoro-acetic acid salt was prepared from 2-chloro-1-iodo-4-methoxy-benzene and collected as a clear oil (3.8 mg). LC/MS (m/z) 347.9 (MH$^+$); RT=2.28 min; purity (UV, ELSD): 92.3%, 100%.

3b2, 4-[2-(2-Chloro-4-methyl-phenylsulfanyl)-5-methyl-phenyl]-piperidine trifluoro-acetic acid salt was prepared from 2-chloro-1-iodo-4-methyl-benzene and collected as a clear oil (4.4 mg). LC/MS (m/z) 331.9 (MH$^+$); RT=2.39 min; purity (UV, ELSD): 97.3%, 100%.

3b3, 4-[2-(2-Fluoro-4-methyl-phenylsulfanyl)-5-methyl-phenyl]-piperidine trifluoro-acetic acid salt was prepared from 2-fluoro-1-iodo-4-methyl-benzene and collected as a clear oil (4.3 mg). LC/MS (m/z) 315.9 (MH$^+$); RT=2.30 min; purity (UV, ELSD): 85.8%, 100%.

3b4, 4-[2-(4-Fluoro-3-methoxy-phenylsulfanyl)-5-methyl-phenyl]-piperidine trifluoro-acetic acid salt was prepared from 2-fluoro-4-iodo-1-methoxy-benzene (prepared from 3-fluoro-4-methoxy-phenylamine by diazotization according to the general procedure by Tunney and Stille *J. Org. Chem.* 1987, 52, 748-753) and collected as a clear oil (4.3 mg). LC/MS (m/z) 332.0 (MH$^+$); RT=2.20 min; purity (UV, ELSD): 88.1%, 100%.

3b5, 4-[2-(3-Fluoro-2-methyl-phenylsulfanyl)-5-methyl-phenyl]-piperidine trifluoro-acetic acid salt was prepared from 1-fluoro-3-iodo-2-methyl-benzene and collected as a clear oil (5.2 mg). LC/MS (m/z) 315.9 (MH$^+$); RT=2.34 min; purity (UV, ELSD): 88.9%, 97.5%.

3b6, 4-[2-(3-Fluoro-4-methyl-phenylsulfanyl)-5-methyl-phenyl]-piperidine trifluoro-acetic acid salt was prepared from 2-fluoro-4-iodo-1-methyl-benzene and collected as a clear oil (6.1 mg). LC/MS (m/z) 316.0 (MH$^+$); RT=2.34 min; purity (UV, ELSD): 99.1%, 100%.

3b7, 4-[2-(5-Chloro-2-fluoro-phenylsulfanyl)-5-methyl-phenyl]-piperidine trifluoro-acetic acid salt was prepared from 4-chloro-1-fluoro-2-iodo-benzene and collected as a clear oil (5.8 mg). LC/MS (m/z) 336.1 (MH$^+$); RT=2.34 min; purity (UV, ELSD): 92.6%, 99.9%.

3b8, 4-[2-(2-Chloro-4-fluoro-phenylsulfanyl)-5-methyl-phenyl]-piperidine trifluoro-acetic acid salt was prepared from 2-chloro-4-fluoro-1-iodo-benzene and collected as a clear oil (6.0 mg). LC/MS (m/z) 336.1 (MH$^+$); RT=2.34 min; purity (UV, ELSD): 98.0%, 100%.

3b9, 4-[2-(3-Methoxy-phenylsulfanyl)-5-methyl-phenyl]-piperidine trifluoro-acetic acid salt was prepared from 1-iodo-3-methoxy-benzene and collected as a clear oil (4.0 mg). LC/MS (m/z) 313.9 (MH$^+$); RT=2.18 min; purity (UV, ELSD): 92.6%, 99.9%.

3b10, 4-[2-(4-Chloro-2-fluoro-phenylsulfanyl)-5-methyl-phenyl]-piperidine trifluoro-acetic acid salt was prepared from 4-chloro-2-fluoro-1-iodo-benzene and collected as a clear oil (6.1 mg). LC/MS (m/z) 336.2 (MH$^+$); RT=2.37 min; purity (UV, ELSD): 93.4%, 99.9%.

3b11, 4-[2-(3-Chloro-2-fluoro-phenylsulfanyl)-5-methyl-phenyl]-piperidine trifluoro-acetic acid salt was prepared from and 1-chloro-2-fluoro-3-iodo-benzene and collected as a clear oil (6.3 mg). LC/MS (m/z) 336.0 (MH$^+$); RT=2.35 min; purity (UV, ELSD): 97.8%, 99.8%.

3b12, 4-[2-(2,4-Difluoro-phenylsulfanyl)-5-methyl-phenyl]-piperidine trifluoro-acetic acid salt was prepared from 2,4-difluoro-1-iodo-benzene and collected as a clear oil (3.7 mg). LC/MS (m/z) 319.7 (MH$^+$); RT=2.22 min; purity (UV, ELSD): 92.5%, 99.9%.

3c1, 4-[2-(4-Methyl-phenylsulfanyl)-5-methoxy-phenyl]-piperidine trifluoro-acetic acid salt was prepared from 1-iodo-4-methyl-benzene and collected as a clear oil (2.6 mg). LC/MS (m/z) 314.1 (MH$^+$); RT=2.21 min; purity (UV, ELSD): 89.2%, 100%.

3c2, 4-[2-(4-Fluoro-phenylsulfanyl)-5-methoxy-phenyl]-piperidine trifluoro-acetic acid salt was prepared from 1-fluoro-4-iodo-benzene and collected as a clear oil (2.1 mg). LC/MS (m/z) 318.1 (MH$^+$); RT=2.13 min; purity (UV, ELSD): 80.9%, 99.2%.

3c3, 4-[2-(2-Methyl-4-methoxy-phenylsulfanyl)-5-methoxy-phenyl]-piperidine trifluoro-acetic acid salt was prepared from 4iodo-2-methyl-1-methoxy-benzene (prepared from 2-methyl-4-methoxy-phenylamine by diazotization according to the general procedure by Tunney and Stille *J. Org. Chem.* 1987, 52, 748-753) and collected as a clear oil (2.5 mg). LC/MS (m/z) 344.1 (MH$^+$); RT=2.17 min; purity (UV, ELSD): 93.6%, 99.8%.

3c4, 4-[2-(4-Fluoro-2-methyl-phenylsulfanyl)-5-methoxy-phenyl]-piperidine trifluoro-acetic acid salt was prepared from 4-fluoro-1-iodo-2-methyl-benzene and collected as a clear oil (2.2 mg). LC/MS (m/z) 332.0 (MH$^+$); RT=2.25 min; purity (UV, ELSD): 87.6%, 75.3%.

3d1, 4-[2-(3-Methoxy-phenylsulfanyl)-6-fluoro-phenyl]-piperidine trifluoro-acetic acid salt was prepared from 1-iodo-3-methoxy-benzene and collected as a clear oil (2.3 mg). LC/MS (m/z) 332.0 (MH$^+$); RT=2.03 min; purity (UV, ELSD): 98.7%, 100%.

3d2, 4-[2-(2-Methyl-phenylsulfanyl)-6-fluoro-phenyl]-piperidine trifluoro-acetic acid salt was prepared from 1-iodo-4-methyl-benzene and collected as a clear oil (2.1 mg). LC/MS (m/z) 302.1 (MH$^+$); RT=2.12 min; purity (UV, ELSD): 97.8%, 99.9%.

3d3, 4-[2-(3-Methyl-phenylsulfanyl)-6-fluoro-phenyl]-piperidine trifluoro-acetic acid salt was prepared from 1-iodo-3-methyl-benzene and collected as a clear oil (3.6 mg). LC/MS (m/z) 302.2 (MH$^+$); RT=2.14 min; purity (UV, ELSD): 97.4%, 100%.

3d4, 4-[2-(4-Methoxy-2-methyl-phenylsulfanyl)-6-fluoro-phenyl]-piperidine trifluoro-acetic acid salt was prepared from 4-iodo-2-methyl-1-methoxy-benzene prepared from 2-methyl-4-methoxy-phenylamine by diazotization according to the general procedure by Tunney and Stille *J. Org. Chem.* 1987, 52, 748-753) and collected as a clear oil (2.2 mg). LC/MS (m/z) 332.1 (MH$^+$); RT=2.14 min; purity (UV, ELSD): 96.9%, 100%.

3d5, 4-[2-(2-Methoxy-phenylsulfanyl)-6-fluoro-phenyl]-piperidine trifluoro-acetic acid salt was prepared from 1-iodo-2-methoxy-benzene and collected as a clear oil (1.7 mg). LC/MS (m/z) 317.9 (MH$^+$); RT=1.98 min; purity (UV, ELSD): 98.7%, 100%.

3d6, 4-[2-(4-Fluoro-2-Methyl-phenylsulfanyl)-6-fluoro-phenyl]-piperidine trifluoro-acetic acid salt was prepared from 4-fluoro-1-iodo-2-methyl-benzene and collected as a clear oil (2.3 mg). LC/MS (m/z) 332.0 (MH$^+$); RT=2.16 min; purity (UV, ELSD): 96.3%, 100%.

3d7, 4-[2-(3-Fluoro-4-methyl-phenylsulfanyl)-6-fluoro-phenyl]-piperidine trifluoro-acetic acid salt was prepared from 2-fluoro-4-iodo-1-methyl-benzene and collected as a clear oil (1.9 mg). LC/MS (m/z) 320.0 (MH$^+$); RT=2.21 min; purity (UV, ELSD): 96.1%, 100%.

3d8, 4-[2-(2, 3-Dimethyl-phenylsulfanyl)-6-fluoro-phenyl]-piperidine trifluoro-acetic acid salt was prepared from 1-iodo-2,3-dimethyl-benzene and collected as a clear oil (1.7 mg). LC/MS (m/z) 315.9 (MH$^+$); RT=2.23 min; purity (UV, ELSD): 95.8%, 100%.

3d9, 4-[2-(3-Fluoro-2-methyl-phenylsulfanyl)-6-fluoro-phenyl]-piperidine trifluoro-acetic acid salt was prepared from 1-fluoro-3-iodo-2-methyl-benzene and collected as a clear oil (1.8 mg). LC/MS (m/z) 319.9 (MH$^+$); RT=2.18 min; purity (UV, ELSD): 94.6%, 100%.

3d10, 4-[2-(3-Chloro-phenylsulfanyl)-6-fluoro-phenyl]-piperidine trifluoro-acetic acid salt was prepared from 1-chloro-3-iodo-benzene and collected as a clear oil (1.7 mg). LC/MS (m/z) 321.9 (MH$^+$); RT=2.15 min; purity (UV, ELSD): 94.1%, 99.6%.

3d11, 4-[2-(3-Fluoro-phenylsulfanyl)-6-fluoro-phenyl]-piperidine trifluoro-acetic acid salt was prepared from 1-fluoro-3-iodo-benzene and collected as a clear oil (3.4 mg). LC/MS (m/z) 305.8 RT=2.04 min; purity (UV, ELSD): 92.6%, 100%.

3d12, 4-[2-(2-Fluoro-phenylsulfanyl)-6-fluoro-phenyl]-piperidine trifluoro-acetic acid salt was prepared from 1-fluoro-2-iodo-benzene and collected as a clear oil (3.5 mg). LC/MS (m/z) 305.9 (MH$^+$); RT=2.00 min; purity (UV, ELSD): 92.5%, 99.9%.

3d13, 4-[2-(4-Fluoro-3-methoxy-phenylsulfanyl)-6-fluoro-phenyl]-piperidine trifluoro-acetic acid salt was prepared from 1-fluoro-4-iodo-2-methoxy-benzene (prepared from 4-fluoro-3-methoxy-phenylamine by diazotization according to the general procedure by Tunney and Stille *J. Org. Chem.* 1987, 52, 748-753) and collected as a clear oil (1.2 mg). LC/MS (m/z) 336.0 (MH$^+$); RT=2.07 min; purity (UV, ELSD): 91.7%, 100%.

3d14, 4-[2-(2-Chloro-4-methyl-phenylsulfanyl)-6-fluoro-phenyl]-piperidine trifluoro-acetic acid salt was prepared from 2-chloro-1-iodo-4-methyl-benzene and collected as a clear oil (2.5 mg). LC/MS (m/z) 336.2 (MH$^+$); RT=2.24 min; purity (UV, ELSD): 91.6%, 96.3%.

3d15, 4-[2-(4-Chloro-2-fluoro-phenylsulfanyl)-6-fluoro-phenyl]-piperidine trifluoro-acetic acid salt was prepared from 4-chloro-2-fluoro-1-iodo-benzene and collected as a clear oil (1.7 mg). LC/MS (m/z) 340.0 (MH$^+$); RT=2.20 min; purity (UV, ELSD): 91.5%, 99.9%.

3d16, 4-[2-(4-Trifluoromethyl-phenylsulfanyl)-6-fluoro-phenyl]-piperidine trifluoro-acetic acid salt was prepared from 1-iodo-4-trifluoromethyl-benzene was and collected as a clear oil (2.0 mg). LC/MS (m/z) 356.2 (MH$^+$); RT=2.29 min; purity (UV, ELSD): 91.5%, 93.4%.

3d17, 4-[2-(3-Chloro-2-fluoro-phenylsulfanyl)-6-fluoro-phenyl]-piperidine trifluoro-acetic acid salt was prepared from 1-chloro-2-fluoro-3-iodo-benzene and collected as a clear oil (1.2 mg). LC/MS (m/z) 340.1 (MH$^+$); RT=2.17 min; purity (UV, ELSD): 90.8%, 99.7%.

3d18, 4-[2-(4-Methyl-phenylsulfanyl)-6-fluoro-phenyl]-piperidine trifluoro-acetic acid salt was prepared from 1-iodo-4-methyl-benzene and collected as a clear oil (3.2 mg). LC/MS (m/z) 302.1 (MH$^+$); RT=2.15 min; purity (UV, ELSD): 89.9%, 98.7%.

3d19, 4-[2-(4-Chloro-phenylsulfanyl)-6-fluoro-phenyl]-piperidine trifluoro-acetic acid salt was prepared from 1-chloro-4-iodo-benzene and collected as a clear oil (2.6 mg). LC/MS (m/z) 321.7 (MH$^+$); RT=2.19 min; purity (UV, ELSD): 89.3%, 100%.

3d20, 4-[2-(3,4-Dimethyl-phenylsulfanyl)-6-fluoro-phenyl]-piperidine trifluoro-acetic acid salt was prepared from 4-iodo-1,2-dimethyl-benzene and collected as a clear oil (2.5 mg). LC/MS (m/z) 316.0 (MH$^+$); RT=2.26 min; purity (UV, ELSD): 89.1%, 99.5%.

3d21, 4-[2-(2-Fluoro-4-methyl-phenylsulfanyl)-6-fluoro-phenyl]-piperidine trifluoro-acetic acid salt was prepared from 2-fluoro-1-iodo-4-methyl-benzene and collected as a clear oil (2.9 mg). LC/MS (m/z) 319.9 (MH$^+$); RT=2.13 min; purity (UV, ELSD): 89.0%, 100%.

3d22, 4-[2-(2,4-Dichloro-phenylsulfanyl)-6-fluoro-phenyl]-piperidine trifluoro-acetic acid salt was prepared from 2,4-dichloro-1-iodo-benzene and collected as a clear oil (3.1 mg). LC/MS (m/z) 356.1 (MH$^+$); RT=2.31 min; purity (UV, ELSD): 87.9%, 100%.

3d23, 4-[2-(2-Fluoro-4-methoxy-phenylsulfanyl)-6-fluoro-phenyl]-piperidine trifluoro-acetic acid salt was prepared from 2-fluoro-1-iodo-4-methoxy-benzene (MOJJ-MOJJ) and collected as a clear oil (1.1 mg). LC/MS (m/z) 336.1 (MH$^+$); RT=2.05 min; purity (UV, ELSD): 86.0%, 100%.

3d24, 4-[2-(2,4-Difluoro-phenylsulfanyl)-6-fluoro-phenyl]-piperidine trifluoro-acetic acid salt was prepared from 2,4-difluoro-1-iodo-benzene and collected as a clear oil (1.0 mg). LC/MS (m/z) 324.1 (MH$^+$); RT=2.05 min; purity (UV, ELSD): 85.8%, 99.9%.

3d25, 4-[2-(2-Chloro-4-methoxy-phenylsulfanyl)-6-fluoro-phenyl]-piperidine trifluoro-acetic acid salt was prepared from 2-chloro-1-iodo-4-methoxy-benzene (prepared from 2-chloro-4-methoxy-phenylamine by diazotization according to the general procedure by Tunney and Stille *J. Org. Chem.* 1987, 52, 748-753) and collected as a clear oil (2.8 mg). LC/MS (m/z) 352.2 (MH$^+$); RT=2.16 min; purity (UV, ELSD): 85.3%, 98.9%.

3d26, 4-[2-(4-Methoxy-phenylsulfanyl)-6-fluoro-phenyl]-piperidine trifluoro-acetic acid salt was prepared from 1-iodo-4-methoxy-benzene and collected as a clear oil (3.7 mg). LC/MS (m/z) 318.1 (MH$^+$); RT=2.02 min; purity (UV, ELSD): 81.2%, 100%.

3d27, 4-[2-(4-Fluoro-phenylsulfanyl)-6-fluoro-phenyl]-piperidine trifluoro-acetic acid salt was prepared from 4-fluoro-1-iodo-benzene and collected as a clear oil (4.7 mg). LC/MS (m/z) 306.1 (MH$^+$); RT=2.05 min; purity (UV, ELSD): 74.2%, 100%.

3e1, 4-[2-(2,3-Dichloro-phenylsulfanyl)-5-fluoro-phenyl]-piperidine trifluoro-acetic acid salt was prepared from 1,2-dichloro-3-iodo-benzene and collected as a clear oil (2.8 mg). LC/MS (m/z) 356.1 (MH$^+$); RT=2.33 min; purity (UV, ELSD): 96.7%, 100%.

3e2, 4-[2-(2-Methoxy-phenylsulfanyl)-5-fluoro-phenyl]-piperidine trifluoro-acetic acid salt was prepared from 1-iodo-2-methoxy-benzene and collected as a clear oil (3.0 mg). LC/MS (m/z) 318.1 (MH$^+$); RT=2.02 min; purity (UV, ELSD): 96.0%, 99.8%.

3e3, 4-[2-(4-Trifluoromethoxy-phenylsulfanyl)-5-fluoro-phenyl]-piperidine trifluoro-acetic acid salt was prepared from 1-iodo-4-trifluoromethoxy-benzene and collected as a clear oil (7.0 mg). LC/MS (m/z) 371.9 (MH$^+$); RT=2.38 min; purity (UV, ELSD): 94.7%, 98.7%.

3e4, 4-[2-(4-Fluoro-2-methyl-phenylsulfanyl)-5-fluoro-phenyl]-piperidine trifluoro-acetic acid salt was prepared from 4-fluoro-1-iodo-2-methyl-benzene and collected as a clear oil (4.1 mg). LC/MS (m/z) 320.0 (MH$^+$); RT=2.21 min; purity (UV, ELSD): 94.1%, 99.8%.

3e5, 4-[2-(4-Trifluoromethyl-phenylsulfanyl)-5-fluoro-phenyl]-piperidine trifluoro-acetic acid salt was prepared from 1-iodo-4-trifluoromethyl-benzene and collected as a clear oil (3.9 mg). LC/MS (m/z) 356.1 (MH$^+$); RT=2.33 min; purity (UV, ELSD): 92.6%, 100%.

3e6, 4-[2-(3-Methyl-phenylsulfanyl)-5-fluoro-phenyl]-piperidine trifluoro-acetic acid salt was prepared from 1-iodo-3-methyl-benzene and collected as a clear oil (4.5 mg). LC/MS (m/z) 302.1 (MH$^+$); RT=2.19 min; purity (UV, ELSD): 860%, 87.8%.

3e7, 4-[2-(4-Chloro-2-methyl-phenylsulfanyl)-5-fluoro-phenyl]-piperidine trifluoro-acetic acid salt was prepared from 4-chloro-1-iodo-2-methyl-benzene and collected as a clear oil (6.1 mg). LC/MS (m/z) 336.1 (MH$^+$); T=2.38 min; purity (UV, ELSD): 85.5%, 70.5%.

3e8, 4-[2-(2,3-Dimethyl-phenylsulfanyl)-5-fluoro-phenyl]-piperidine trifluoro-acetic acid salt was prepared from 1-iodo-2,3-dimethyl-benzene and collected as a clear oil (6.1 mg). LC/MS (m/z) 316.0 (MH$^+$); RT=2.28 min; purity (UV, ELSD): 75.3%, 74.4%.

3e9, 4-[2-(2,3-Dihydro-benzo[1,4]dioxin-6-ylsulfanyl)-5-fluoro-phenyl]-piperidine trifluoro-acetic acid salt was prepared from 6-iodo-2,3-dihydro-benzo[1,4]dioxine and collected as a clear oil (4.8 mg). LC/MS (m/z) 346.0 (MH$^+$); RT=2.04 min; purity (UV, ELSD): 74.7%, 86.3%.

3e10, 4-[2-(4-Fluoro-3-methoxy-phenylsulfanyl)-5-fluoro-phenyl]-piperidine trifluoro-acetic acid salt was prepared from 2-fluoro-4-iodo-1-methoxy-benzene (prepared from 3-fluoro-4-methoxy-phenylamine by diazotization according to the general procedure by Tunney and Stille *J. Org. Chem.* 1987, 52, 748-753) and collected as a clear oil (3.7 mg). LC/MS (m/z) 336.0 (MH$^+$); RT=2.11 min; purity is (UV, ELSD): 73.4%, 88.6%.

3f1, 4-[2-(2-Methyl-phenylsulfanyl)-4-fluoro-phenyl]-piperidine trifluoro-acetic acid salt was prepared from 1-iodo-2-methyl-benzene and collected as a clear oil (4.1 mg). LC/MS (m/z) 302.1 (MH$^+$); RT=2.20 min; purity (UV, ELSD): 98.3%, 100%.

3f2, 4-[2-(2-Chloro-phenylsulfanyl)-4-fluoro-phenyl]-piperidine trifluoro-acetic acid salt was prepared from 1-chloro-2-iodo-benzene and collected as a clear oil (4.1 mg). LC/MS (m/z) 321.8 (MH$^+$); RT=2.19 min; purity (UV, ELSD): 96.6%, 100%.

3f3, 4-[2-(4-Fluoro-phenylsulfanyl)-4-fluoro-phenyl]-piperidine trifluoro-acetic acid salt was prepared from 1-fluoro-4-iodo-benzene and collected as a clear oil (2.7 mg). LC/MS (m/z) 305.8 (MH$^+$); RT=2.14 min; purity (UV, ELSD): 87.6%, 99.8%.

3f4, 4-[2-(3,4-Dimethyl-phenylsulfanyl)-4-fluoro-phenyl]-piperidine trifluoro-acetic acid salt was prepared from 1-iodo-3,4-dimethyl-benzene and collected as a clear oil (4.9 mg). LC/MS (m/z) 315.9 (MH$^+$); RT=2.35 min; purity (UV, ELSD): 91.7%, 100%.

3f5, 4-[2-(2-Chloro-4-Methyl-phenylsulfanyl)-4-fluoro-phenyl]-piperidine trifluoro-acetic acid salt was prepared from 2-chloro-1-iodo-4-methyl-benzene and collected as a clear oil (4.9 mg). LC/MS (m/z) 336.1 (MH$^+$); RT=2.33 min; purity (UV, ELSD): 93.0%, 99.3%.

3f6, 4-[2-(2-Fluoro-4-methyl-phenylsulfanyl)-4-fluoro-phenyl]-piperidine trifluoro-acetic acid salt was prepared from 2-fluoro-1-iodo-4-methyl-benzene and collected as a clear oil (4.4 mg). LC/MS (m/z) 319.9 (MH$^+$); RT=2.23 min; purity (UV, ELSD): 87.8%, 98.5%.

3f7, 4-[2-(5-Chloro-2-fluoro-phenylsulfanyl)-4-fluoro-phenyl]-piperidine trifluoro-acetic acid salt was prepared from 4-chloro-1-fluoro-2-iodo-benzene and collected as a clear oil (5.3 mg). LC/MS (m/z) 340.1 (MH$^+$); RT=2.24 min; purity (UV, ELSD): 93.1%, 99.7%.

3f8, 4-[2-(2-Chloro-4-fluoro-phenylsulfanyl)-4-fluoro-phenyl]-piperidine trifluoro-acetic acid salt was prepared from 2-chloro-4-fluoro-1-iodo-benzene and collected as a clear oil (5.1 mg). LC/MS (m/z) 340.0 (MH$^+$); RT=2.23 min; purity (UV, ELSD): 95.6%, 99.9%.

3f9, 4-[2-(2,3-Dimethyl-phenylsulfanyl)-4-fluoro-phenyl]-piperidine trifluoro-acetic acid salt was prepared from 1-iodo-2,3-dimethyl-benzene and collected as a clear oil (5.6 mg). LC/MS (m/z) 316.0 (MH$^+$); RT=2.34 min; purity (UV, ELSD): 97.4%, 99.8%.

3f10, 4-[2-(3-Fluoro-2-methyl-phenylsulfanyl)-4-fluoro-phenyl]-piperidine trifluoro-acetic acid salt was prepared from 1-fluoro-2-methyl-3-iodo-benzene and collected as a clear oil (4.0 mg). LC/MS (m/z) 319.9 (MH$^+$); RT=2.26 min; purity (UV, ELSD): 85.5%, 99.9%.

3f11, 4-[2-(4-Methoxy-2-methyl-phenylsulfanyl)-4-fluoro-phenyl]-piperidine trifluoro-acetic acid salt was prepared from 4-iodo-2-methyl-1-methoxy-benzene (prepared from 2-methyl-methoxy-phenylamine by diazotization according to the general procedure by Tunney and Stille *J. Org. Chem.* 1987, 52, 748-753) and collected as a clear oil (4.5 mg). LC/MS (m/z) 332.0 (MH$^+$); RT=2.19 min; purity (UV, ELSD): 96.1%, 99.8%.

3f12, 4-[2-(3-Fluoro-4-methyl-phenylsulfanyl)-4-fluoro-phenyl]-piperidine trifluoro-acetic acid salt was prepared from 2-fluoro-4-iodo-1-methyl-benzene and collected as a clear oil (4.3 mg). LC/MS (m/z) 320.0 (MH$^+$); RT=2.29 min; purity (UV, ELSD): 91.7%, 100%.

3f13, 4[2-(4-Fluoro-2-methyl-phenylsulfanyl)-4-fluoro-phenyl]-piperidine trifluoro-acetic acid salt was prepared from 4-fluoro-1-iodo-2-methyl-benzene and collected as a clear oil (4.7 mg). LC/MS (m/z) 320.1 (MH$^+$); RT=2.24 min; purity (UV, ELSD): 73.4%, 100%.

Method D

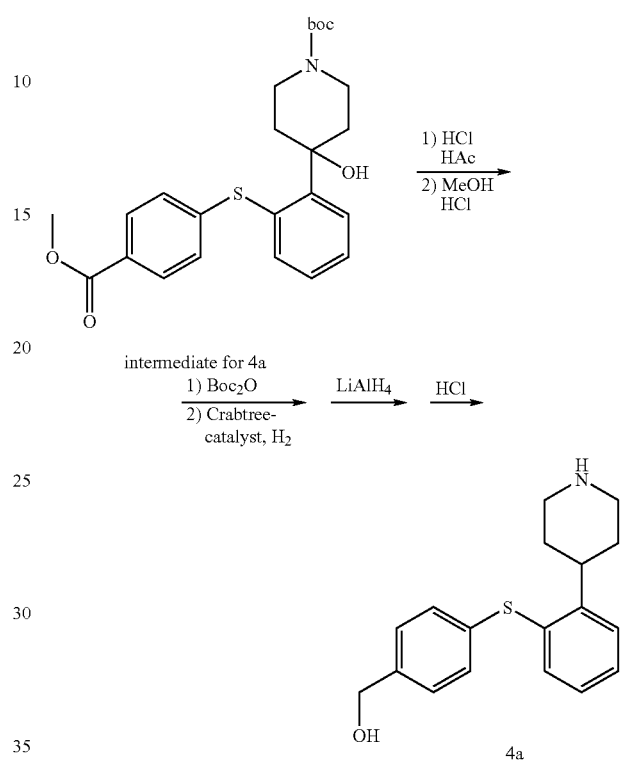

4a, 4-[2-(4-Hydroxymethyl-phenylsulfanyl)-phenyl]-piperidine hydrochloric acid salt Concentrated aqueous hydrochloric acid (38 mL) was added to a stirred solution of 1-tert-butoxycarbonyl-4-[2-(4-methoxycarbonyl-phenylsulfanyl)-phenyl]-piperidine-4-ol (1.25 g, 4 mmol) in acetic acid (12 mL). The solution was refluxed for 6 h, cooled to room temperature and then quenched by adding ice/water (100 mL). The solution was extracted with ethyl acetate (3×100 mL). The combined organic phases were dried over magnesium sulfate and the solvents were evaporated off. This crude material was dissolved in methanol (25 mL) and hydrogen chloride in diethyl ether (2M, 25 mL) was added. The mixture was refluxed for 12 h and the solvents were evaporated off. The residue was partioned between aqueous sodium hydroxide (2M, 100 mL) and ethyl acetate (2×100 mL). The ethyl acetate phase was dried over magnesium sulfate and the solvents were evaporated off. This material (4-[2-(4-methoxycarbonyl-phenylsulfanyl)-phenyl] piperidine, 0.98 g, 3 mmol) was dissolved in methylene chloride (25 mL) and Boc$_2$O (0.66 g, 3 mmol) was added. The reaction was stirred for 2 h and Crabtree's catalyst (0.13 g, 0.16 mmol) was added. The reaction mixture was treated with hydrogen gas (1.5 bar) overnight on a Parr shaker apparatus. The crude mixture was filtered through a plough of silica gel, and the filtrate was concentrated in vacuo. The residue was purified by chromatography on silica gel (eluent: ethyl acetate/heptane 1:2) to produce a solid (0.495 g). 0.285 g of this material was refluxed for 1 h a mixture of hydrogen chloride in diethyl ether (2M, 25 mL) and methanol (25 mL). The solvent was evaporated off and aqueous sodium hydroxide (2M, 50 mL) and ethyl acetate (2×50 mL) were added. The combined organic phases were dried over magnesium sulfate, and the solvent was evaporated off. This material (0.15 g) was dissolved in THF (25 mL) and lithium aluminium hydride (50 mg, 1.32 mmol) was added. The reaction was stirred overnight, before the reaction was quenched with water (0.1 mL) and saturated aqueous sodium hydroxide (0.2 mL). After stirring for 30 min, water (1 mL) was added, and the precipitate was filtered off. The organic filtrate phase was dried over magnesium sulfate, and the solvent was evaporated off. The crude product was purified by chromatography on silica gel (eluent: ethyl acetate/triethyl amine/methanol 8:1:2) to produce the free base which was precipitated as the hydrochloric acid salt from hydrogen chloride in diethyl ether (2M, 5 mL). Yield: 12.6 mg. LC/MS (m/z) 300.0 (MH+), RT=1.79; purity (UV, ELSD): 96.8%, 88%.

Method E

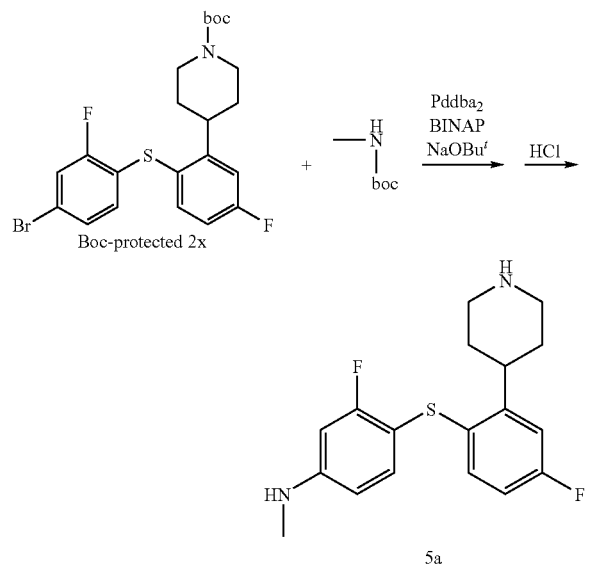

5a, 4[2-2-Fluoro-4-methyl-amine-phenylsulfanyl)-5-fluorophenyl]-piperidine trifluoro-acetic acid salt 1-tert-Butoxycarbonyl-4-[2-(2-fluoro-4-bromo-phenyl-sulfanyl)-5-fluoro-phenyl]-piperidine (Boc-protected 2x, 0.1 g, 0.21 mmol) and methyl-carbamic acid tert-butyl ester (0.033 g, 0.25 mmol; prepared from methyl amine and Boc$_2$O according to the procedure of Lee et al. *J. Am. Chem. Soc.*, 2003, 125, 7307-7312) dissolved in toluene (2 mL) was added to a stirred solution of bis(dibenzylideneacetone)palladium (0) (Pddba$_2$, 0.006 g, 0.011 mmol) and racemic 2,2'-bis-diphenylphosphanyl-[1,1']binaphthalenyl (BINAP, 0.009 g, 0.016 mmol) in toluene (1 mL). Sodium tert-butoxide (0.028 g, 0.28 mmol) was added and the reaction mixture was stirred overnight at 100° C. The reaction mixture was cooled to rt and filtered through celite using toluene (4×5 mL) to elude the product. The solvent was evaporated off and the residue was dissolved in methylene chloride (3 mL) and hydrogen chloride in diethyl ether (4M, 0.25 mL) was added and the reaction was stirred overnight. The solvent was evaporated off and the crude product was purified by HPLC to produce 4-[2-(4-methylamine-phenylsulfanyl)-5-fluorophenyl] piperidine 5a as the trifluoric acetic acid salt. Yield: 9.8 mg. LC/MS (m/z) 335.2 (MH+); RT=1.98; purity (UV, ELSD): 75.9%, 96.7%.

Method F

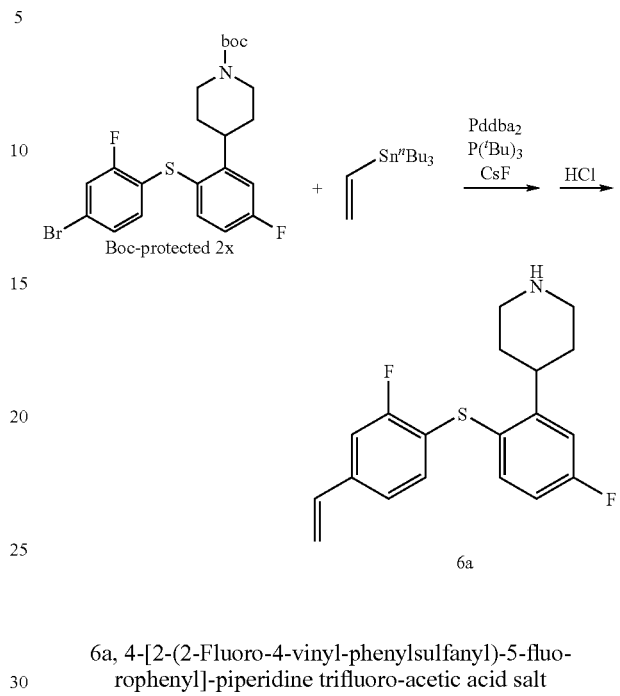

6a, 4-[2-(2-Fluoro-4-vinyl-phenylsulfanyl)-5-fluorophenyl]-piperidine trifluoro-acetic acid salt To a stirred solution of 1-tert-butoxycarbonyl-4-[2-(2-fluoro-4-bromo-phenylsulfanyl)-5-fluoro-phenyl]-piperidine (tert-butyl-oxo-carbonyl-protected 2x) (0.12 g, 0.25 mmol) and Pd$_2$dba$_3$ (0.007 g, 0.015 mmol) in 1,4-dioxane (1 mL) was added cesium fluoride (0.084 g, 0.055 mmol), vinyl-tri-n-butyltin (0.083 g, 0.26 mmol) and tris-tert-butyl-phosphine (0.091 mL, 10% in hexane, approx. 0.03 mmol). The reaction mixture was stirred overnight at 50° C. The reaction mixture was cooled to rt, diluted with acetonitrile (20 mL) and filtered. The filtrate was extracted with heptane (2×20 mL) and the acetonitrile phase was concentrated in vacuo. The residue was dissolved in methylene chloride (5 mL) and hydrogen chloride in diethyl ether (4M, 0.25 mL) was added and the reaction was stirred overnight. The solvent was evaporated off and the crude product (0.077 g) was purified by HPLC to produce 4-[2-(2-fluoro-4-vinyl-phenylsulfanyl)-5-fluorophenyl]-piperidine 6a as the trifluoro-acetic acid salt. LC/MS (m/z) 332.0 (MH+); RT=2.30; purity (UV, ELSD): 80.9%, 89.3%.

Measurements of [$^3$H]-5-HT Uptake into Rat Cortical Synaptosomes.

Whole brains from male Wistar rats (125-225 g), excluding cerebellum, are homogenized in 0.32 M sucrose supplemented with 1 mM nialamid with a glass/teflon homogenizer. The homogenate is centrifuged at 600×g for 10 min at 4° C. The pellet is discarded and the supernatant is centrifuged at 20.000×g for 55 min. The final pellet is homogenized (20 sec) in this assay buffer (0.5 mg original tissue/well). Test compounds (or buffer) and 10 nM [$^3$H]-5-HT are added to 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 0.2 mL. After 15 min incubation with radioligand at 37° C., samples are filtered directly on Unifilter GF/C glass fiber filters (soaked for 1 hour in 0.1% polyethylenimine) under vacuum and immediately washed with 3×0.2 mL assay buffer. Non-specific uptake is determined using citalopram (10 μM final concentration). Citalopram is included as reference in all experiments as dose-response curve.

Preferred compounds of the present invention exhibit serotonin reuptake inhibition below 200 nM ($IC_{50}$) in the assay above. More preferred are the compounds which exhibit inhibition below 100 nM and most preferably below 50 nM.

[$^3$H]Mesulergine Binding to 5-$HT_{2C}$ Receptors.

Cell lines expressing 10-20 pmol/mg protein human 5-$HT_{2C\text{-}VSV}$ receptors (Euroscreen) were harvested in ice-cold 50 mM Tris pH 7.7 buffer containing 125 mM NaCl and stored at –80° C. On the day of the experiment cells were quickly thawed and homogenized in 50 mM Tris pH 7.7 using an Ultra-Thurax. Aliqouts consisting of 6-30 μg protein, [$^3$H]Mesulergine (1 nM) and testsubstance were incubated for 30 min at 37° C. Total binding was determined using assay buffer (50 mM Tris pH 7.7) and non-specific binding was defined in the presence of 100 μM 5-HT. Bound and free [$^3$H]Mesulergine was separated by vacuum filtration on GF/B filters (pre-soaked in 0.1% PEI for ½ hour) and counted in a scintillation counter.

5-$HT_{2C}$ Receptor Efficacy as Determined by Fluorometry.

This assay was carried out as described by Porter et al. *British Journal of Pharmacology* 1999, 128, 13 with the modifications described below. 2 days before the experiment CHO cells expressing 10-20 pmol/mg protein human 5-$HT_{2C\text{-}VSV}$ receptors (Euroscreen) were plated at a density sufficient to yield a mono-confluent layer on the day of the experiment. The cells were dye loaded ($Ca^{2+}$-kit from Molecular Devices, and according to their instructions) at 37° C. in a 5% $CO_2$ incubator at 95% humidity. Lazer intensity was set to a suitable level to obtain basal values of approximately 8000 RFUs. The variation in basal fluorescence was less than 10%. $EC_{50}$ values were assessed using increasing concentrations of test compound covering 3 decades. $IC_{50}$ values were assessed challenging the $EC_{85}$ of 5-HT with concentrations covering 3 decades of test substances. Ki values were calculated using Cheng-Prusoff equation.

The invention claimed is:

1. A compound of formula I:

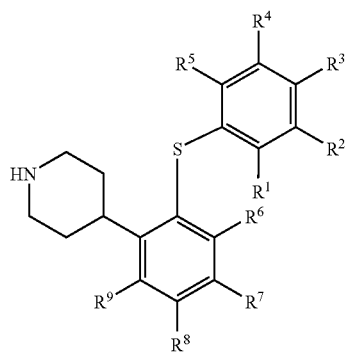

I wherein $R^1, R^2, R^3, R^4, R^5$ are independently selected from hydrogen, halogen, cyano, $C_{1-6}$-alkyl, $C_{2-6}$-alkenyl, $C_{2-6}$-alkynyl, $C_{1-6}$-alkyloxy, $C_{2-6}$-alkenyloxy, $C_{2-6}$-alkynyloxy, $C_{1-6}$-alkylsulfanyl, $C_{2-6}$-alkenylsulfanyl, $C_{2-6}$-alkynylsulfanyl, hydroxy, hydroxy-$C_{1-6}$-alkyl, hydroxy-$C_{2-6}$-alkenyl, hydroxy-$C_{2-6}$-alkynyl, halo-$C_{1-6}$-alkyl, halo-$C_{2-6}$-alkenyl, halo-$C_{2-6}$-alkynyl, halo-$C_{1-6}$-alkyloxy, halo-$C_{2-6}$-alkenyloxy, halo-$C_{2-6}$-alkynyloxy, or $NR^xR^y$, wherein $R^x$ and $R^y$ are independently selected from hydrogen, $C_{1-6}$-alkyl, $C_{2-6}$-alkenyl, $C_{2-6}$-alkynyl, cyano-$C_{1-6}$-alkyl, cyano-$C_{2-6}$-alkenyl, cyano-$C_{2-6}$-alkynyl, $C_{3-8}$-cycloalkyl, $C_{3-8}$-cycloalkenyl, $C_{3-8}$-cycloalkyl-$C_{1-6}$-alkyl $C_{3-8}$-cycloalkyl-$C_{2-6}$-alkenyl, $C_{3-8}$-cycloalkyl-$C_{2-6}$-alkynyl, $C_{3-8}$-cycloalkenyl-$C_{1-6}$-alkyl, $C_{3-8}$-cycloalkenyl-$C_{2-6}$-alkenyl, $C_{3-8}$-cycloalkenyl-$C_{2-6}$-alkynyl, or $NR^zR^w$—$C_{1-6}$-alkyl, $NR^zR^w$-$C_{2-6}$-alkenyl, $NR^zR^w C_{2-6}$-alkynyl, wherein $R^z$ and $R^w$ are independently selected from hydrogen $C_{1-6}$-alkyl, $C_{2-6}$-alkenyl, $C_{2-6}$-alkynyl, $C_{3-8}$-cycloalkyl, $C_{3-8}$-cycloalkenyl, or $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{3-8}$-cycloalkenyl-$C_{1-6}$-alkyl, $C_{1-6}$-cycloalkenyl-$C_{2-6}$-alkenyl, $C_{3-8}$-cycloalkenyl-$C_{2-6}$-alkynyl; or $R^x$ and $R^y$ together with the nitrogen to which they are attached form a 3-7-membered ring which optionally contains one further heteroatom;

$R^6, R^7, R^8, R^9$ are independently selected from hydrogen, halogen, $C_{1-6}$-alkyl, $C_{2-6}$-alkenyl, $C_{2-6}$-alkynyl, $C_{1-6}$-alkyloxy, $C_{2-6}$-alkenyloxy, $C_{2-6}$-alkynyloxy, $C_{1-6}$-alkylsulfanyl, $C_{2-6}$-alkenylsulfanyl, $C_{2-6}$-alkynylsulfanyl, hydroxy, hydroxy-$C_{1-6}$-alkyl, hydroxy-$C_{2-6}$-alkenyl, hydroxy-$C_{2-6}$-alkynyl, halo-$C_{1-6}$-alkyl, halo-$C_{2-6}$-alkenyl, halo-$C_{2-6}$-alkynyl, halo-$C_{1-6}$-alkyloxy, halo-$C_{2-6}$-alkenyloxy, halo-$C_{2-6}$-alkynyloxy, or $NR^xR^y$, wherein $R^x$ and $R^y$ are independently selected from hydrogen, $C_{1-6}$-alkyl, $C_{2-6}$-alkenyl, $C_{2-6}$-alkynyl, cyano-$C_{1-6}$alkyl, cyano-$C_{2-6}$-alkenyl, cyano-$C_{2-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{3-8}$-cycloalkenyl-$C_{1-6}$-alkyl, $C_{3-8}$-cycloalkenyl-$C_{2-6}$-alkenyl $C_{3-8}$-cycloalkenyl-$C_{2-6}$-alkynyl, or $NR^zR^w$-$C_{1-6}$-alkyl, $NR^zR^w$-$C_{2-6}$-alkenyl, $NR^zR^w$-$C_{2-6}$-alkynyl, wherein $R^z$ and $R^w$ are independently selected from hydrogen, $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-8}$cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{3-8}$-cycloalkenyl-$C_{1-6}$-alkyl, $C_{3-8}$-cycloalkenyl-$C_{2-6}$-alkenyl, $C_{3-8}$-cycloalkenyl-$C_{2-6}$-alkynyl; or $R^x$ and $R^y$ together with the nitrogen to which they are attached form a 3-7-membered ring which optionally contains one further heteroatom;

provided that at least two of $R^1, R^2, R^3, R^4, R^5, R^6, R^7, R^8$, and $R^9$ are different from hydrogen;

or a pharmaceutically acceptable salt thereof.

2. The compound of claim 1, wherein $R^1$ is hydrogen, $C_{1-6}$-alkyl, $C_{1-6}$-alkoxy or halogen.

3. The compound of claim 1, wherein $R^2$ is hydrogen, $C_{1-6}$-alkoxy, halogen, or $C_{1-6}$-alkyl.

4. The compound of claim 1, wherein $R^3$ is hydrogen, $C_{1-6}$-alkyl, $C_{1-6}$-alkoxy, or halogen.

5. The compound of claim 1, wherein $R^4$ is hydrogen, $C_{1-6}$-alkoxy, halogen, or $C_{1-6}$-alkyl.

6. The compound of claim 1, wherein $R^5$ is hydrogen, $C_{1-6}$-alkyl, $C_{1-6}$-alkoxy or halogen.

7. The compound of claim 1, wherein $R^5$ is hydrogen or halogen.

8. The compound of claim 1, wherein $R^7$ is hydrogen or halogen.

9. The compound of claim 1, wherein $R^8$ is hydrogen, $C_{1-6}$-alkyl, $C_{1-6}$-alkoxy, halo-$C_{1-6}$-alkyl, or halogen.

10. The compound of claim 1, wherein $R^9$ is hydrogen or halogen.

11. The compound of claim 1, wherein the compound of formula I has 3-4 substituents in the phenyl ring(s), selected from any one of $R^1$—$R^9$, which are different from hydrogen, and the remaining substituents are hydrogen.

12. A pharmaceutical composition comprising a compound of claim 1 or a pharmaceutically acceptable salt thereof and at least one pharmaceutically acceptable carrier or diluent.

13. A method of treating an affective disorder in a patient in need of such treatment, comprising administering a therapeutically effective amount of a compound of claim 1 or a pharmaceutically acceptable salt thereof to said patient.

14. The method of claim 13, wherein said affective disorder is depression.

15. A method of treating an anxiety disorder in a patient in need of such treatment, comprising administering a therapeutically effective amount of a compound of claim 1 or a pharmaceutically acceptable salt thereof to said patient.

16. The method of claim 15, wherein said anxiety disorder is selected from the group consisting of general anxiety disorder, social anxiety disorder, post traumatic stress disorder, obsessive compulsive disorder, panic disorder, panic attacks, specific phobias, social phobia and agoraphobia.

* * * * *

UNITED STATES PATENT AND TRADEMARK OFFICE
CERTIFICATE OF CORRECTION

PATENT NO. : 7,732,463 B2  Page 1 of 1
APPLICATION NO. : 10/551883
DATED : June 8, 2010
INVENTOR(S) : Ask Puschl et al.

It is certified that error appears in the above-identified patent and that said Letters Patent is hereby corrected as shown below:

Title page, item (75), reads "Ask Puschl, Frederiksberg (DK); Benny Bang-Andersen, Kobenhaven (DK); Morten Jorgensen, Bagsvaerd (DK); Thomas Ruhland, Roskilde (DK); Tine B. Stensbol, Vaerlose (DK)" should read -- Ask Puschl, Frederiksberg C (DK); Benny Bang-Andersen, Kobenhaven S (DK); Morten Jorgensen, Bagsvaerd (DK); Thomas Ruhland, Roskilde (DK); Tine B. Stensbol, Vaerlose (DK) --.

Title page, item (60), reads "(60) Provisional application No. 60/460,528, filed on Apr. 4, 2003." should read -- (60) 371 of application No. PCT/DK2004/000244, filed on Apr. 2, 2004.
(60) Provisional application No. 60/460,528, filed on Apr. 4, 2003. --.

Column 9, line 33, reads "4-[2-(4-Trifluoromethyl-phenylsulfanyl)-phenyl]-" should read -- 4-[2-(4-Trifluoromethyl-phenylsulfanyl)-phenyl]-piperdine --.

Column 16, line 23, reads "wherein $R^1$—$R^9$ are as previously described, and R is a car-" should read -- wherein $R^1$—$R^9$ are as previously described, and $R^1$ is a car- --.

Column 51, line 63, reads "wherein" should read -- wherein, --.

Column 52, line 9, reads "cloalkyl-$C_{1-6}$-alkyl $C_{3-8}$-cycloalkyl-$C_{2-6}$-alkenyl, $C_{3-8}$-" should read -- cloalkyl-$C_{1-6}$-alkyl, $C_{3-8}$-cycloalkyl-$C_{2-6}$-alkenyl, $C_{3-8}$- --.

Column 52, line 14, reads "pendently selected from hydrogen $C_{1-6}$-alkyl, $C_{2-6}$-alk-" should read -- pendently selected from hydrogen, $C_{1-6}$-alkyl, $C_{2-6}$-alk- --.

Column 52, line 37, reads "enyl-$C_{2-6}$-alkenyl $C_{3-8}$-cycloalkenyl-$C_{2-6}$-alkynyl, or" should read -- enyl-$C_{2-6}$-alkenyl, $C_{3-8}$-cycloalkenyl-$C_{2-6}$-alkynyl, or --.

Column 52, line 61, reads "7. The compound of claim 1, wherein $R^5$ is hydrogen or" should read -- 7. The compound of claim 1, wherein $R^6$ is hydrogen or --.

Signed and Sealed this

Thirty-first Day of August, 2010

David J. Kappos
*Director of the United States Patent and Trademark Office*